(12) United States Patent
Hadida-Ruah et al.

(10) Patent No.: US 7,999,113 B2
(45) Date of Patent: *Aug. 16, 2011

(54) MODULATORS OF CYSTIC FIBROSIS TRANSMEMBRANE CONDUCTANCE REGULATOR

(75) Inventors: Sarah Hadida-Ruah, La Jolla, CA (US); Frederick Van Goor, San Diego, CA (US); Mark Miller, San Diego, CA (US); Jason McCartney, Cardiff-by-the-Sea, CA (US); Jinglan Zhou, San Diego, CA (US); Vijayalaksmi Arumugam, San Marcos, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 420 days.

This patent is subject to a terminal disclaimer.

(21) Appl. No.: 11/503,449

(22) Filed: Aug. 11, 2006

(65) Prior Publication Data

US 2008/0161371 A1 Jul. 3, 2008

Related U.S. Application Data

(60) Provisional application No. 60/707,380, filed on Aug. 11, 2005, provisional application No. 60/732,476, filed on Nov. 2, 2005.

(51) Int. Cl.
*A61K 31/426* (2006.01)
*C07D 277/44* (2006.01)

(52) U.S. Cl. .................................. 548/195; 514/371
(58) Field of Classification Search .................. 548/195
See application file for complete search history.

(56) References Cited

U.S. PATENT DOCUMENTS

| | | |
|---|---|---|
| 2005/0130970 A1 | 6/2005 | Miller et al. |
| 2007/0244159 A1 | 10/2007 | Hadida-Ruah et al. |
| 2008/0009524 A1 | 1/2008 | Hadida-Ruah et al. |
| 2008/0019915 A1 | 1/2008 | Hadida-Ruah et al. |
| 2008/0044355 A1 | 2/2008 | Ruah et al. |
| 2008/0113985 A1 | 5/2008 | Ruah et al. |
| 2008/0176899 A1* | 7/2008 | Ruah et al. ............... 514/321 |
| 2008/0286204 A1 | 11/2008 | Hadida-Ruah et al. |
| 2008/0306062 A1 | 12/2008 | Hadida-Ruah et al. |

FOREIGN PATENT DOCUMENTS

WO WO-2005/075435 A1 * 8/2005

OTHER PUBLICATIONS

International Search Report for corresponding PCT Application No. PCT/US2006/031457, Jun. 2, 2007.

* cited by examiner

*Primary Examiner* — Laura L. Stockton
(74) *Attorney, Agent, or Firm* — Michael J. DiVerdi

(57) ABSTRACT

The present invention relates to modulators of cystic fibrosis Transmembrane Conductance Regulator ("CFTR"), compositions thereof, and methods therewith. The present invention also relates to methods of treating CFTR mediated diseases using such modulators.

25 Claims, No Drawings

MODULATORS OF CYSTIC FIBROSIS TRANSMEMBRANE CONDUCTANCE REGULATOR

CROSS-REFERENCE TO RELATED APPLICATIONS

The present invention claims priority under 35 U.S.C. §119 to U.S. Provisional Application Ser. No. 60/707,380, filed Aug. 11, 2005, and U.S. Provisional Application Ser. No. 60/732,476, filed Nov. 2, 2005.

TECHNICAL FIELD OF THE INVENTION

The present invention relates to modulators of cystic fibrosis Transmembrane Conductance Regulator ("CFTR"), compositions thereof, and methods therewith. The present invention also relates to methods of treating CFTR mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis, the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the cystic fibrosis associated gene suffer from the debilitating and fatal effects of cystic fibrosis, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in cystic fibrosis patients. In addition to respiratory disease, cystic fibrosis patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the cystic fibrosis associated gene, individuals with a single copy of the cystic fibrosis associated gene exhibit increased resistance to cholera and to dehydration resulting from diarrhea—perhaps explaining the relatively high frequency of the cystic fibrosis gene within the population.

Sequence analysis of the CFTR gene of cystic fibrosischromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, >1000 disease causing mutations in the cystic fibrosis gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the endoplasmic reticulum ("ER"), and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for cystic fibrosis disease, but for a wide range of other isolated and inherited diseases. The two ways that the ER machinery can malfunction is either by loss of coupling to ER export of the proteins leading to degradation, or by the ER accumulation of these defective/misfolded proteins (Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)). The diseases associated with the first class of ER malfunction are cystic fibrosis (due to misfolded ΔF508-CFTR as discussed above), hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic E-coli (ETEC) having the K99 pilus antigen. Common viral causes of diarrhea include rotavirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of CFTR activity, and compositions thereof, that can be used to modulate the activity of the CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of CFTR activity. These formula I or formula II:

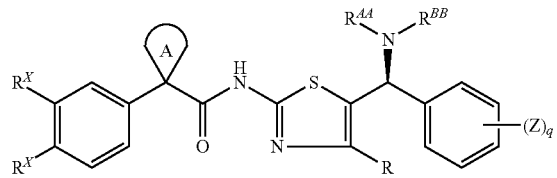

I

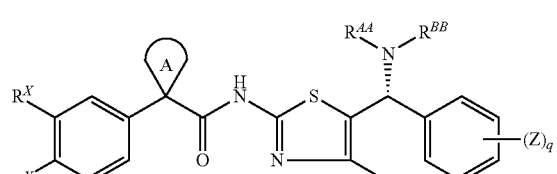

II or a pharmaceutically acceptable salt thereof, wherein $R^X$, ring A, R, $R^{AA}$, $R^{BB}$, Z, and q are described below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myeloperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (di), neurophyseal di, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease.

DETAILED DESCRIPTION OF THE INVENTION

I. General Description of Compounds of the Invention:

The present invention provides compounds of formula I or formula II:

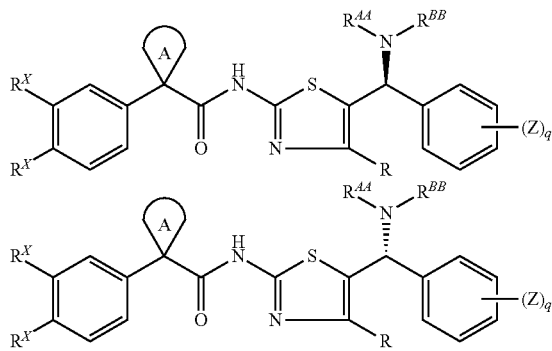

or a pharmaceutically acceptable salt thereof, wherein:

each $R^X$ is independently hydrogen, halo, $CF_3$, C1-C4 alkyl, or —OC1-C4 alkyl; provided that both $R^X$ are not simultaneously hydrogen; or the two $R^X$, taken together form ring (a):

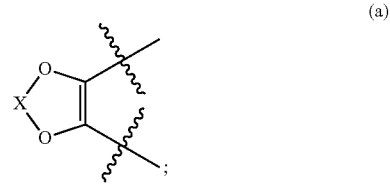

(a)

X is $CH_2$, $CF_2$, $CH_2$—$CH_2$, or $CF_2$—$CF_2$;

ring A is 3-7 membered monocyclic cycloalkyl ring;

$R^{AA}$ and $R^{BB}$, taken together with the nitrogen atom, form a pyrrolidinyl ring substituted with OR';

R' is hydrogen or C1-C6 aliphatic, wherein up to two carbon units of said aliphatic are optionally and independently replaced by —CO—, —CS—, —COCO—, —CONR—, —CONRNR—, —CO₂—, —OCO—, —NRCO₂—, —O—, —NRCONR—, —OCONR—, —NRNR—, —NRNRCO—, —NRCO—, —S—, —SO, —SO₂—, —NR—, —SO₂NR—, NRSO₂—, or —NRSO₂NR—;

R is hydrogen or C1-C6 aliphatic;

Z is an electron withdrawing substituent; and q is 0-3.

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR.

The term "modulating" as used herein means increasing or decreasing by a measurable amount.

The term "correction" as used herein means increasing the number of CFTR in a membrane of a cell.

The term "potentiator" as used herein means a compound that increases the gating activity of CFTR in a membrane of a cell.

The term "electron withdrawing substituent", as used herein means an atom or a group that is electronegative relative to hydrogen. See, e.g., "Advanced Organic Chemistry: Reactions, Mechanisms, and Structure," Jerry March, 4$^{th}$ Ed., John Wiley & Sons (1992), e.g., pp. 14-16, 18-19, etc. Exemplary such substituents include halo, CN, COOH, CF$_3$, etc.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless otherwise specified, the term "aliphatic" or "aliphatic group" by itself, as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic C3-C8 hydrocarbon or bicyclic C8-C12 hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "unsaturated", as used herein, means that a moiety has one or more units of unsaturation.

Unless stereochemically specified, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers, including mixtures containing an excess of one enantiomer relative to the other enantiomer or an excess of one diastereomer relative to another. Unless otherwise specified, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

In one embodiment, each $R^X$ is independently hydrogen, halo, or CF$_3$; provided that both $R^X$ are not simultaneously hydrogen. In another embodiment, one $R^X$ is hydrogen and the other $R^X$ is halo or CF$_3$. In another embodiment, both $R^X$ are halo.

In one embodiment, the two $R^X$ groups taken together form ring (a).

In certain embodiments, X is CH$_2$. In other embodiments, X is CF$_2$. Or, X is CH$_2$—CH$_2$. In certain other embodiments, X is CF$_2$—CF$_2$;

In one embodiment, ring A is cyclopropyl, cyclopentyl, or cyclohexyl. In another embodiment, ring A is cyclopropyl or cyclopentyl. In certain embodiments, ring A is cyclopropyl.

In one embodiment, R is hydrogen. Or, R is C1-C6 alkyl. Exemplary R includes methyl, ethyl, or propyl.

In one embodiment, R' is hydrogen. Or, R' is C1-C6 alkyl. Exemplary R' include methyl, ethyl, propyl, or C(O)Me.

In one embodiment, $R^{AA}$ and $R^{BB}$, taken together, form a pyrrolidinyl with an OH substituent.

In one embodiment, Z is selected from halo, CF$_3$, or difluoromethylenedioxy.

In another embodiment, Z is fluoro or chloro.

In one embodiment, q is 0. Or, q is 1-2. In certain embodiments, q is 1. Or, q is 2.

In another embodiment, compounds of formula I or formula II comprise one or more, and preferably all, of the following features:
the two $R^X$ are taken together to form ring (a);
X is CH$_2$;
ring A is cyclopropyl;
R' is hydrogen;
q is 1 or 2; and
Z is halo, CF$_3$, or difluoromethylenedioxy.

In another embodiment, compounds of formula I or formula II comprise one or more, and preferably all, of the following features:
the two $R^X$ are taken together to form ring (a);
X is CF$_2$;
R is hydrogen;
ring A is cyclopropyl;
R' is hydrogen;
q is 1 or 2; and
Z is halo, CF$_3$, or difluoromethylenedioxy.

In another embodiment, compounds of formula I or formula II comprise one or more, and preferably all, of the following features:
the two $R^X$ are taken together to form ring (a);
X is CF$_2$;
ring A is cyclopropyl;
R' is hydrogen;
q is 1 or 2; and
Z is halo, CF$_3$, or difluoromethylenedioxy.

In another embodiment, compounds of formula I or formula II comprise one or more, and preferably all, of the following features:
the two $R^X$ are taken together to form ring (a);
X is CF$_2$;
R is hydrogen;

ring A is cyclopropyl;

R' is hydrogen;

q is 1 or 2; and

Z is halo, CF$_3$, or difluoromethylenedioxy. In one embodiment of compounds of formula I, R$^{AA}$ and R$^{BB}$, taken together with the nitrogen atom, form the following ring (i):

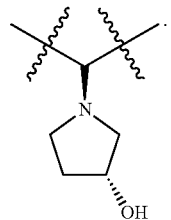

In one embodiment of compounds of formula II, R$^{AA}$ and R$^{BB}$, taken together with the nitrogen atom, form the following ring (ii):

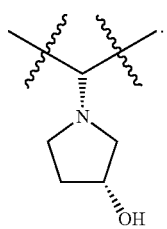

In one embodiment of compounds of formula I, R$^{AA}$ and R$^{BB}$, taken together with the nitrogen atom, form the following ring (iii):

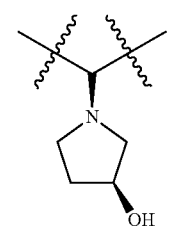

In one embodiment of compounds of formula II, R$^{AA}$ and R$^{BB}$, taken together with the nitrogen atom, form the following ring (iv):

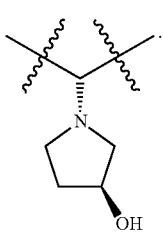

In an alternative embodiment, the present invention provides intermediates having formula I' or formula II':

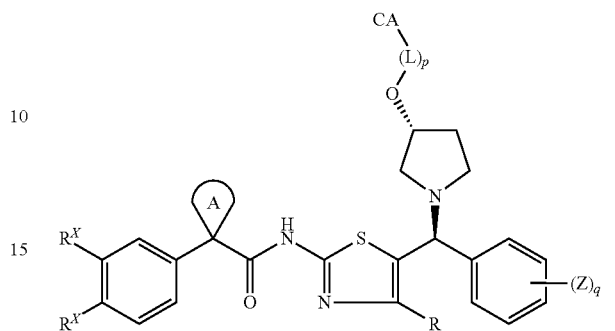

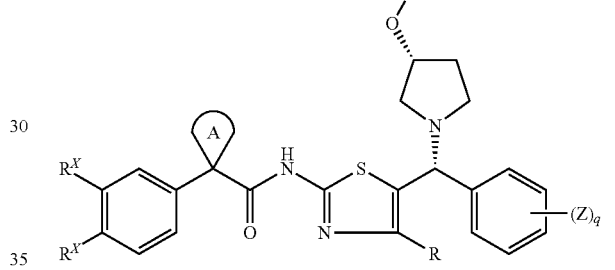

wherein:

R$^X$, R, ring A, Z, and q are as defined above;

L is a linker selected from C(O), SO$_2$;

p is 0 or 1; and

CA is a suitable chiral auxiliary.

The term "chiral auxiliary" as used herein means an asymmetric molecule or molecular fragment that is used to achieve the chemical resolution of a racemic or diastereomeric mixture. Such chiral auxiliaries may possess one chiral center such as methylbenzylamine or several chiral centers such as menthol. The purpose of a chiral auxiliary, once built into the starting material, is to allow simple separation of the resulting diastereomeric mixture. See, for example, J. Jacques et al., "*Enantiomers, Racemates And Resolutions*," pp. 251-369, John Wiley & Sons, New York (1981); E. L. Eliel & S. H. Wilen, "*Stereochemistry of Organic Compounds*," pp. 868-870, John Wiley & Sons (1994).

Suitable chiral auxiliaries useful in the present invention include those that are amenable to attachment to the linker L above (i.e., p is 1) or directly to the oxygen atom (i.e., p is 0). Exemplary such chiral auxiliaries are found in, e.g., E. L. Eliel & S. H. Wilen, ibid, pp. 337-340.

In one embodiment, CA, L, p, and the oxygen atom linked thereto, taken together, is (+)-10-camphorsulfonate, (1S,4R)-(−)-ω-camphanic ester, (1R,2S,5R)-(−) mentholcarbonate, (1S,2R,5S)-(+)-mentholcarbonate, (1R,2R)-1-phenyl-2-cyclopropylester, or (3R)-tetrahydrofuran-3-carbonate.

Exemplary compounds of the present invention are shown below in Table 1.
TABLE 1
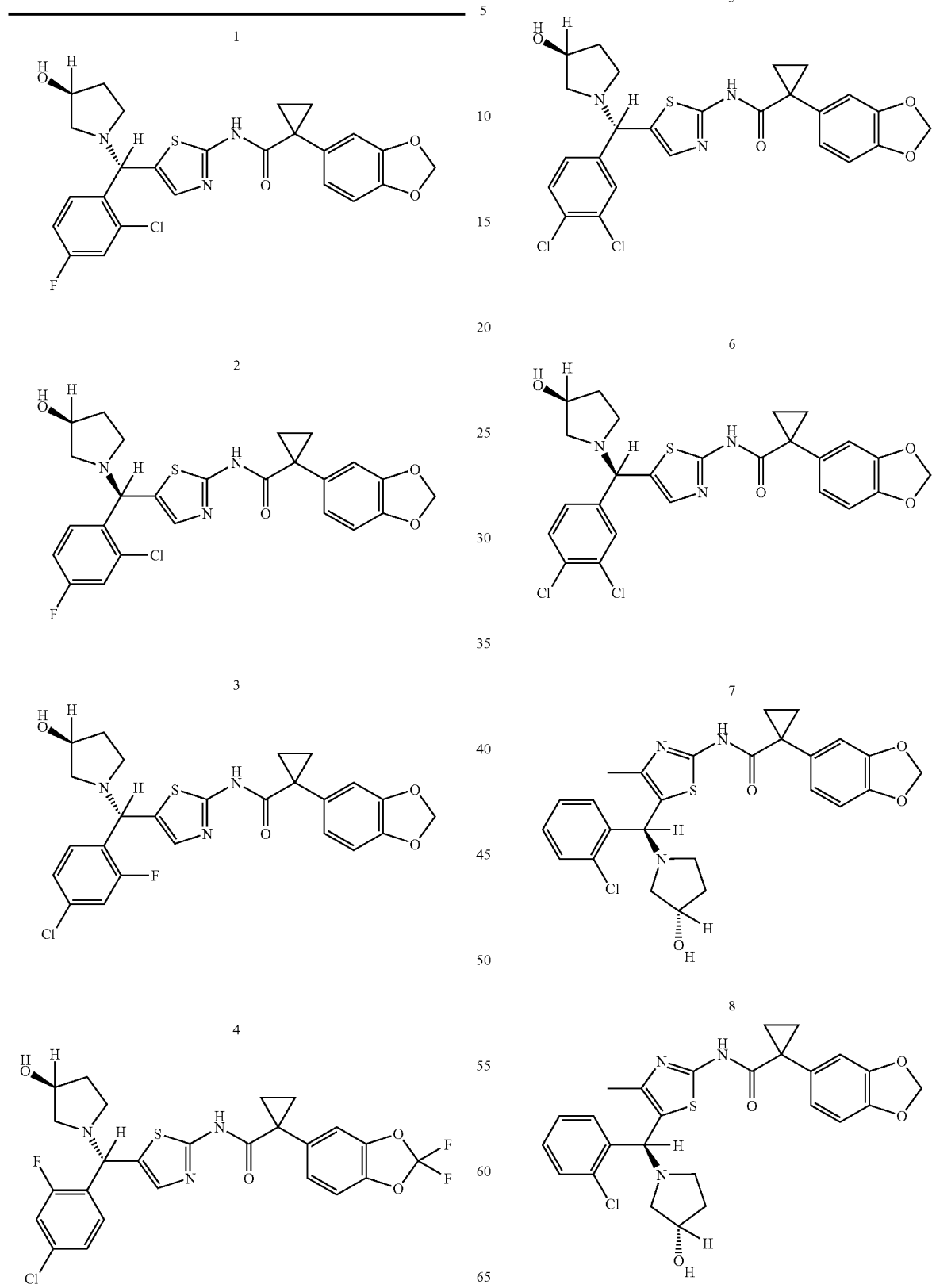

TABLE 1-continued

9

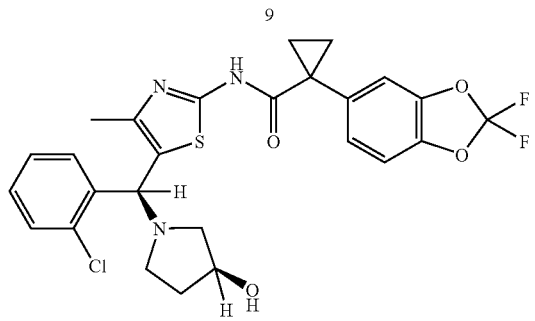

10

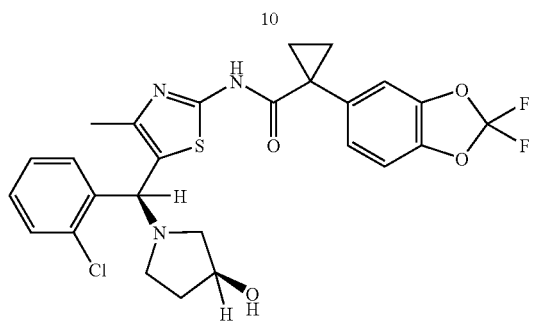

11

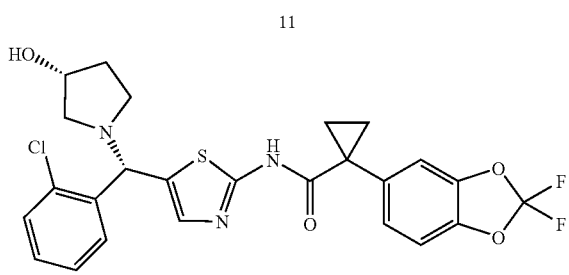

12

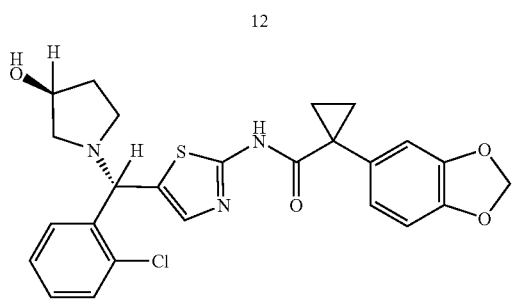

13

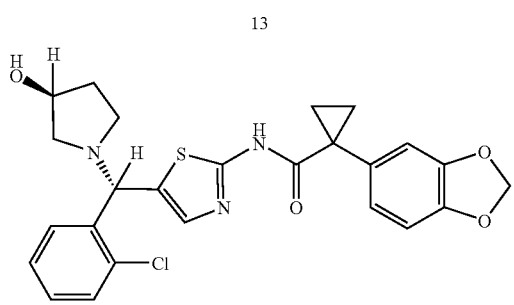

In one embodiment, the present invention provides a method for producing a compound of formula I or formula II:

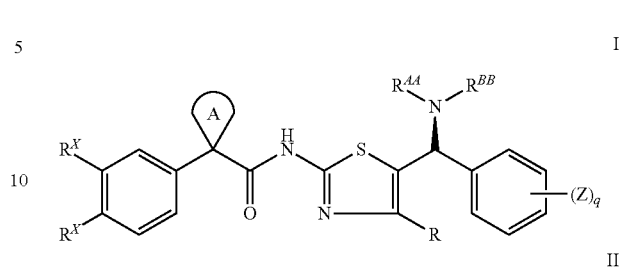

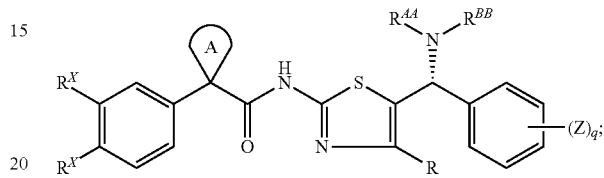

comprising the step of reacting under a first suitable conditions a compound of formula R-1 with either a compound of formula I-A to produce said compound of formula I, or a compound of formula II-A to produce said compound of formula II:

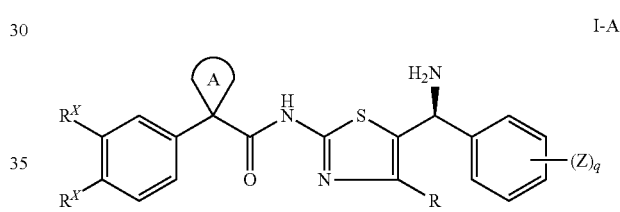

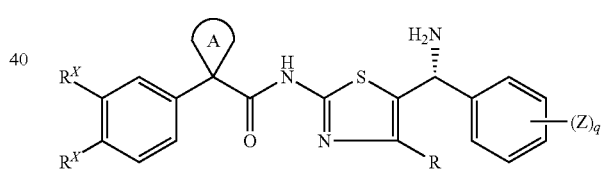

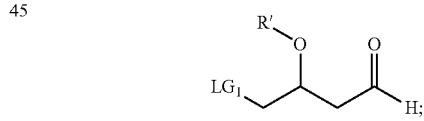

wherein:

each $R^X$ is independently hydrogen, halo, $CF_3$, C1-C4 alkyl, or —OC1-C4 alkyl; provided that both $R^X$ are not simultaneously hydrogen; or the two $R^X$, taken together form ring (a):

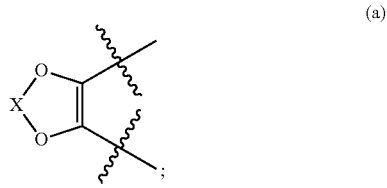

X is $CH_2$, $CF_2$, $CH_2$—$CH_2$, or $CF_2$—$CF_2$;

ring A is 3-7 membered monocyclic cycloalkyl ring;

$R^{AA}$ and $R^{BB}$, taken together with the nitrogen atom, form a pyrrolidinyl ring substituted with OR';

R' is hydrogen or C1-C6 aliphatic, wherein up to two carbon units of said aliphatic are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, NRSO$_2$—, or —NRSO$_2$NR—;

R is hydrogen or C1-C6 aliphatic;

Z is an electron withdrawing substituent; and q is 0-3; and $LG_1$ is a first suitable leaving group As used herein, the term "first suitable conditions" means conditions suitable to effectuate the reaction between compound of formula I-A and compound of formula R-1 or between compound of formula II-A and compound of formula R-1. Such suitable conditions include, e.g., a first suitable solvent, a first suitable temperature, and a suitable reducing agent. One of skill in the art will be well aware of various such suitable conditions that effectuate the reaction between compound of formula I-A and compound of formula R-1 or between compound of formula II-A and compound of formula R-1.

In one embodiment, the first suitable solvent is a polar aprotic, a polar protic solvent, an apolar solvent, or a suitable combination thereof. Exemplary solvents useful as first suitable solvent include methanol, ethanol, propanol, isopropanol, t-butanol, dichloromethane, dichloroethane, toluene, tetrahydrofuran, dioxane, diethylether, dimethylether, acetonitrile, dimethylformamide, DMAC, or NMP.

In one embodiment, the first suitable temperature is a temperature that is sufficient to effectuate the reaction between compound of formula I-A and compound of formula R-1 in the first suitable solvent. In another embodiment, the first suitable temperature is a temperature that is sufficient to effectuate the reaction between compound of formula II-A and compound of formula R-1 in the first suitable solvent. Exemplary first suitable temperature includes between about 0° C. to about 110° C. In one embodiment, the first suitable temperature is between about 0° C. to about 25° C.

In one embodiment, the suitable reducing agent is a reducing agent that is capable effectuating the reaction between compound of formula I-A and compound of formula R-1. In another embodiment, the suitable reducing agent is a reducing agent that is capable effectuating the reaction between compound of formula II-A and compound of formula R-1. One of skill in the art will be well aware of suitable reducing agents for that reaction. Agents suitable for the present invention include a metallo-borohydride or a reagent capable of catalytic hydrogenation. Exemplary such suitable reducing agents include sodium borohydride, sodium cyanoborohydride, lithium borohydride, sodium triacetoxyborohydride, calcium borohydride, hydrogene in the presence of a suitable metal catalyst such as Pd/C.

In another embodiment, $LG_1$ is a first suitable leaving group that is capable of displacement to produce compound of formula I. or compound of formula II. See, "Advanced Organic Chemistry Reactions, Mechanisms, and Structure," pp. 339-357, Jerry March, 4$^{th}$ Ed., John Wiley & Sons (1992).

The method according to claim 1, wherein $LG_1$ is selected from alkysulfonate, arylsulfonate, halide, alkyl carboxylate.

In one embodiment, the compound of formula I-A is produced from formula I-B:

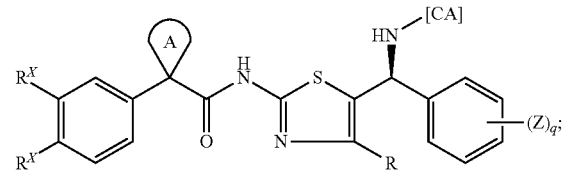

wherein [CA] is a suitable chiral auxiliary;

said method comprising the step of removing said chiral auxiliary under a second suitable conditions.

In an alternative embodiment, the compound of formula II-A is produced from formula I'-B:

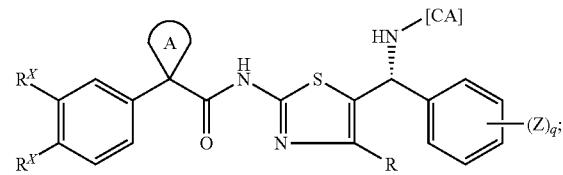

wherein [CA] is a suitable chiral auxiliary;

said method comprising the step of removing said chiral auxiliary under a second suitable conditions.

A "suitable chiral auxiliary" above in compound of formula I'-B or formula I-B is a chiral auxiliary that is capable of attachment to an amino group. An isomeric mixture of a compound containing such an amino group with a suitable chiral auxiliary attached thereto is readily separated into its individual isomers by suitable separation means. See, for example, J. Jacques et al., "*Enantiomers, Racemates And Resolutions,*" pp. 251-369, John Wiley & Sons, New York (1981); E. L. Eliel & S. H. Wilen, "*Stereochemistry of Organic Compounds,*" pp. 868-870, John Wiley & Sons (1994).

In one embodiment, said suitable chiral auxiliary is an alkylsulfoxyl group.

In another embodiment, said suitable second conditions comprises a suitable protic acid and a suitable second solvent.

In one embodiment, said suitable second solvent is selected from a polar aprotic solvent or a protic solvent. Exemplary polar aprotic solvents include dioxane, tetrahydrofurane, diethyl ether, dichloromethane, etc. Exemplary protic solvents include methanol, ethanol, i-propanaol, t-butanol, etc.

In one embodiment, said suitable second solvent is a polar aprotic solvent.

In another embodiment, said compound of formula I-B and compound of formula I'-B is produced by reacting, respectively, a compound of formula I-C or formula II-C with a compound of formula R-2 under a third suitable conditions:

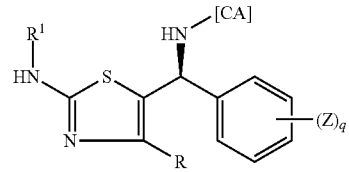

-continued

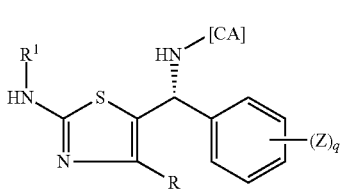

II-C

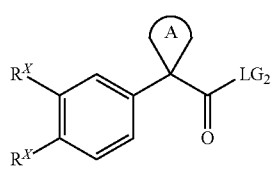

R-2 wherein:
R is hydrogen or C1-C6 aliphatic;
R¹ is hydrogen or a first suitable protecting group;
[CA] is a suitable chiral auxiliary; and
LG₂ is a second suitable leaving group.

In one embodiment, LG₂ is selected from halide, OC(O)(C1-C6 alkyl), pentafluorophenoxy, C1-C6 alkoxy, OCO₂(C1-C6 alkyl) or hydroxy.

In one embodiment, R¹ is hydrogen.

In another embodiment, said third suitable conditions comprises a third suitable coupling agent and a third suitable solvent.

In another embodiment, said suitable coupling agent is selected from DCC, DCI, HATU, TCPH, or HBTU.

In one embodiment, said third suitable solvent is selected from dichloromethane, dioxane, acetonitrile, DMF, dichloroethane, or tetrahydrofuran.

In another embodiment, said compound of formula I-C or formula II-C is produced from an isomeric mixture of a compound of formula R-3:

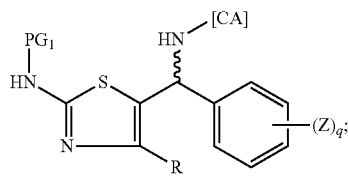

R-3 wherein:
R, Z, and q are as defined above;
PG₁ is a second suitable protecting group; and
[CA] is a suitable chiral auxiliary;
said method comprising two steps, wherein one of said two steps is separating said isomeric mixture using suitable separation means, and the other of said two steps is the conversion of PG₁ to R¹ in a fourth suitable conditions.

In one embodiment, said suitable separation means comprises suitable chromatographic means. Exemplary such means include column chromatography or thin layer chromatography.

In another embodiment, said suitable separation means comprises suitable crystallization means.

In another embodiment, said fourth suitable conditions comprises a suitable deprotecting reagent and a fourth suitable solvent. An exemplary suitable deprotecting reagent is trifluoroacetic acid.

In one embodiment, said fourth suitable solvent is a polar aprotic solvent. Exemplary solvents include dichloromethane, tetrahydrofuran, dioxane, diethyl ether, etc.

In another embodiment, said compound of formula R-3 is produced from a compound of formula R-4 and a compound of formula R-5:

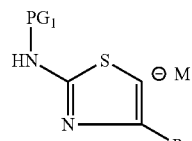

R-4

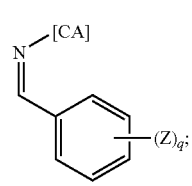

R-5 wherein:
PG₁ is a second suitable protecting group;
M is a suitable metal cation; and
[CA] is a suitable chiral auxiliary;
said method comprising the steps of reacting said compound of formula R-4 with said compound of formula R-5 in a fifth suitable conditions.

In one embodiment, said M is selected from Li⁺, Na⁺, or Mg⁺⁺.

In another embodiment, said PG₁ is selected from an alkylcarbamate, trifluoroacetyl, trialkylsilyl, or pivaloyl. Or, said PG₁ is BOC or trimethylsilyl.

In one embodiment, said fifth suitable conditions comprises a fifth suitable solvent and a fifth suitable temperature. In one embodiment, said suitable temperature is about −78 degrees C.

In another embodiment, said fifth suitable solvent is tetrahydrofuran.

In an alternative embodiment, said compound of formula R-1 is:

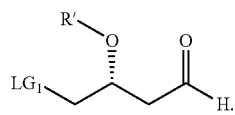

Or, said compound of formula R-1 is:

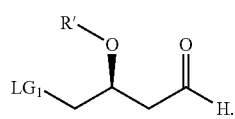

In another embodiment, said compound of formula I or formula II are selected from Table 1.

4. General Synthetic Schemes

The compounds of this invention may be prepared by methods known in the art. Exemplary synthetic routes to prepare compounds of this invention are illustrated below.

Scheme I-A below illustrates a process for producing intermediate A:

Scheme I-A:

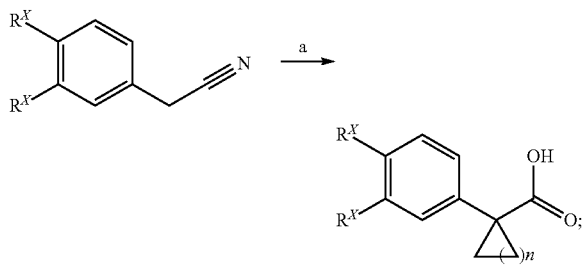

A a) 50% NaOH, Y(CH$_2$)$_n$Y, BTEAC (benzyl triethyl ammonium chloride);
Y = suitable leaving group.

Scheme I-B below illustrates a process for producing intermediate B.

Scheme I-B:

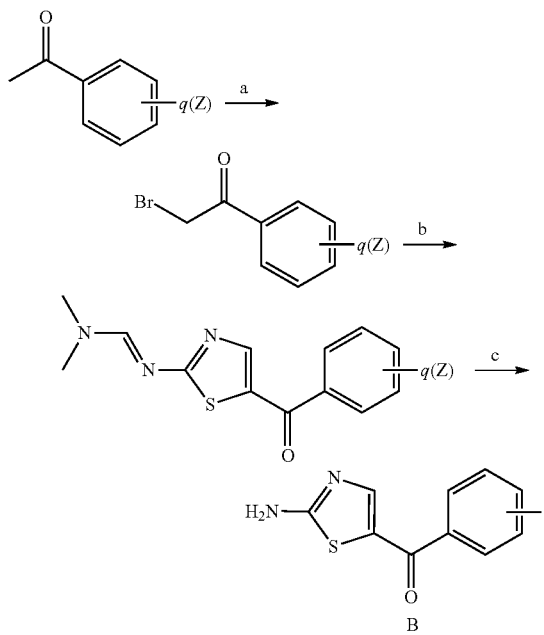

B a) Br$_2$;
b) thiourea, (Me)$_2$NCH(OMe)$_2$;
c) HCl

Scheme I-C below illustrates a process for producing compounds of formula I or formula II:

Scheme I-C:

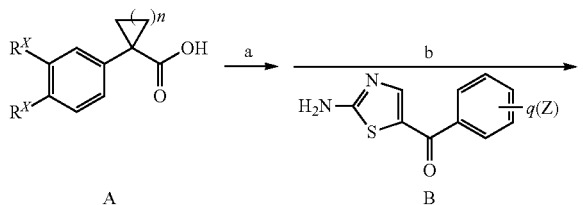

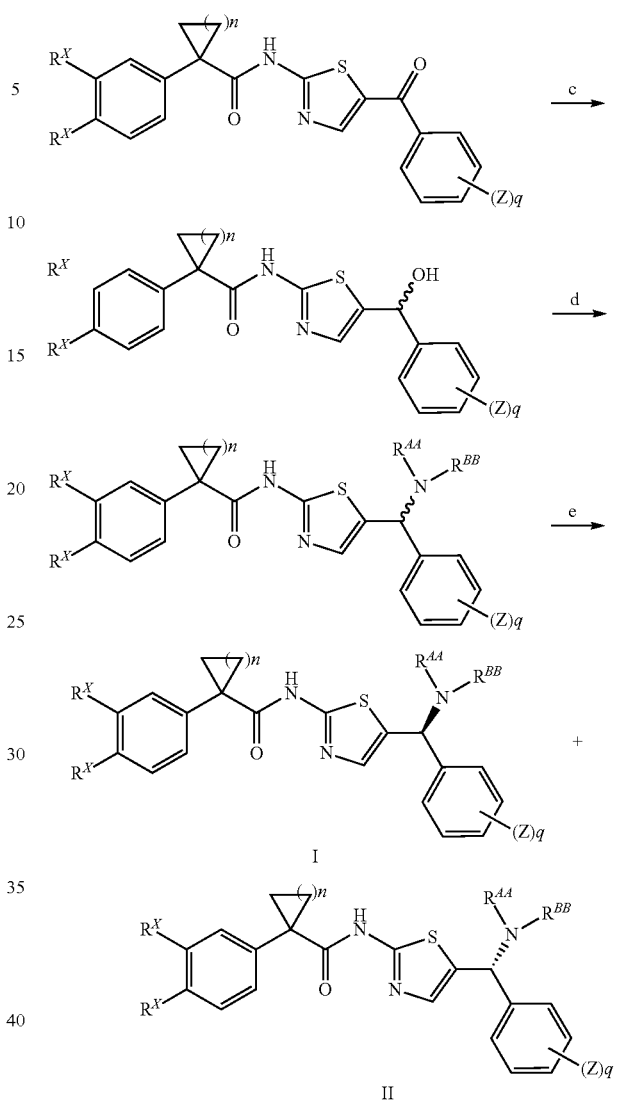

a) SOCl$_2$, DMF;
b) 1,4-dioxane, Et$_3$N;
c) NaBH$_4$, MeOH;
d) i) CH$_3$SO$_2$Cl, DCM, Et$_3$N;
   ii) R$^{AA}$R$^{BB}$NH;
e) chiral chromatography Scheme I-D illustrates the synthesis of an exemplary compound of the present invention.

Scheme I-D:

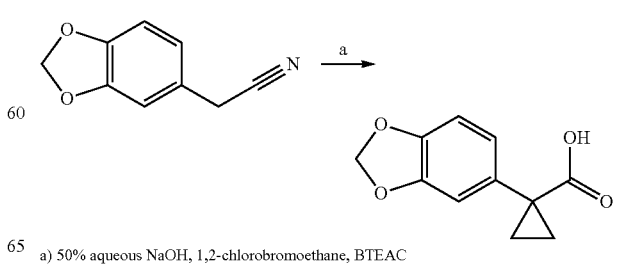

a) 50% aqueous NaOH, 1,2-chlorobromoethane, BTEAC

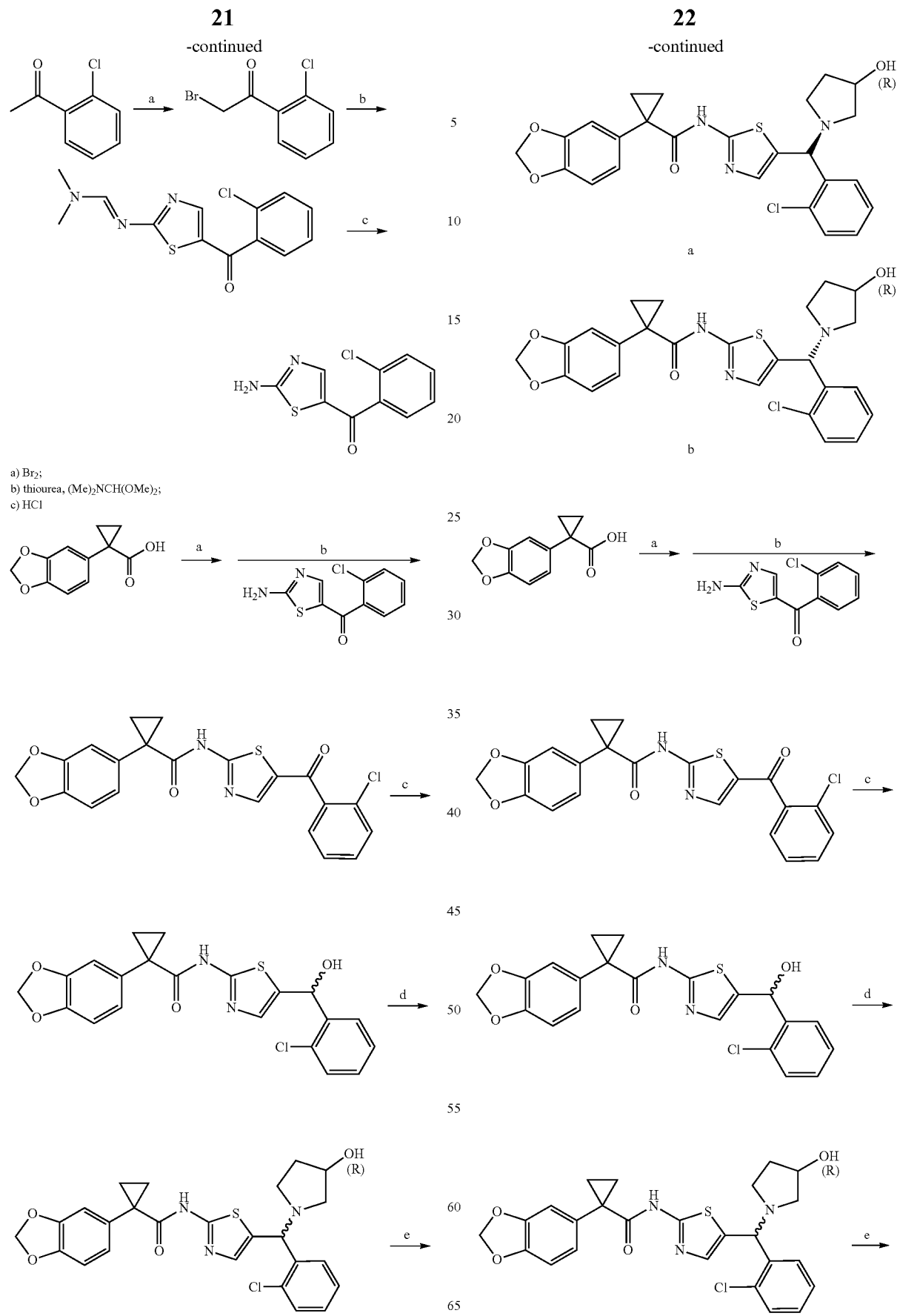
a) Br$_2$;
b) thiourea, (Me)$_2$NCH(OMe)$_2$;
c) HCl

23
-continued
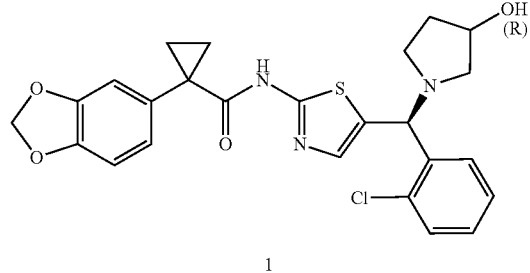
1
24
-continued
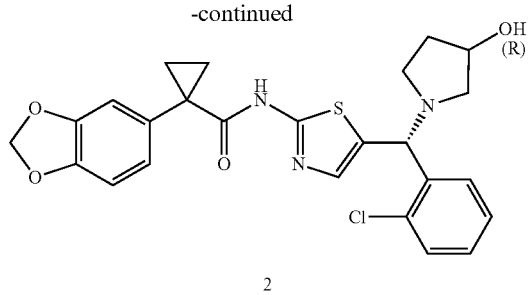
2
a) SOCl₂, DMF;
b) 1,4-dioxane, Et₃N;
c) NaBH₄, MeOH;
d) i) CH₃SO₂Cl, DCM, Et₃N;
   ii) (R)-pyrrolidinol;
e) chiral chromatography
Scheme II-A below illustrates another exemplary process for preparing compounds of the present invention using a chiral-auxiliary.
Scheme II-A:
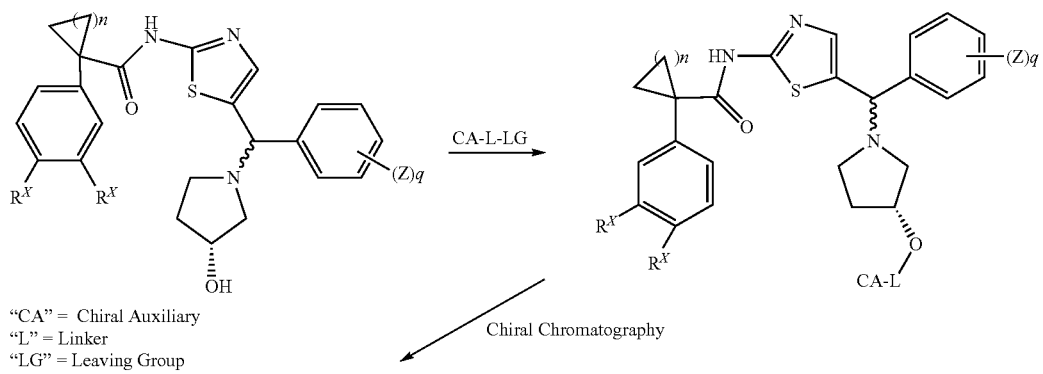
"CA" = Chiral Auxiliary
"L" = Linker
"LG" = Leaving Group
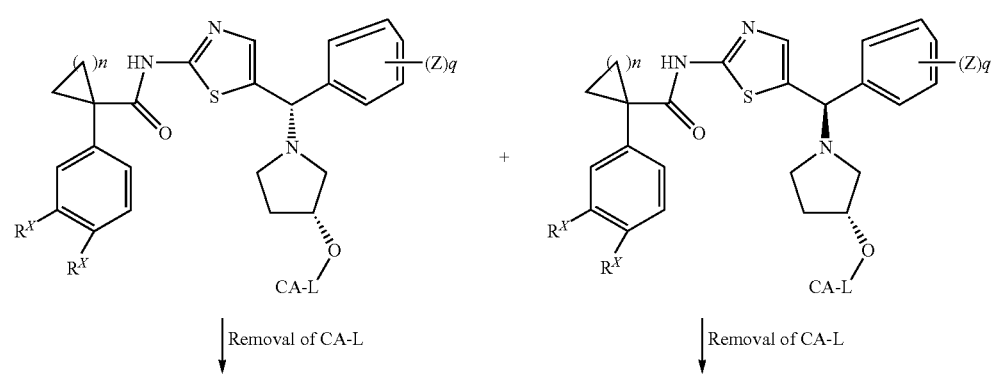
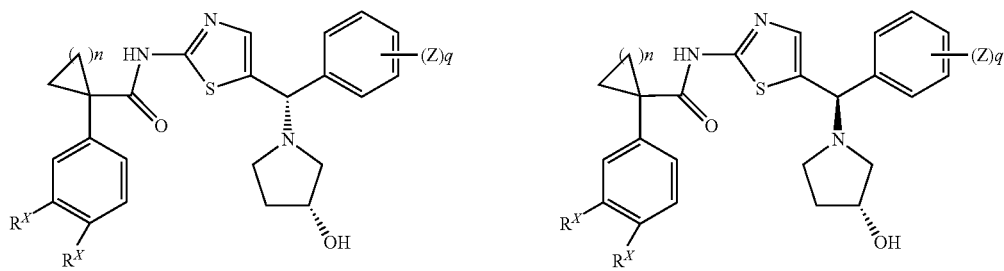

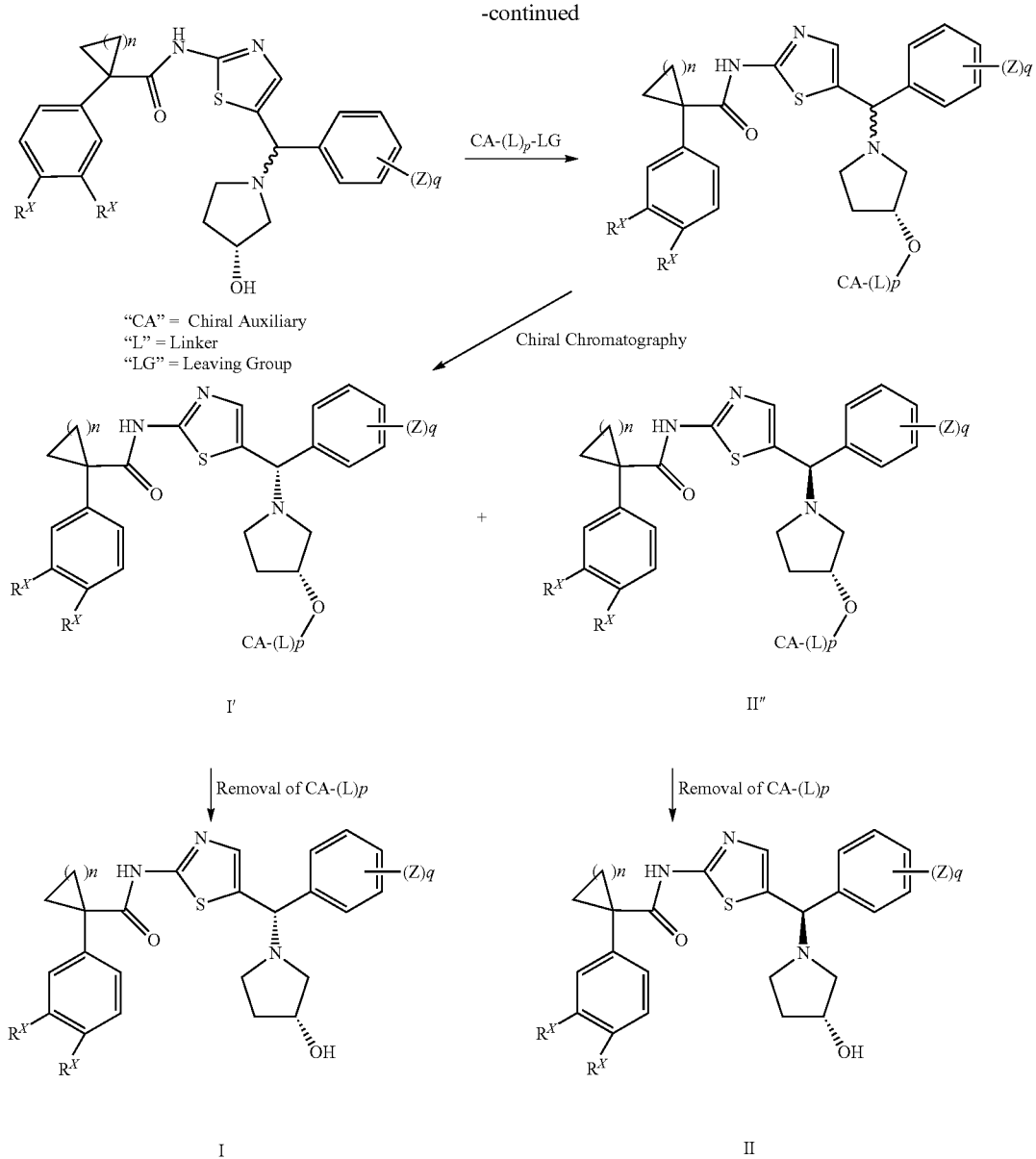
"CA" = Chiral Auxiliary
"L" = Linker
"LG" = Leaving Group
Scheme II-B below illustrates a process for preparing an exemplary compound of the present invention using a chiral auxiliary.
Scheme II-B:
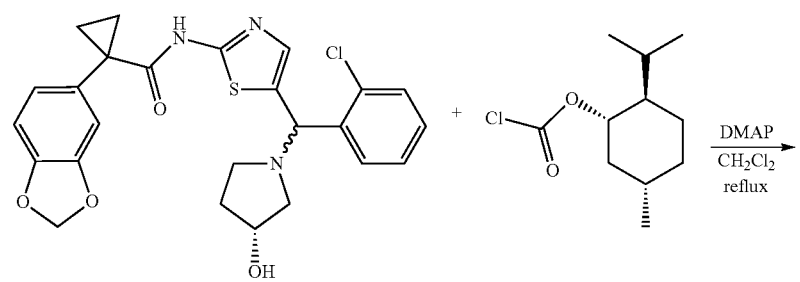

-continued
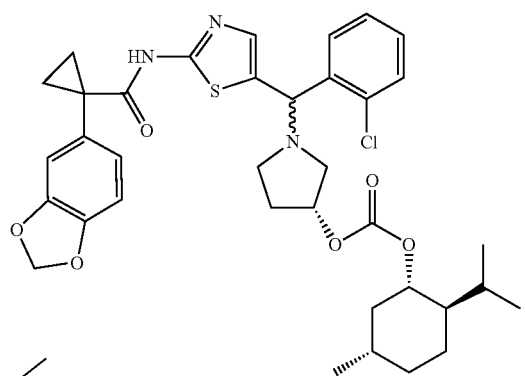
Chiral Chromatography
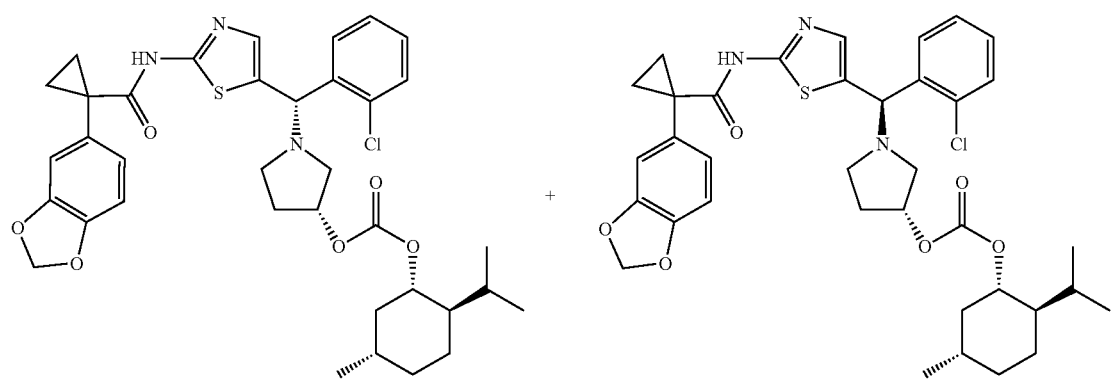
KOH, MeOH
KOH, MeOH
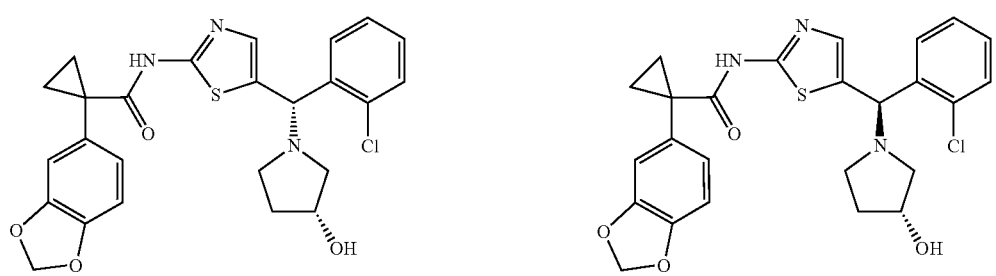
Chiral Chromatography 29
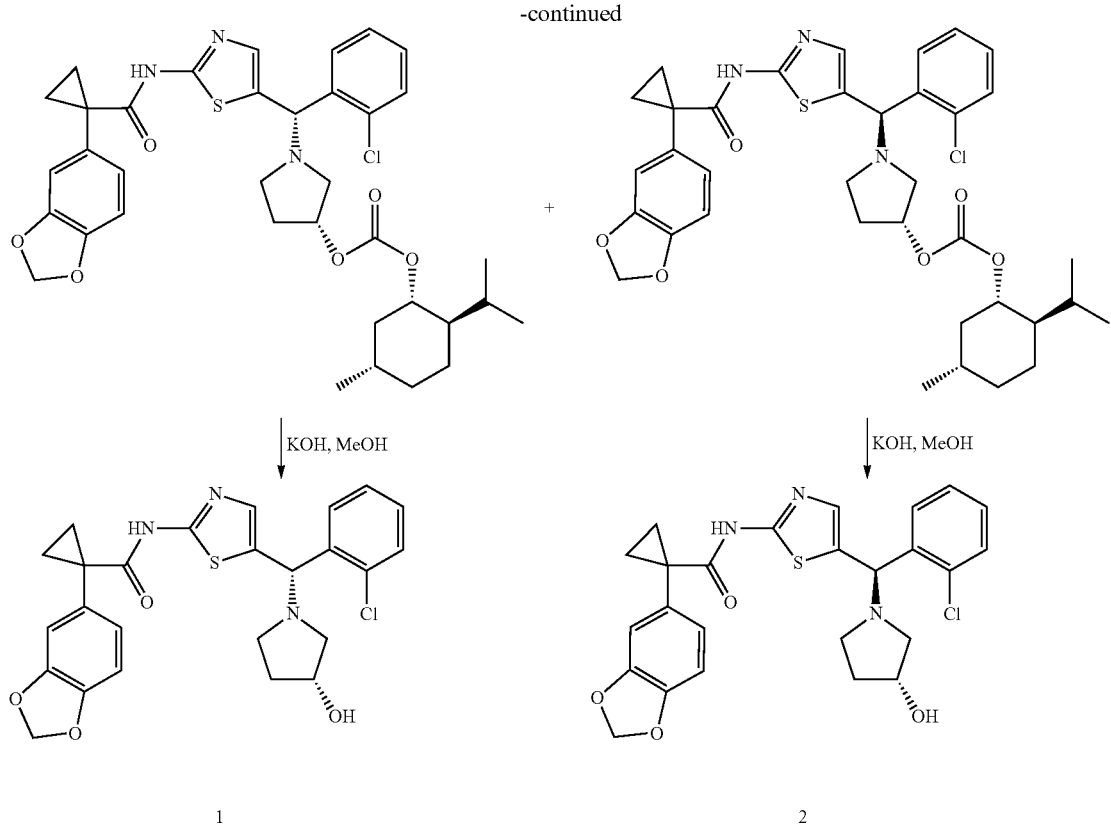
1
2
Scheme III below illustrates another process for preparing a compound of the present invention.
Scheme III, Step A:
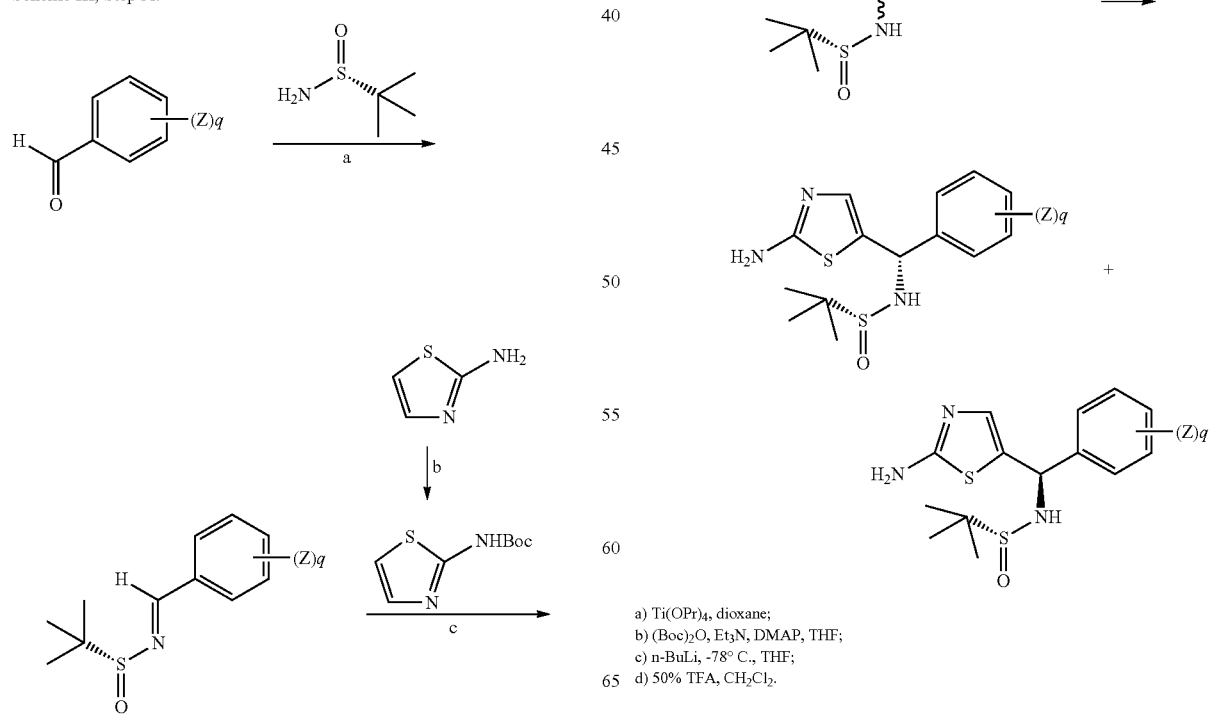
a) Ti(OPr)₄, dioxane;
b) (Boc)₂O, Et₃N, DMAP, THF;
c) n-BuLi, -78° C., THF;
d) 50% TFA, CH₂Cl₂.

Scheme III, Step B:
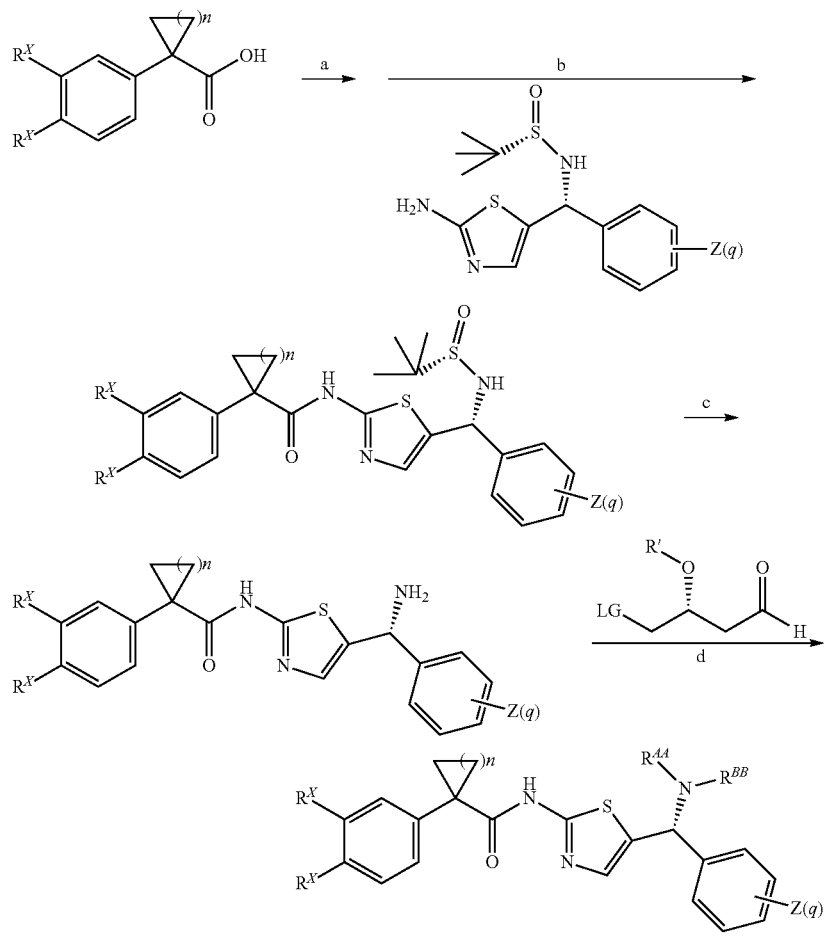
a) SOCl₂, DMF, 60° C.;
b) Et₃N, CH₂Cl₂;
c) HCl in dioxane, CH₃OH;
d) NaBH₄ (LG = leaving group).
Scheme III, Step C:
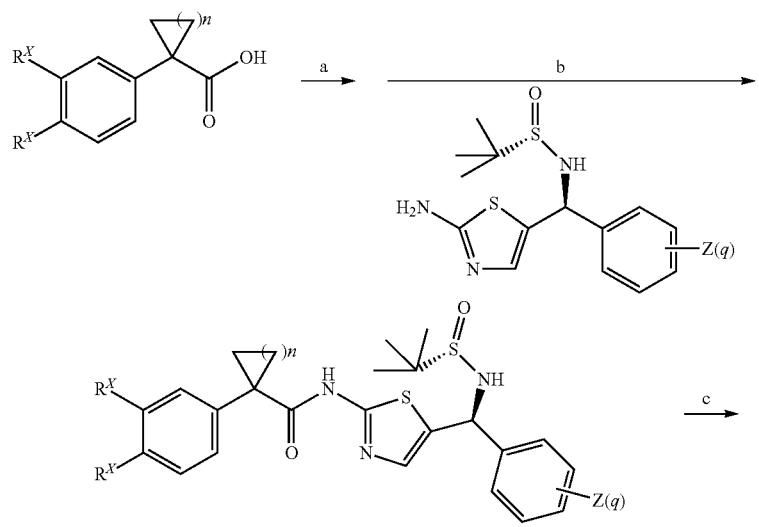

-continued

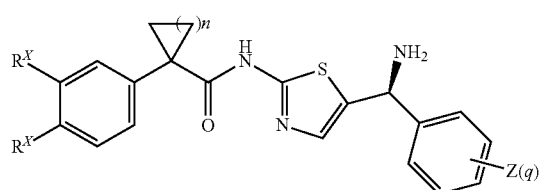 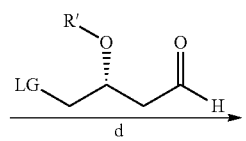

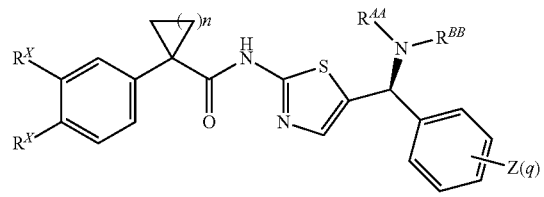

a) SOCl₂, DMF, 60° C.;
b) Et₃N, CH₂Cl₂;
c) HCl in dioxane, CH₃OH;
d) NaBH₄ (LG = leaving group).

Further illustrative examples for preparing compounds of the present invention are recited below.

5. Uses, Formulation and Administration

Pharmaceutically Acceptable Compositions

As discussed above, the present invention provides compounds that are useful as modulators of CFTR and thus are useful in the treatment of disease, disorders or conditions such as Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an ATP-Binding Cassette Transporters.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺(C₁₋₄alkyl)₄ salts.

This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR, the method comprising administering a composition comprising a compound of formula (I) to a subject, preferably a mammal, in need thereof.

In certain preferred embodiments, the present invention provides a method of treating cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1'-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher-disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluyysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility.

The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of CFTR. Thus, without wishing to be bound by any particular theory, the compounds and compositions are particularly useful for treating or lessening the severity of a disease, condition, or disorder where hyperactivity or inactivity of CFTR is implicated in the disease, condition, or disorder. When hyperactivity or inactivity of an CFTR is implicated in a particular disease, condition, or disorder, the disease, condition, or disorder may also be referred to as a "CFTR-mediated disease, condition or disorder". Accordingly, in another aspect, the present invention provides a method for treating or lessening the severity of a disease, condition, or disorder where hyperactivity or inactivity of an CFTR is implicated in the disease state.

The activity of a compound utilized in this invention as a modulator of an CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR activity in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of formula (I). The term "functional ABC transporter" as used herein means an CFTR that is capable of transport activity.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (S Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a CFTR or a fragment thereof in a biological sample in vitro or in vivo comprising (i) a composition comprising a compound of formula (I) or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Example 1

1-(Benzo[d][1,3]dioxol-6-yl)-N-(5-((R)-(2-chlorophenyl)((R)-3-hydroxypyrrolidin-1-yl)methyl) thiazol-2-yl)cyclopropanecarboxamide (2) hydrochloride and 1-(benzo[d][1,3]dioxol-6-yl)-N-(5-((S)-(2-chlorophenyl)((R)-3-hydroxypyrrolidin-1-yl) methyl)thiazol-2-yl)cyclopropanecarboxamide (1) hydrochloride

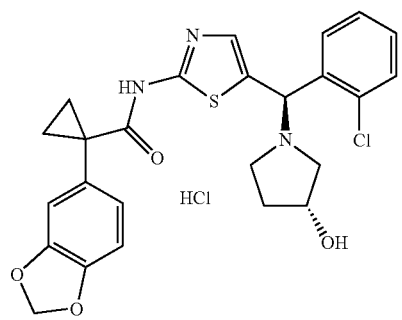

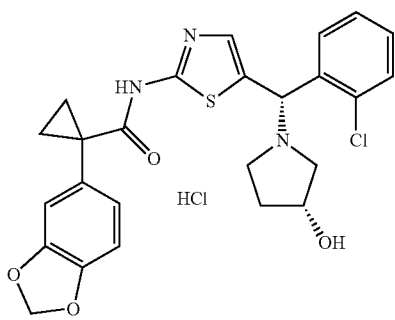

1-Benzo[1,3]dioxol-5-yl-cyclopropanecarboxylic acid

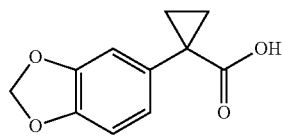

A mixture of benzo[1,3]dioxole-5-acetonitrile (5.10 g 31.7 mmol), 1-bromo-2-chloro-ethane (9.000 mL 108.6 mmol), and benzyltriethylammonium chloride (BTEAC, 0.181 g 0.795 mmol) was heated to 70° C. and then 50% (wt./wt.) aqueous sodium hydroxide (26 mL) was slowly added. The reaction was stirred at 70° C. for 24 hours and then heated to reflux (130° C. bath temperature) for 72 hours. The dark brown/black reaction mixture was diluted with water (400 mL) and extracted twice with equal volumes ethyl acetate and dichloromethane. The basic aqueous solution was acidified with concentrated hydrochloric acid to pH less than one and the precipitate was filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 25.4 mmol, 80.1%). ESI-MS m/z calc. 206.1. found 207.1 (M+1)$^+$. Retention time of 2.37 minutes. $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H).

2-Bromo-1-(chloro-phenyl)-ethanone

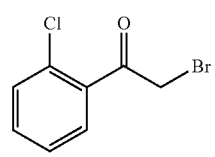

Bromine (3.8 mL, 65 mmol) was added dropwise to a solution of 1-(2-chloro-phenyl)-ethanone (10 g. 65 mmol) in acetic acid (75 mL) at 0° C. The mixture was then warmed to room temperature and stirred overnight. The mixture was evaporated to dryness and used in the next step without further purification.

N'-[5-(2-Chloro-benzoyl)-thiazol-2-yl]-N,N-dimethyl-formamidine

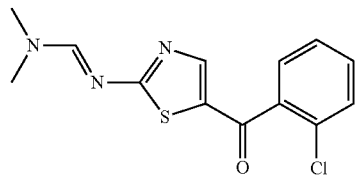

A mixture of thiourea (4.95 g, 65.0 mmol) and dimethoxymethyl-dimethyl-amine (23.2 g, 195 mmol) in methanol (80 mL) was heated to reflux for 30 minutes. After allowing the mixture to cool, triethylamine (19.8 g, 195 mmol) and a solution of 2-bromo-1-(chloro-phenyl)-ethanone (crude from last step) in methanol (50 mL) were added. The mixture was heated to reflux for 4 hours. The solvent was removed and the residue was used directly in the next procedure.

(2-Amino-thiazol-5-yl)-(2-chloro-phenyl)-methanone

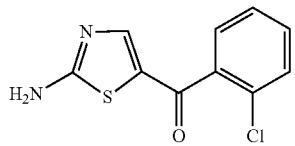

The crude N'-[5-(2-chloro-benzoyl)-thiazol-2-yl]-N,N-dimethyl-formamidine was dissolved in 10% HCl (150 mL) and heated to 70° C. for 4 hours. The precipitate was filtered, washed with ether, and then suspended in a 10% sodium carbonate solution (250 mL). The suspension was stirred for 1 hour and the precipitate was filtered, washed with ether, and dried in air to give (2-amino-thiazol-5-yl)-(2-chloro-phenyl)-methanone as a brown solid (8.5 g, 36 mmol, 55% from 1-(2-chloro-phenyl)-ethanone). $^1$H NMR (400 MHz, DMSO-d$_6$) δ 7.27 (s, 1H), 7.41-7.58 (m, 4H), 8.37 (s, 2H). ESI-MS m/z calc. 238.0. found; 239.3 (M+1)$^+$.

1-Benzo[1,3]dioxol-5-yl-cyclopropanecarboxylic acid [5-(2-chloro-benzoyl)-thiazol-2-yl]-amide

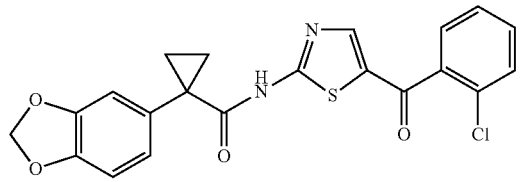

1-Benzo[1,3]dioxol-5-yl-cyclopropanecarboxylic acid (1.29 g, 6.28 mmol) was placed in an oven-dried flask under nitrogen. Thionyl chloride (3 mL) and N,N-dimethylformamide (0.3 mL) were added and the solution was allowed to stir for 2 hours. The excess thionyl chloride was removed under vacuum and the resulting solid was suspended in 30 mL of anhydrous 1,4-dioxane containing triethylamine (1.77 mL, 12.6 mmol). (2-Amino-thiazol-5-yl)-(2-chloro-phenyl)- methanone (1.50 g, 6.28 mmol) suspended in 10 mL of anhydrous 1,4-dioxane was slowly added to this suspension. The resulting suspension was allowed to stir for 20 minutes. The mixture was filtered and then the filtrate was evaporated to dryness. The crude product was dissolved in 50 mL of dichloromethane and washed three times with 50 mL of 1N HCl, saturated aqueous sodium bicarbonate, and saturated aqueous sodium chloride. The organic layer was then dried over sodium sulfate and evaporated to dryness to yield the product as a beige solid (1.51 g, 3.54 mmol, 56.4%). $^1$H NMR (400 MHz, DMSO-$d_6$) δ 1.20-1.24 (m, 2H), 1.54-1.57 (m, 2H), 6.01 (s, 2H), 6.88 (d, J=1.3 Hz, 2H), 6.98 (s, 1H), 7.48-7.52 (m, 1H), 7.56-7.60 (m, 3H), 7.77 (s, 1H), 11.98 (s, 1H). ESI-MS m/z calc. 426.0. found; 427.3 (M+1)$^+$; Retention time 3.46 minutes.

1-(Benzo[d][1,3]dioxol-6-yl)-N-(5-((2-chlorophenyl)(hydroxy)methyl)thiazol-2-yl)cyclopropanecarboxamide

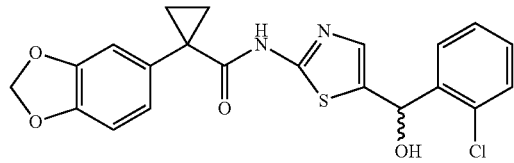

1-Benzo[1,3]dioxol-5-yl-cyclopropanecarboxylic acid [5-(2-chloro-benzoyl)-thiazol-2-yl]-amide (1.0 g, 2.3 mmol) was suspended in 150 mL of anhydrous methanol. Sodium borohydride (1.3 g, 35 mmol) was slowly added and the resulting pale yellow solution was allowed to stir for 1 hour at room temperature. The crude product was evaporated to dryness and then dissolved in a minimum of ethyl acetate. The organic was washed three times with an equal volume of 1N hydrochloric acid, saturated aqueous sodium bicarbonate, and saturated aqueous sodium chloride. The organic layer was then dried over sodium sulfate, filtered, and evaporated to dryness to yield the product as a beige solid (0.64 g, 1.5 mmol, 63%). $^1$H NMR (400 MHz, DMSO-$d_6$) δ 1.10-1.14 (m, 2H), 1.41-1.45 (m, 2H), 6.00 (s, 2H), 6.14 (s, 1H), 6.86 (d, J=1.0 Hz, 2H), 6.95 (t, J=1.0 Hz, 1H), 7.14 (d, J=0.6 Hz, 1H), 7.29-7.34 (m, 1H), 7.38-7.43 (m, 2H), 7.71 (d, J=7.5 Hz, 1H), 10.93 (s, 1H) ESI-MS m/z calc. 428.1. found; 429.5 (M+1)$^+$ Retention time 3.17 minutes.

1-(Benzo[d][1,3]dioxol-5-yl)-N-(5-((2-chlorophenyl)((R)-3-hydroxypyrrolidin-1-yl)methyl)thiazol-2-yl)cyclopropanecarboxamide

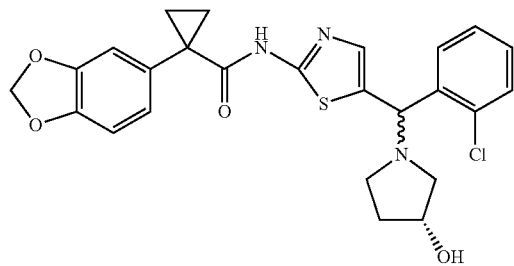

1-Benzo[1,3]dioxol-5-yl-cyclopropanecarboxylic acid [5-[(2-chloro-phenyl)-hydroxy-methyl]-thiazol-2-yl]-amide (0.500 g, 1.17 mmol) was placed in 10 mL of anhydrous dichloromethane containing triethylamine (984 μL, 7.02 mmol). The mixture was cooled to 0° C. and methanesulfonyl chloride (364 μL, 4.68 mmol) was added, immediately followed by (R)-pyrrolidin-3-ol (945 μL, 11.7 mmol) and the solution was allowed to stir for 10 minutes at room temperature. The crude product was washed three times with an equal volume of a saturated aqueous solution of sodium bicarbonate, followed by a saturated aqueous solution of sodium chloride. The organic layer was then dried over sodium sulfate and evaporated to dryness. The crude mixture was purified by column chromatography (20-90% ethyl acetate in hexanes on silica gel) to yield the product as a white solid (194.2 mg, 0.390 mol, 33.3%). $^1$H NMR (400 MHz, DMSO-$d_6$) δ 1.09-1.15 (m, 2H), 1.41-1.44 (m, 2H), 1.54-1.63 (m, 1H), 1.93-2.77 (m, 5H), 4.20 (s, 1H), 4.72-4.77 (m, 1H), 4.96 (d, J=7.0 Hz, 1H), 6.00 (s, 2H), 6.85 (d, J=0.9 Hz, 2H), 6.95 (s, 1H), 7.24-7.29 (m, 1H), 7.37-7.43 (m, 3H), 7.76-7.80 (m, 1H), 11.03 (s, 1H). ESI-MS m/z calc. 497.1. found; 498.1 (M+1)$^+$; Retention time 2.36 minutes.

1-(Benzo[d][1,3]dioxol-5-yl)-N-(5-((2-chlorophenyl)((R)-3-hydroxypyrrolidin-1-yl)methyl)thiazol-2-yl)cyclopropanecarboxamide hydrochloride

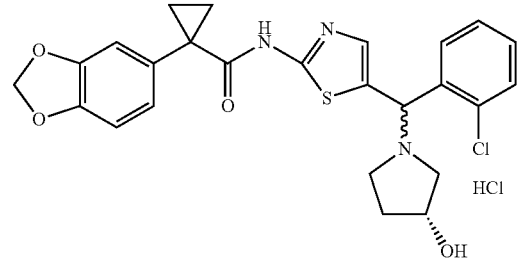

A solution of HCl in ether (0.1556 mL, 0.3112 mmol, 1M) was slowly added to a stirred solution of 1-(benzo[d][1,3]dioxol-5-yl)-N-(5-((2-chlorophenyl)((R)-3-hydroxypyrrolidin-1-yl)methyl)thiazol-2-yl)cyclopropanecarboxamide (0.1550 g, 0.3112 mmol) in 100 mL of anhydrous dichloromethane. The solution was evaporated to dryness to give the pure product (0.1654 g, 0.3095, 99.45%). ESI-MS m/z calc. 497.1. found; 498.1 (M+1)$^+$; Retention time 5.74 minutes.

1-(Benzo[d][1,3]dioxol-6-yl)-N-(5-((S)-(2-chlorophenyl)((R)-3-hydroxypyrrolidin-1-yl)methyl)thiazol-2-yl)cyclopropanecarboxamide (1) hydrochloride and 1-(Benzo[d][1,3]dioxol-6-yl)-N-(5-((R)-(2-chlorophenyl)((R)-3-hydroxypyrrolidin-1-yl)methyl)thiazol-2-yl)cyclopropanecarboxamide (2) hydrochloride

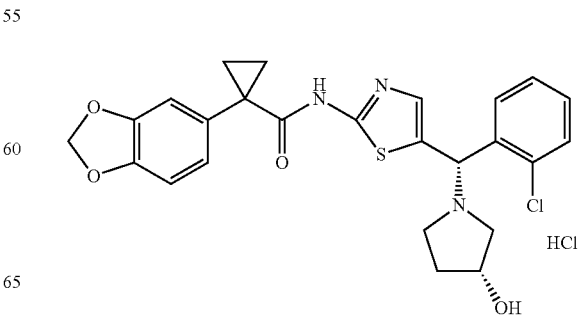

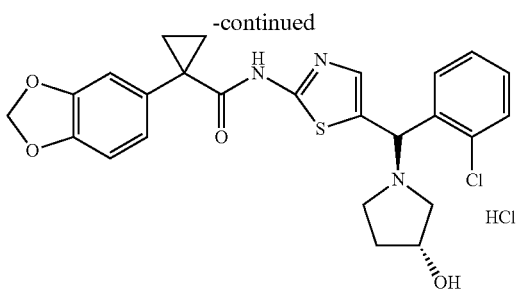

1-(Benzo[d][1,3]dioxol-6-yl)-N-(5-((2-chlorophenyl)((R)-3-hydroxypyrrolidin-1-yl)methyl)thiazol-2-yl)cyclopropanecarboxamide hydrochloride prepared above was separated using utilizing a Chiralpak AS-H 4.6 mm×250 mm column from Chiral Technologies.

20-25 µL of a 2 mg/mL solution of 1-(benzo[d][1,3]dioxol-6-yl)-N-(5-((2-chlorophenyl)((R)-3-hydroxypyrrolidin-1-yl)methyl)thiazol-2-yl)cyclopropanecarboxamide hydrochloride in methanol was injected onto the Chiralpak AS-H column and was eluted with a mixture of 10% of a 50/50 (v/v) mixture of ethanol and methanol in hexanes at 1.5 mL/min.

The first eluting product under these conditions had a retention time of 8.2 min (Chiralpak AS-H column). This product had a retention time 14.5 min. on a Chiralpak OJ-H 4.6 mm×250 mm column (25% of a 50/50 (v/v) mixture of ethanol and methanol in hexanes at 1.0 mL/min.)

The second product eluted at 9.6 min using a Chiralpak AS-H column. This second product had a retention time of 10.9 min. on a Chiralpak OJ-H 4.6 mm×250 mm column (25% of a 50/50 (v/v) mixture of ethanol and methanol in hexanes at 1.0 mL/min.)

Example 2

(R)-1-((2-(1-(Benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate

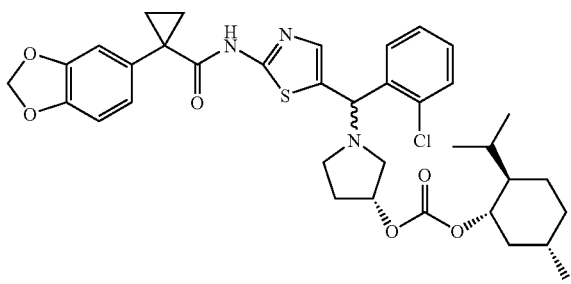

1-(Benzo[d][1,3]dioxol-5-yl)-N-(5-((2-chlorophenyl)((R)-3-hydroxypyrrolidin-1-yl)methyl)thiazol-2-yl)cyclopropanecarboxamide (3.00 g, 6.02 mmol) was suspended in 200 mL of anhydrous dichloromethane containing N,N-dimethylpyridin-4-amine (2.20 g, 18.0 mmol). (1S,2R,5S)-2-Isopropyl-5-methylcyclohexyl chloroformate (1.91 mL, 9.00 mmol) was slowly added to the suspension and the resulting mixture was heated to reflux for 16 hours. The resulting pale yellow solution was allowed to cool to room temperature, diluted with 20 mL of methanol, and then evaporated to dryness. The crude reaction mixture was separated on 330 g of silica gel utilizing a gradient of 0-5% methanol in dichloromethane to yield the pure product as a pale yellow solid (2.0087 g, 2.9529 mmol, 49.1%). ESI-MS m/z calc. 679.3. found; 680.5 (M+1)$^+$; Retention time 3.88 minutes.

(R)-1-((S)-(2-(1-(Benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate and (R)-1-((R)-(2-(1-(benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate

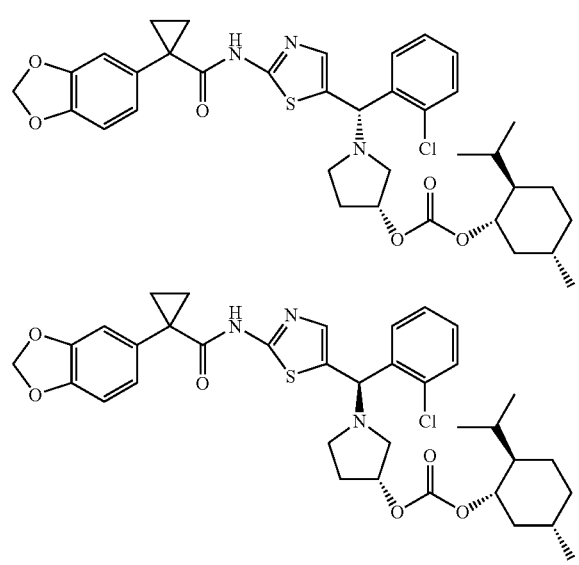

(R)-1-(2-(1-(Benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate prepared above was separated utilizing a Chiralpak AD 21 mm×250 mm column from Chiral Technologies. 1 mL of a 30 mg/mL solution of compound prepared above in isopropanol was injected onto the Chiralpak AD column and was eluted with a mixture of 7.5% isopropanol in heptane at 15 mL/min. The first eluting product ((R)-1-((S)-(2-(1-(benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate) had a retention time of 14.4 min. (Chiralpak AD column); $^1$H NMR (400 MHz, CD$_3$OD) δ 0.79 (d, J=7.0 Hz, 3H), 0.85-1.84 (m, 18H), 1.86-2.04 (m, 3H), 2.23-2.34 (m, 1H), 2.43-2.51 (m, 1H), 2.62-2.69 (m, 1H), 2.73-2.78 (m, 2H), 4.45-4.54 (m, 1H), 5.04-5.08 (m, 1H), 5.12 (s, 1H), 5.99 (s, 2H), 6.82 (d, J=8.5 Hz, 1H), 6.93-6.97 (m, 2H), 7.25 (t, J=6.8 Hz, 1H), 7.32 (s, 1H), 7.34-7.40 (m, 2H), 7.85 (dd, J=8.1, 1.6 Hz, 1H). ESI-MS m/z calc. 679.3. found; 680.5 (M+1)$^+$; Retention time 3.91 minutes.

The second eluting product ((R)-1-((R)-(2-(1-(benzo[d][1,3]dioxol-6-yl)cyclopropanecarboxamido)thiazol-5-yl)(2-chlorophenyl)methyl)pyrrolidin-3-yl (1S,2R,5S)-2-isopropyl-5-methylcyclohexyl carbonate) had a retention time of 28.6 min (Chiralpak AD column). ESI-MS m/z calc. 679.3. found; 680.5 (M+1)$^+$; Retention time 3.86 minutes.

1-(Benzo[d][1,3]dioxol-6-yl)-N-(5-((S)-(2-chlorophenyl)((R)-3-hydroxypyrrolidin-1-yl)methyl)thiazol-2-yl)cyclopropanecarboxamide hydrochloride and 1-(Benzo[d][1,3]dioxol-6-yl)-N-(5-((R)-(2-chlorophenyl)((R)-3-hydroxypyrrolidin-1-yl)methyl)thiazol-2-yl)cyclopropanecarboxamide hydrochloride

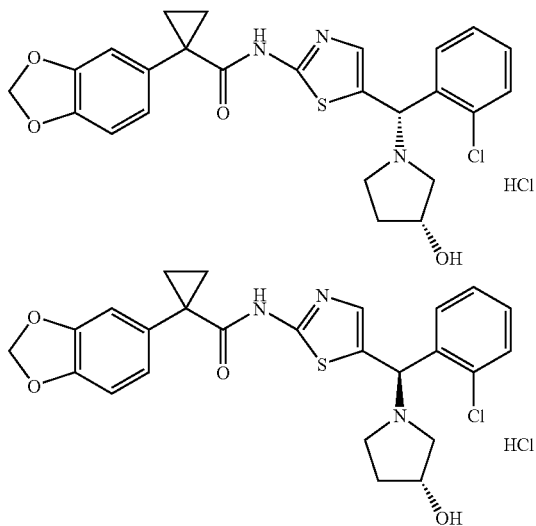

The first eluting product from previous step (1.20 g, 1.76 mmol) was stirred at room temperature in 182 mL of methanol containing (0.9153 g, 16.31 mmol) of potassium hydroxide for 4 days. The solution was then cooled to 0° C. and 16.31 mL of 1N HCl was slowly added to the reaction mixture. The resulting solution was evaporated to near dryness and then partitioned between 100 mL of dichloromethane and 100 mL of a saturated aqueous solution of sodium bicarbonate. The layers were separated and the organic layer was washed twice with and equal volume of a saturated aqueous solution of sodium bicarbonate followed by three washes with a saturated aqueous solution of sodium chloride. The organic layer was then dried over anhydrous sodium sulfate, concentrated, and purified on 120 g of silica gel utilizing a gradient of 20-100% ethyl acetate in hexanes over 40 minutes to yield the pure product as a white solid (0.70 g, 1.4 mmol). This material was then dissolved in a minimum of dichloromethane and 1.4 mL of 1M HCl in ether was added to the solution. The solution was evaporated to dryness to yield the HCl salt as a white solid (0.7818 g, 1.463 mmol, 83.1%). ESI-MS m/z calc. 497.1. found; 498.3 (M+1)+; Retention time 2.36 minutes. Retention time of this product was 14.5 min. on a Chiralpak OJ-H 4.6 mm×250 mm column (25% of a 50/50 (v/v) mixture of ethanol and methanol in hexanes at 1.0 mL/min).

$^1$H NMR (400 MHz, DMSO-d$_6$) δ (free base) 1.07-1.15 (m, 2H), 1.40-1.44 (m, 2H), 1.51-1.65 (m, 1H), 1.95-2.08 (m, 1H), 2.32-2.58 (m, 4H), 4.10-4.31 (m, 1H), 4.76 (d, J=4.3 Hz, 1H), 4.95 (s, 1H), 6.00 (s, 2H), 6.85 (s, 2H), 6.95 (d, J=0.9 Hz, 1H), 7.26 (t, J=7.6 Hz, 1H), 7.34-7.44 (m, 3H), 7.78 (d, J=7.7 Hz, 1H), 11.02 (s, 1H).

The second eluting product from previous step (0.1018 g, 0.1497 mmol) was stirred at room temperature in 15 mL of methanol containing (9.5 mg, 0.17 mmol) of potassium hydroxide for 3 days. An additional aliquot of potassium hydroxide was added (64.8 mg, 1.15 mmol) and the solution was allowed to stir for and additional 3 days. The solution was then cooled to 0° C. and 1.319 mL of 1N HCl was slowly added to the reaction mixture. The resulting solution was evaporated to near dryness and then partitioned between 10 mL of dichloromethane and 10 mL of a saturated aqueous solution of sodium chloride. The organic layer was then dried over anhydrous sodium sulfate, concentrated, and purified on 12 g of silica gel utilizing a gradient of 20-100% ethyl acetate in hexanes over 40 minutes. The column was then flushed with ethylacetate containing 2.5% triethylamine. The pure fractions were combined and evaporated to dryness to yield the pure product as a white solid (15.7 mg, 0.0315 mmol). This material was then dissolved in a minimum of dichloromethane and 0.0315 mL of 1 M HCl in ether was added to the solution. The solution was evaporated to dryness to yield the HCl salt as a white solid (16.8 g, 0.0315 mmol, 21.0%). ESI-MS m/z calc. 497.1. found; 498.3 (M+1)+; Retention time 2.42 minutes. Retention time 10.9 minutes on a Chiralpak OJ-H 4.6 mm×250 mm column (25% of a 50/50 (v/v) mixture of ethanol and methanol in hexanes at 1.0 mL/min.)

(R)-N-(2-Chlorobenzylidene)-1,1-dimethylethylsulfinamide

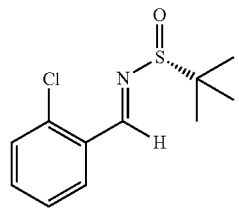

To a stirred anhydrous dioxane (500 mL) was added 2-chlorobenzaldehyde (34.8 g, 247.5 mmol) and the solution was cooled down to 0° C. in an ice bath. A solution of (R)-2-methylpropanesulfinamide (30.0 g, 247.5 mmol) in anhydrous dioxane (100 mL) was added to the aldehyde solution. Ti(OPr)$_4$ (105.5 g, 371.3 mmol) was then slowly added to the solution while stirring at 0° C. The reaction mixture was allowed to warm up to 25° C., stirred at 25° C. for 18 h, quenched with NaHCO$_3$ and then filtered through a short plug of Celite using EtOAc. The organic layer was separated from the aqueous layer and dried over Na$_2$SO$_4$ and concentrated. The crude product was purified by column chromatography (0-25% EtOAc/Hexane) to provide (R)-N-(2-chlorobenzylidene)-1,1-dimethylethylsulfinamide as a yellow liquid (45.1 g, 75%). $^1$H-NMR (400 MHz, CDCl3) δ 9.05 (s, 1H), 8.06 (dd, J=7.9, 1.1 Hz, 1H), 7.47-7.41 (m, 2H), 7.37-7.33 (m, 1H), 1.28 (s, 9H). HPLC ret. time 3.45 min, 10-99% CH$_3$CN, 5 min run; ESI-MS 244.3 m/z (MH+).

tert-Butyl thiazol-2-ylcarbamate

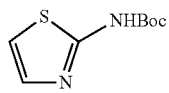

To a solution of 2-aminothiazole (20.0 g, 199.7 mmol) and (Boc)$_2$O (48.0 g, 219.7 mmol) in anhydrous THF (100 mL) were added DMAP (20 mg) and Et$_3$N (36.0 mL, 260.0 mmol). The reaction mixture was stirred at 25° C. for 18 h, diluted with CH$_2$Cl$_2$ and washed with 0.1 N HCl (×1), brine (×1) and H₂O (×1). The organic layer was separated from the aqueous layer, dried over Na₂SO₄ and concentrated. The crude product was purified by column chromatography (0-40% EtOAc/Hexane) to provide tert-butyl thiazol-2-ylcarbamate as a white solid (20.7 g, 72%). ¹H-NMR (400 MHz, CDCl₃) δ 11.44 (s, 1H), 7.38 (d, J=3.6 Hz, 1H), 6.89 (d, J=3.6 Hz, 1H), 1.58 (s, 9H). HPLC ret. time 2.61 min, 10-99% CH₃CN, 5 min run; ESI-MS 145.1 m/z (MH⁺).

(R)-N-(1-((2-t-butoxylcarbonylamino)thiazol-5-yl)-1-(2-chlorophenyl)-methyl)-1,1-dimethylethylsulfinamide

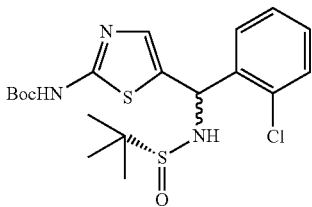

A solution of tert-butyl thiazol-2-ylcarbamate (15.0 g, 75.0 mmol) in anhydrous THF (175 mL) was stirred and cooled down to −78° C. To this solution was slowly added n-BuLi (2.5 M in hexane: 60.0 mL, 150.0 mmol). Upon completion of n-BuLi addition, the mixture was allowed to warm up to −40° C., maintained at −40° C. for 1 h and then cooled down to −78° C. A solution of (R)-N-(2-chlorobenzylidene)-1,1-dimethylethylsulfinamide (10.0 g, 41.0 mmol) in anhydrous THF (175 mL) previously cooled to −78° C. was slowly added to the above solution via canulation. The reaction was kept at −78° C. for 0.5 h, allowed to warm up to room temperature and stirred at room temperature for 2 h. The reaction was then quenched with aqueous NH₄Cl, and the crude product was extracted with EtOAC (×3). The combined organic layers were dried over Na₂SO₄ and concentrated. The crude product was purified by column chromatography (0-80% EtOAc/Hexane) to provide a diastereomeric mixture of (R)-N-(1-((2-t-butoxylcarbonylamino)thiazol-5-yl)-1-(2-chlorophenyl)-methyl)-1,1-dimethylethylsulfinamide as a yellow solid (15.1 g, 83%) that was used directly in the next step.

(R)-N-(S)-1-(2-Aminothiazol-5-yl)-1-(2-chlorophenyl)methyl)-1,1-dimethylethylsulfinamide and (R)-N-(R)-1-(2-aminothiazol-5-yl)-1-(2-chlorophenyl)methyl)-1,1-dimethylethylsulfinamide

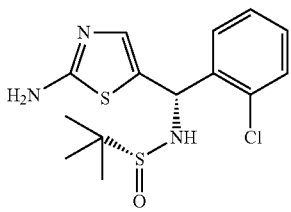

To a solution of (R)-N-(1-((2-t-butoxylcarbonylamino)thiazol-5-yl)-1-(2-chlorophenyl)-methyl)-1,1-dimethylethylsulfinamide (7.0 g, 15.8 mmol) in CH₂Cl₂ (28 mL) was added trifluoroacetic acid (28 mL). The reaction was stirred at room temperature for 3.5 h. The trifluoroacetic acid and CH₂Cl₂ were removed under vacuum. The crude product was re-dissolved in CH₂Cl₂, washed with aqueous NaHCO₃ (20 mL×2) and water (20 mL×1), dried over Na₂SO₄ and concentrated. The crude product was purified by column chromatography (0-5% EtOH/EtOAc) to provide (R)-N-(S)-1-(2-aminothiazol-5-yl)-1-(2-chlorophenyl)methyl)-1,1-dimethylethylsulfinamide and (R)-N-(R)-1-(2-aminothiazol-5-yl)-1-(2-chlorophenyl)methyl)-1,1-dimethylethylsulfinamide.

(R)-N-(S)-1-(2-aminothiazol-5-yl)-1-(2-chlorophenyl)methyl)-1,1-dimethylethylsulfinamide: yellow solid, 4.3 g (79%). ¹H-NMR (400 MHz, CDCl₃) δ 7.53 (dd, J=7.6, 1.8 Hz, 1H), 7.38 (dd, J=7.7, 1.5 Hz, 1H), 7.32 (td, J=7.5, 1.6 Hz, 1H), 7.27 (td, J=7.5, 1.8 Hz, 1H), 6.84 (d, J=0.7 Hz, 1H), 6.17 (s, 2H), 6.07 (d, J=4.5 Hz, 1H), 4.17 (d, J=4.6 Hz, 1H), 1.26 (s, 9H). HPLC ret. time 2.11 min, 10-99% CH₃CN, 5 min run; ESI-MS 344.0 m/z (MH⁺).

(R)-N-(R)-1-(2-Aminothiazol-5-yl)-1-(2-chlorophenyl)methyl)-1,1-dimethylethylsulfinamide: yellow solid, 596 mg, (11%). HPLC ret. time 2.35 min, 10-99% CH₃CN, 5 min run; ESI-MS 344.0 m/z (MH⁺).

(S)-N-(5-((R)-t-butylsulfinylamino(2-chlorophenyl)methyl)thiazol-2-yl)-1-(benzo[d][1,3]dioxol-5-yl)cyclopropanecarboxamide

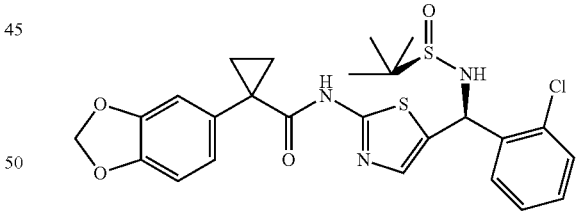

To 1-(benzo[d][1,3]dioxol-5-yl)cyclopropanecarboxylic acid (2.16 g, 10.5 mmol) was slowly added SOCl₂ (2.3 mL, 31.5 mmol) followed by DMF (3 drops). The reaction mixture was heated at 60° C. for 0.5 h. The excess SOCl₂ was removed under vacuum. The acid chloride (10.5 mmol) was then dissolved in anhydrous CH₂Cl₂ (16 mL) and was slowly added to a cold (temperature ~0° C.) solution of (R)-N-(S)-1-(2-aminothiazol-5-yl)-1-(2-chlorophenyl)methyl)-1,1-dimethylethylsulfinamide (3.6 g, 10.5 mmol) and Et₃N (7.33 mL, 52.6 mmol) in anhydrous CH₂Cl₂ (16 mL). The reaction mixture was stirred at 25° C. for 18 h, diluted with CH₂Cl₂ and washed with 1 N HCl (50 mL×2), NaHCO₃ (50 mL×1) and brine (50 mL×1). The organic layer was separated from the aqueous layer, dried over Na₂SO₄ and concentrated. The crude product was purified by column chromatography (0-80% EtOAc/Hexane) to provide (S)-N-(5-((R)-t-butylsulfinylamino-(2-chlorophenyl)methyl)thiazol-2-yl)-1-(benzo[d][1,3]dioxol-5-yl)cyclopropanecarboxamide as a yellow solid (4.7 g, 84%). $^1$H-NMR (400 MHz, CDCl$_3$) δ 8.52 (s, 1H), 7.60 (dd, J=7.7, 1.7 Hz, 1H), 7.35 (dd, J=7.8, 1.4 Hz, 1H), 7.32 (dd, J=7.5, 1.4 Hz, 1H), 7.29 (d, J=0.7 Hz, 1H), 7.23 (dd, J=7.6, 1.7 Hz, 1H), 6.89 (dd, J=7.9, 1.8 Hz, 1H), 6.86 (d, J=1.6 Hz, 1H), 6.81 (d, J=7.9 Hz, 6.21 (d, J=4.0 Hz, 1H), 6.01 (s, 2H), 3.93 (d, J=4.0 Hz, 1H), 1.75-1.66 (m, 2H), 1.27 (s, 9H), 1.22 (t, J=3.3 Hz, 2H). HPLC ret. time 3.52 min, 10-99% CH$_3$CN, 5 min run; ESI-MS 532.0 m/z (MH$^+$).

(S)-N-(5-(Amino(2-chlorophenyl)methyl)thiazol-2-yl)-1-(benzo[d][1,3]dioxol-5-yl)cyclopropanecarboxamide

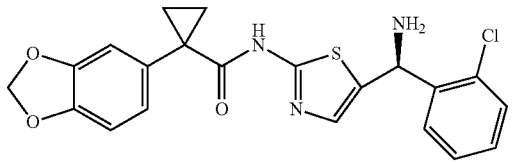

To a solution of (S)-N-(5-((R)-t-butylsulfinylamino-(2-chlorophenyl)methyl)thiazol-2-yl)-1-(benzo[d][1,3]dioxol-5-yl)cyclopropane-carboxamide (11.25 g, 21.19 mmol) in MeOH (100 mL) was added 4 M HCl in dioxane (32 mL, 128 mmol). The reaction mixture was stirred at 25° C. for 1.5 h and evaporated to dryness. The crude product was dissolved in CH$_2$Cl$_2$. The organic layer was washed with aqueous NaHCO$_3$ (50 mL×2), brine (50 mL×1), dried over Na$_2$SO$_4$ and concentrated. The crude product was purified by column chromatography (0-2.5% Et$_3$N-EtOAc) to provide (S)-N-(5-(amino(2-chlorophenyl)methyl)thiazol-2-yl)-1-(benzo[d][1,3]dioxol-5-yl)cyclopropanecarboxamide (6.5 g, 72%, >99% ee). $^1$H-NMR (400 MHz, CDCl$_3$) δ 8.51 (s, 1H), 7.60 (dd, J=7.7, 1.7 Hz, 1H), 7.33 (dd, J=7.9, 1.3 Hz, 1H), 7.29-7.25 (m, 1H), 7.20 (td, J=7.6, 1.7 Hz, 1H), 7.16 (d, J=1.0 Hz, 1H), 6.89 (td, J=7.8, 1.7 Hz, 2H), 6.80 (d, J=7.9 Hz, 1H), 6.01 (s, 2H), 5.79 (s, 1H), 1.86 (bs, 2H), 1.72-1.69 (m, 2H), 1.22-1.19 (m, 2H). HPLC ret. time 2.66 min, 10-99% CH$_3$CN, 5 min run; ESI-MS 428.1 m/z (MH$^+$).

1-(Benzo[d][1,3]dioxol-5-yl)-N-(5-((S)-(2-chlorophenyl)((R)-3-dimethyl-t-butylsilylhydroxypyrrolidin-1-yl)methyl)thiazol-2-yl)cyclopropanecarboxamide

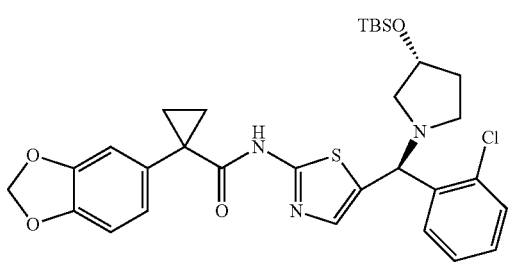

To a solution of (S)-N-(5-(amino(2-chlorophenyl)methyl)thiazol-2-yl)-1-(benzo[d][1,3]dioxol-5-yl)cyclopropanecarboxamide (214 mg, 0.5 mmol) in MeOH (2.5 mL) was added (R)-4-chloro-3-dimethyl-t-butylhydroxybutanal (142 mg, 0.6 mmol). The reaction mixture was stirred at 25° C. for 5 min before NaBH$_4$ (28 mg, 0.75 mmol) was added. Stirring was continued at 25° C. for 1 h. The reaction was diluted with H$_2$O and extracted with EtOAc. The combined organic layers was washed with brine and dried over MgSO$_4$. After the removal of solvent, the residue was purified by column chromatography (10-20% EtOAc-Hexane) to afford 1-(benzo[d][1,3]dioxol-5-yl)-N-(5-((S)-(2-chlorophenyl)((R)-3-dimethyl-t-butylsilylhydroxypyrrolidin-1-yl)methyl)thiazol-2-yl)cyclopropanecarboxamide (162 mg, 53%). $^1$H-NMR (400 MHz, CDCl$_3$) δ 8.45 (s, 1H), 7.81 (dd, J=8.1, 1.6 Hz, 1H), 7.28 (s, 1H), 7.25-7.22 (m, 2H), 7.13-7.09 (m, 1H), 6.85 (td, J=7.7, 1.7 Hz, 2H), 6.77 (d, J=7.9 Hz, 1H), 5.98 (s, 2H), 5.05 (s, 1H), 4.36-4.31 (m, 1H), 2.81 (dd, J=9.8, 6.2 Hz, 1H), 2.57-2.46 (m, 2H), 2.37 (dd, J=9.8, 4.5 Hz, 1H), 2.08-1.99 (m, 1H), 1.73-1.62 (m, 3H), 1.17 (t, J=3.9 Hz, 2H), 0.85 (s, 9H), −0.01 (d, J=6.9 Hz, 6H). HPLC ret. time 3.51 min, 10-99% CH$_3$CN, 5 min run; ESI-MS 612.41 m/z (MH$^+$).

1-(Benzo[d][1,3]dioxol-5-yl)-N-(5-((S)-(2-chlorophenyl)((R)-hydroxypyrrolidin-1-yl)methyl)thiazol-2-yl)cyclopropanecarboxamide (1)

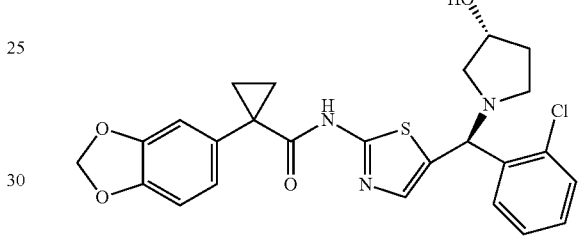

A mixture of 1-(benzo[d][1,3]dioxol-5-yl)-N-(5-((S)-(2-chlorophenyl)((R)-3-dimethyl-t-butylsilylhydroxypyrrolidin-1-yl)methyl)thiazol-2-yl)cyclopropanecarboxamide (61 mg, 0.1 mmol) and TBAF (1 M in THF, 0.6 mL, 0.6 mmol) was stirred at 25° C. for 3 h. The reaction was diluted with H$_2$O and extracted with EtOAc. The combined organic layers was washed with brine and dried over MgSO$_4$. After the removal of solvent, the residue was purified by column chromatography (10-20% EtOAc-Hexane) to afford 1-(benzo[d][1,3]dioxol-5-yl)-N-(5-((S)-(2-chlorophenyl)((R)-hydroxypyrrolidin-1-yl)methyl)thiazol-2-yl) cyclopropanecarboxamide (1) (30 mg, 62%, >99% ee). $^1$H-NMR (400 MHz, DMSO-d6) δ 11.00 (s, 1H), 7.79 (dd, J=7.8, 1.5 Hz, 1H), 7.43-7.37 (m, 3H), 7.26 (td, J=7.6, 1.4 Hz, 1H), 6.95 (s, 1H), 6.86 (d, J=0.7 Hz, 2H), 6.00 (s, 2H), 4.96 (s, 1H), 4.76 (d, J=4.4 Hz, 1H), 4.20 (ddd, J=6.6, 3.4 Hz, 1H), 2.56-2.45 (m, 2H), 2.43-2.36 (m, 2H), 2.06-1.97 (m, 1H), 1.62-1.54 (m, 1H), 1.43 (q, J=3.7 Hz, 2H), 1.14-1.09 (m, 2H). HPLC ret. time 2.85 min, 10-99% CH$_3$CN, 5 min run; ESI-MS 498.0 m/z (MH$^+$).

(R)-N-(5-((R)-t-butylsulfinylamino(2-chlorophenyl)methyl)thiazol-2-yl)-1-(benzo[d][1,3]dioxol-5-yl)cyclopropanecarboxamide

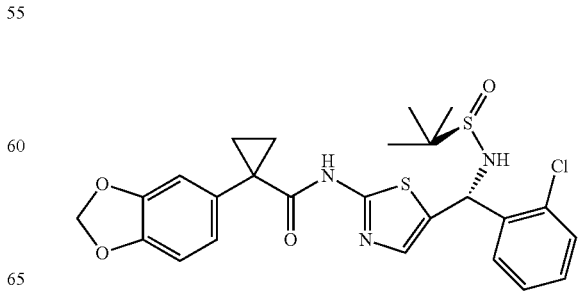

(R)-N-(5-((R)-t-butylsulfinylamino(2-chlorophenyl)methyl)thiazol-2-yl)-1-(benzo[d][1,3]dioxol-5-yl)cyclopropanecarboxamide was prepared from (R)-N-(R)-1-(2-aminothiazol-5-yl)-1-(2-chlorophenyl)methyl)-1,1-dimethylethylsulfinamide and 1-(benzo[d][1,3]dioxol-5-yl)cyclopropanecarboxylic acid using the same protocol for (S)-N-(5-((R)-t-butylsulfinylamino(2-chlorophenyl)methyl)thiazol-2-yl)-1-(benzo[d][1,3]dioxol-5-yl)cyclopropanecarboxamide. $^1$H-NMR (400 MHz, CDCl$_3$) δ 8.55 (s, 1H), 7.62 (dd, J=7.7, 1.7 Hz, 1H), 7.37 (d, J=0.7 Hz, 1H), 7.34 (dd, J=7.8, 1.4 Hz, 1H), 7.31-7.20 (m, 2H), 6.87 (td, J=8.4, 1.7 Hz, 2H), 6.81 (d, J=7.9 Hz, 1H), 6.30 (d, J=2.8 Hz, 1H), 6.01 (s, 2H), 3.74 (d, J=2.8 Hz, 1H), 1.71-1.68 (m, 2H), 1.24 (s, 9H), 0.88 (t, J=6.9 Hz, 2H). HPLC ret. time 3.59 min, 10-99% CH$_3$CN, 5 min run; ESI-MS 532.1 m/z (MH$^+$).

(R)-N-(5-(Amino(2-chlorophenyl)methyl)thiazol-2-yl)-1-(benzo[d][1,3]dioxol-5-yl)cyclopropanecarboxamide

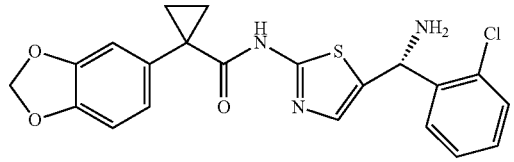

(R)-N-(5-(Amino(2-chlorophenyl)methyl)thiazol-2-yl)-1-(benzo[d][1,3]dioxol-5-yl)cyclopropanecarboxamide was prepared from (R)-N-(5-((R)-t-butylsulfinylamino(2-chlorophenyl)methyl)thiazol-2-yl)-1-(benzo[d][1,3]dioxol-5-yl)cyclopropanecarboxamide using the same protocol described for (S)-N-(5-(amino(2-chlorophenyl)methyl)thiazol-2-yl)-1-(benzo[d][1,3]dioxol-5-yl)cyclopropanecarboxamide.
$^1$H-NMR (400 MHz, CDCl$_3$) δ 8.47 (s, 1H), 7.60 (dd, J=7.7, 1.7 Hz, 1H), 7.33 (dd, J=7.9, 1.3 Hz, 1H), 7.27 (td, J=7.4, 1.5 Hz, 1H), 7.20 (td, J=7.6, 1.8 Hz, 1H), 7.16 (d, J=1.0 Hz, 1H), 6.89 (td, J=8.2, 1.7 Hz, 2H), 6.81 (d, J=7.9 Hz, 1H), 6.01 (s, 2H), 5.79 (s, 1H), 1.89 (s, 2H), 1.72-1.70 (m, 2H), 1.22-1.19 (m, 2H). HPLC ret. time 2.52 min, 10-99% CH$_3$CN, 5 min run; ESI-MS 428.2 m/z (MH$^+$).

1-(Benzo[d][1,3]dioxol-5-yl)-N-(5-((R)-(2-chlorophenyl)((R)-3-dimethyl-t-butylsilylhydroxypyrrolidin-1-yl)methyl)thiazol-2-yl)cyclopropanecarboxamide

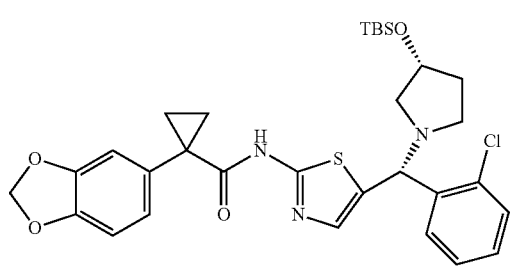

1-(Benzo[d][1,3]dioxol-5-yl)-N-(5-((R)-(2-chlorophenyl)((R)-3-dimethyl-t-butylsilylhydroxypyrrolidin-1-yl)methyl)thiazol-2-yl)cyclopropanecarboxamide was prepared from (R)-N-(5-(amino(2-chlorophenyl)methyl)thiazol-2-yl)-1-(benzo[d][1,3]dioxol-5-yl)cyclopropanecarboxamide using the same protocol for 1-(benzo[d][1,3]dioxol-5-yl)-N-(5-((S)-(2-chlorophenyl)((R)-3-dimethyl-t-butylsilylhydroxypyrrolidin-1-yl)methyl)thiazol-2-yl)cyclopropanecarboxamide. $^1$H-NMR (400 MHz, CDCl$_3$) δ 8.45 (s, 1H), 7.79 (dd, J=8.1, 1.5 Hz, 1H), 7.28-7.23 (m, 3H), 7.14-7.10 (m, 1H), 6.85 (td, J=8.1, 1.7 Hz, 2H), 6.78 (d, J=7.9 Hz, 1H), 5.99 (s, 2H), 5.08 (s, 1H), 4.36-4.31 (m, 1H), 2.94 (dd, J=9.9, 6.3 Hz, 1H), 2.65 (td, J=8.4, 3.9 Hz, 1H), 2.56 (q, J=8.3 Hz, 1H), 2.16 (dd, J=9.9, 4.6 Hz, 1H), 2.06-1.97 (m, 1H), 1.73-1.62 (m, 3H), 1.20-1.15 (m, 2H), 0.84 (s, 9H), −0.01 (d, J=7.9 Hz, 6H). HPLC ret. time 3.51 min, 10-99% CH$_3$CN, 5 min run; ESI-MS 612.41 m/z (MH$^+$).

1-(Benzo[d][1,3]dioxol-5-yl)-N-(5-((R)-(2-chlorophenyl)((R)-hydroxypyrrolidin-1-yl)methyl)thiazol-2-yl)cyclopropanecarboxamide

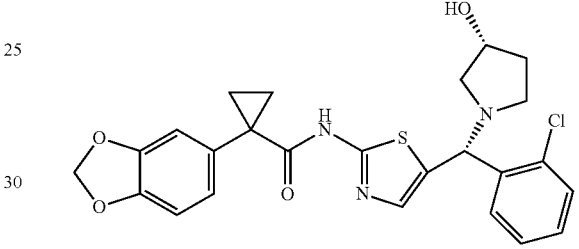

1-(Benzo[d][1,3]dioxol-5-yl)-N-(5-((R)-(2-chlorophenyl)((R)-hydroxypyrrolidin-1-yl)methyl)thiazol-2-yl)cyclopropanecarboxamide was prepared from 1-(benzo[d][1,3]dioxol-5-yl)-N-(5-((R)-(2-chlorophenyl)((R)-3-dimethyl-t-butylsilylhydroxypyrrolidin-1-yl)methyl)thiazol-2-yl)cyclopropanecarboxamide using the same protocol described for 1-(benzo[d][1,3]dioxol-5-yl)-N-(5-((S)-(2-chlorophenyl)((R)-hydroxypyrrolidin-1-yl)methyl)thiazol-2-yl)cyclopropanecarboxamide. $^1$H-NMR (400 MHz, DMSO-d6) δ 11.01 (s, 1H), 7.79 (dd, J=7.8, 1.6 Hz, 1H), 7.45-7.39 (m, 3H), 7.30-7.26 (m, 1H), 6.97 (s, 1H), 6.87 (d, J=0.9 Hz, 2H), 6.02 (s, 2H), 4.99 (s, 1H), 4.73 (d, J=4.3 Hz, 1H), 4.24-4.18 (m, 1H), 2.72 (dd, J=9.9, 6.1 Hz, 1H), 2.62 (q, J=7.8 Hz, 1H), 2.37-2.32 (m, 1H), 2.22 (dd, J=9.9, 3.2 Hz, 1H), 2.04-1.96 (m, 1H), 1.64-1.57 (m, 1H), 1.44 (q, J=3.8 Hz, 2H), 1.13 (t, J=3.8 Hz, 2H). HPLC ret. time 2.56 min, 10-99% CH$_3$CN, 5 min run; ESI-MS 498.3 m/z (MH$^+$).

The methods outlined in Scheme A, Scheme B, and Scheme C below were used to make representative compounds of this invention as recited below.

Scheme A:

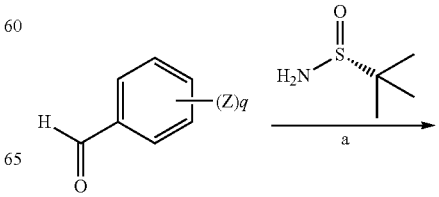

57
-continued
58
-continued
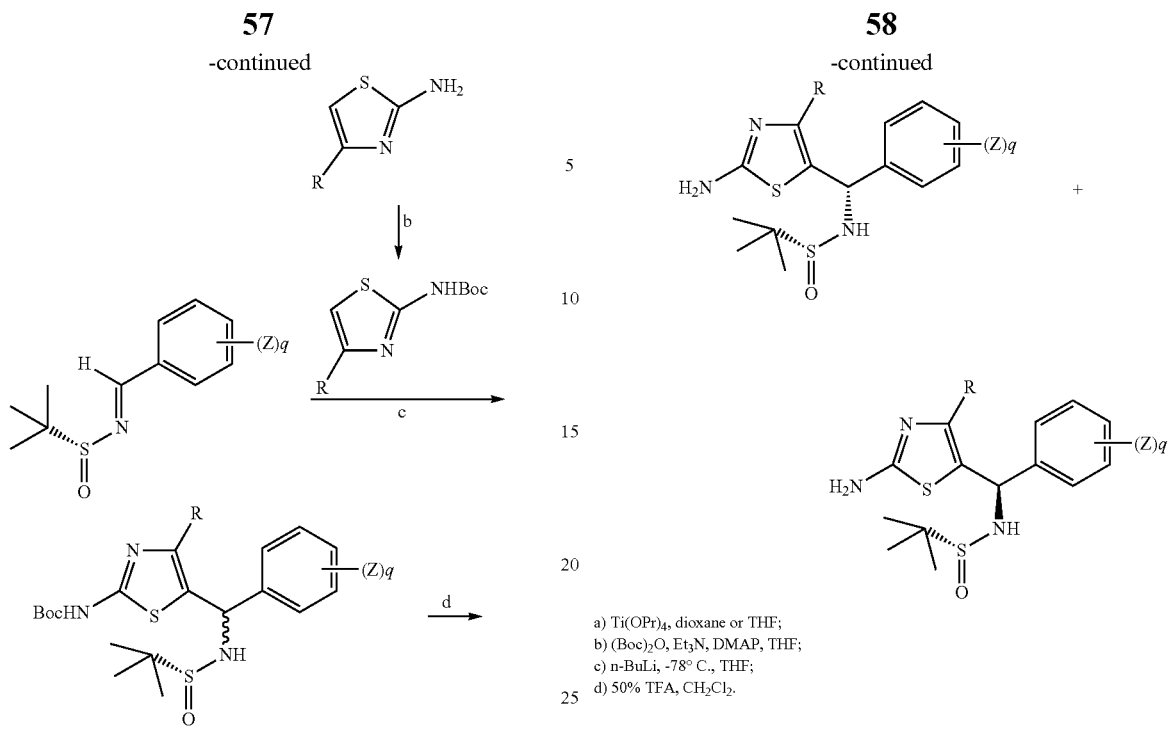
a) Ti(OPr)$_4$, dioxane or THF;
b) (Boc)$_2$O, Et$_3$N, DMAP, THF;
c) n-BuLi, -78° C., THF;
d) 50% TFA, CH$_2$Cl$_2$.
Scheme B:
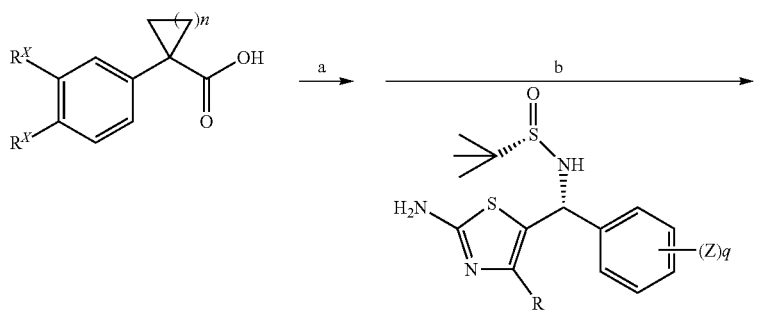
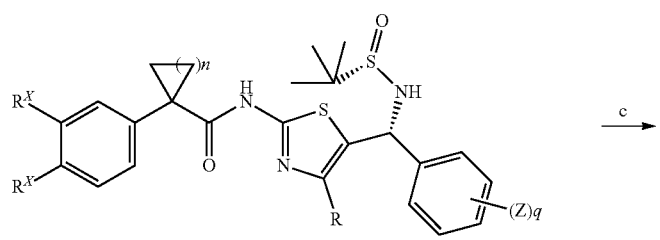
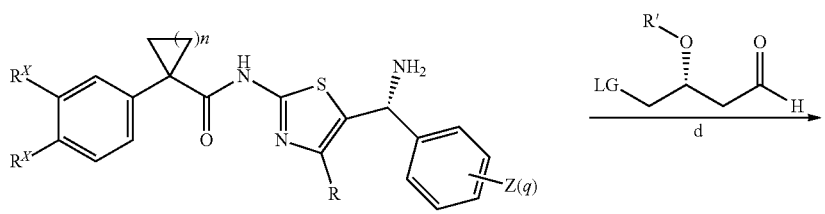

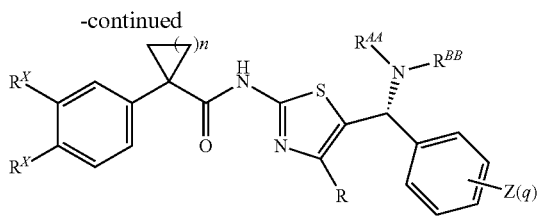

a) SOCl$_2$, DMF, 60° C.;
b) Et$_3$N, CH$_2$Cl$_2$;
c) HCl in dioxane, CH$_3$OH;
d) NaBH$_4$ (LG = leaving group).

Scheme C:

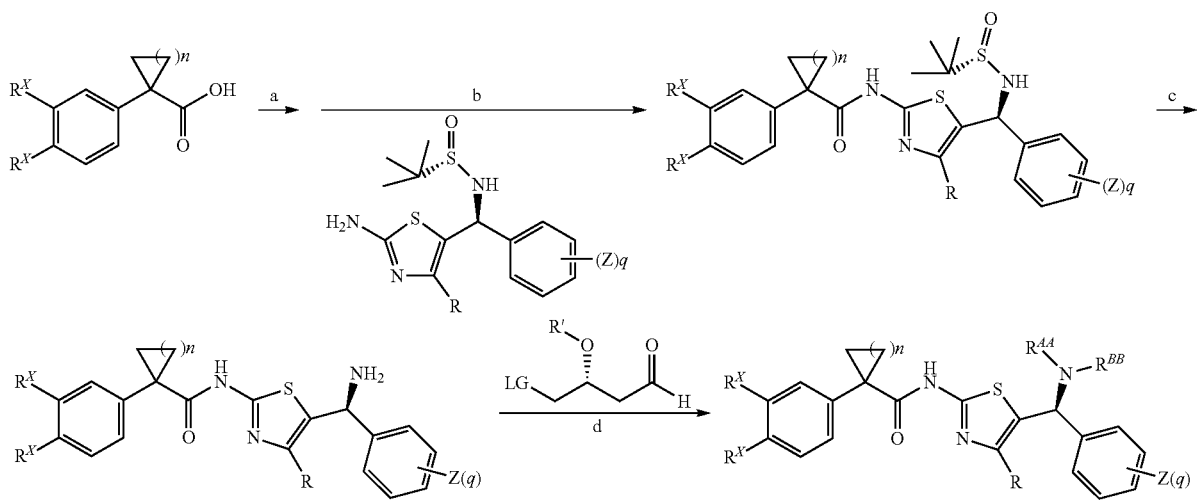

a) SOCl$_2$, DMF, 60° C.;
b) Et$_3$N, CH$_2$Cl$_2$;
c) HCl in dioxane, CH$_3$OH;
d) NaBH$_4$ (LG = leaving group).

1-(Benzo[d][1,3]dioxol-5-yl)cyclopropanecarboxylic acid

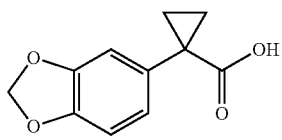

A mixture of 2-(benzo[d][1,3]dioxol-5-yl)acetonitrile (5.10 g, 31.7 mmol), 1-bromo-2-chloro-ethane (9.000 mL 108.6 mmol), and benzyltriethylammonium chloride (BTEAC, 0.181 g, 0.795 mmol) was heated to 70° C. and then 50% (wt./wt.) aqueous sodium hydroxide (26 mL) was slowly added. The reaction was stirred at 70° C. for 88 hours and then heated to reflux (130° C. bath temperature) for 24 hours. The dark brown/black reaction mixture was diluted with water (400 mL) and extracted twice with equal volumes of ethyl acetate and dichloromethane. The basic aqueous solution was acidified with concentrated hydrochloric acid to pH less than one and the precipitate was filtered and washed with 1 M hydrochloric acid. The solid material was dissolved in dichloromethane (400 mL) and washed twice with equal volumes of 1 M hydrochloric acid and once with brine. The organic solution was dried over sodium sulfate and evaporated to dryness to give a white to slightly off-white solid (5.23 g, 80.1%). $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H); HPLC ret. time 2.37 min, 10-99% CH$_3$CN, 5 min run; ESI-MS 206.1 m/z (MH$^+$).

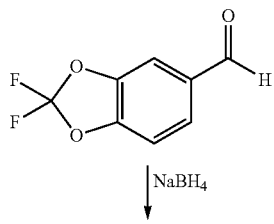

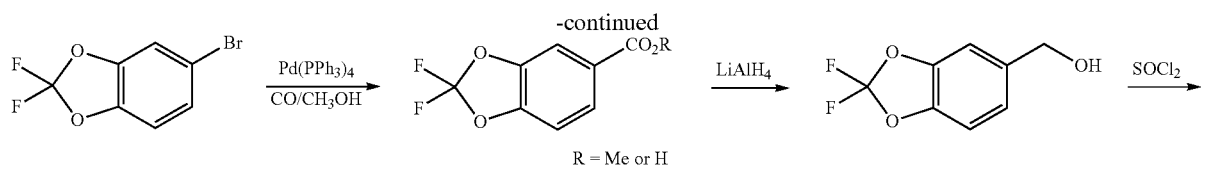

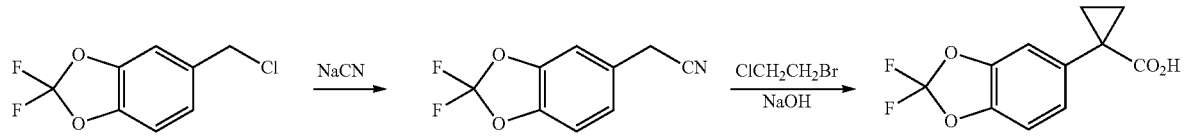

R = Me or H

Methyl 2,2-difluorobenzo[d][1,3]dioxole-5-carboxylate

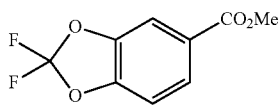

A solution of 5-bromo-2,2-difluorobenzo[d][1,3]dioxole (11.8 g, 50.0 mmol) and tetrakis(triphenylphosphine)palladium (0) [5.78 g, 5.00 mmol] in methanol (20 mL) containing acetonitrile (30 mL) and triethylamine (10 mL) was stirred under a carbon monoxide atmosphere (55 psi) at 75° C. (oil bath temperature) for 15 h. The cooled reaction mixture was filtered and the filtrate was evaporated to dryness. The residue was purified by silica gel column chromatography to give methyl 2,2-difluorobenzo[d][1,3]dioxole-5-carboxylate (11.5 g), which was used directly in the next step.

(2,2-Difluorobenzo[d][1,3]dioxol-5-yl)methanol

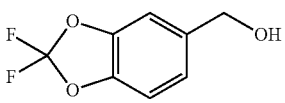

Method A: Methyl 2,2-difluorobenzo[d][1,3]dioxole-5-carboxylate from previous step (11.5 g) dissolved in anhydrous tetrahydrofuran (20 mL) was slowly added to a suspension of lithium aluminum hydride (4.10 g, 106 mmol) in anhydrous THF (100 mL) at 0° C. The mixture was then warmed to room temperature and stirred at for 1 h. The reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluorobenzo[d][1,3]dioxol-5-yl)methanol as a colorless oil (7.2 g, 76% over two steps).

Method B: To a solution of 2,2-difluorobenzo[d][1,3]dioxole-5-carbaldehyde (125 g, 0.67 mol) in anhydrous THF (400 mL) was added NaBH$_4$ (28 g, 0.74 mol) in portions at 0° C. The mixture was stirred for 1 h at 0° C., then poured into 500 mL of water. The mixture was extracted with ethyl acetate (200 mL×3). The organic phase was dried over Na$_2$SO$_4$ and concentrated in vacuo to give (2,2-difluorobenzo[d][1,3]dioxol-5-yl)methanol as colorless oil (120 g, 95%).

Method C: To a suspension of LAH (12.6 g, 0.33 mol) in THF (100 mL) was added dropwise a solution of 2,2-difluorobenzo-1,3-dioxole-5-carboxylic acid (30 g, 0.15 mol) in THF (200 mL) at 0□ under N$_2$. The mixture was allowed to warm to room temperature and stirred for one hour at this temperature. Then, water (12.6 g) and aq. NaOH (10%, 12.6 g) were added dropwise at 0□. The resulting mixture was filtered. The filtrate was dried over anhydrous Na$_2$SO$_4$ and evaporated under vacuum to give crude (2,2-difluoro-1,3-benzodioxol-5-yl)-methanol (25.5 g, 91.3%), which was used directly in the next step.

5-(Chloromethyl)-2,2-difluorobenzo[d][1,3]dioxole

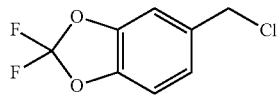

A solution of (2,2-difluorobenzo[d][1,3]dioxol-5-yl)methanol (120 g, 0.64 mol) in neat thionyl chloride (500 mL) was stirred for 2 h at 25° C. The excess thionyl chloride was distilled off in vacuo. The residue was partitioned between saturated NaHCO$_3$ (400 mL) and dichloromethane (200 mL). The separated aqueous layer was extracted with dichloromethane (300 mL×3). The combined organic layers were dried, filtered and concentrated in vacuo to give 5-(chloromethyl)-2,2-difluorobenzo[d][1,3]dioxole (117.6 g, 89%), which was directly used in the next step.

2-(2,2-difluorobenzo[d][1,3]dioxol-5-yl)acetonitrile

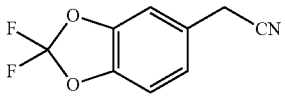

A mixture of 5-(chloromethyl)-2,2-difluorobenzo[d][1,3]dioxole (117.6 g, crude from last step) and NaCN (84 g, 1.7 mmol) in DMSO (800 mL) was stirred for 2 h at 25° C. The reaction mixture was poured into ice and extracted with EtOAc (500 mL×3). The combined organic layers were dried with anhydrous Na$_2$SO$_4$ and concentrated in vacuo to give crude product which was purified by column chromatography (P.E./EtOAc 10:1) to give 2-(2,2-difluorobenzo[d][1,3]dioxol-5-yl)acetonitrile (77.8 g, 66%). ¹H NMR (300 MHz, CDCl₃) δ 7.06-7.07 (m, 3H), 3.75 (s, 2H).

1-(2,2-Difluorobenzo[d][1,3]dioxol-5-yl)cyclopropanecarboxylic acid

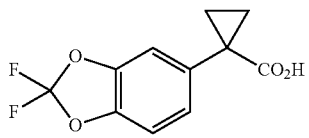

1-(2,2-difluorobenzo[d][1,3]dioxol-5-yl)cyclopropanecarboxylic acid was made by the procedure used for 1-(benzo[d][1,3]dioxol-5-yl)cyclopropanecarboxylic acid, starting from 2-(2,2-difluorobenzo[d][1,3]dioxol-5-yl)acetonitrile. Yield (86%) of a white solid. ¹H NMR (400 MHz, CDCl₃) δ 7.14-7.04 (m, 2H), 6.98-6.96 (m, 1H), 1.74-1.64 (m, 2H), 1.26-1.08 (m, 2H); ESI-MS m/z calc. 242.04. found 241.58 (M−1).

tert-Butyl thiazol-2-ylcarbamate

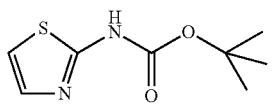

To a solution of aminothiazole (20.0 g, 199.7 mmol) and (Boc)₂O (48.0 g, 219.7 mmol) in anhydrous THF (100 mL) were added DMAP (20 mg) and Et₃N (36.0 mL, 260.0 mmol). The reaction mixture was stirred at room temperature for 18 h, diluted with DCM and washed with 0.1 N HCl, H₂O and brine. The organic layer was separated from the aqueous layer, dried over Na₂SO₄ and concentrated. The crude product was purified by column chromatography (0-40% EtOAc/Hexane) to provide tert-butyl thiazol-2-ylcarbamate as a white solid (20.7 g, 72%). ¹H-NMR (400 MHz, CDCl₃) δ 11.44 (s, 1H), 7.38 (d, J=3.6 Hz, 1H), 6.89 (d, J=3.6 Hz, 1H), 1.58 (s, 9H); HPLC ret. time 2.61 min, 10-99% CH₃CN, 5 min run; ESI-MS 145.1 m/z (MH⁺).

tert-Butyl 4-methylthiazol-2-ylcarbamate

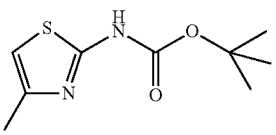

To a solution of 4-methylthiazol-2-amine (25 g, 219 mmol) and (Boc)₂O (53 g, 241 mmol) in anhydrous THF (110 mL) were added DMAP (250 mg) and Et₃N (39.6 mL, 285 mmol). The reaction mixture was stirred at room temperature for 18 h. Then the reaction was heated to reflux for 5 h, until no more starting material was detected by LC-MS. The reaction was cooled to room temperature and filtered to remove the precipitate. The filtrate was concentrated, then dissolved in CH₂Cl₂ and washed with 0.1 N aqueous HCl, H₂O and brine. The organic layer was dried over MgSO₄ and concentrated.

The residue was suspended in hexane and then filtered to obtain tert-butyl 4-methylthiazol-2-ylcarbamate as a cream colored solid (30.9 g, 66%). ¹H-NMR (400 MHz, DMSO-d₆) δ 11.30 (s, 1H), 6.68 (d, J=1.0 Hz, 1H), 2.20 (d, J=0.9 Hz, 3H), 1.47 (s, 9H); HPLC ret. time 2.68 min, 10-99% CH₃CN, 5 min run; ESI-MS 215.3 m/z (MH⁺).

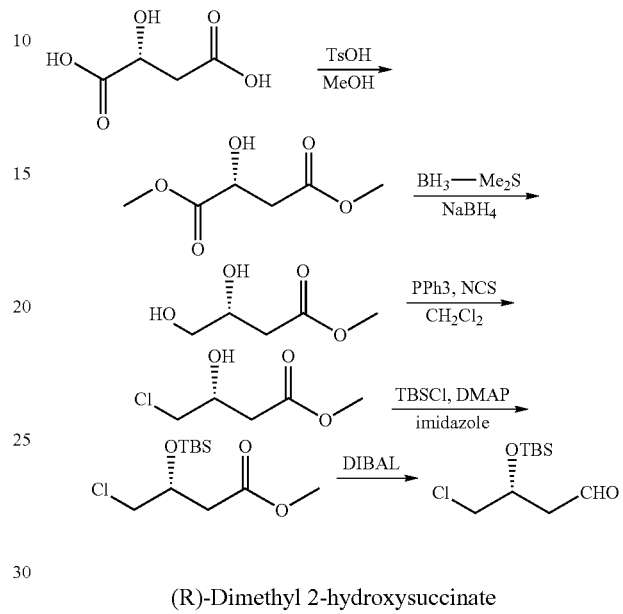

(R)-Dimethyl 2-hydroxysuccinate

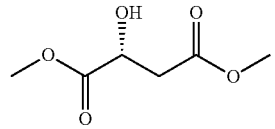

To a solution of (R)-2-hydroxysuccinic acid (134 g, 1 mol) in CH₃OH (500 mL) was added toluene-4-sulfonic acid (9.5 g, 0.05 mol). The mixture was heated to reflux overnight. Methanol was evaporated, and then water (250 mL) was added to the residue. The mixture was basified with sat. NaHCO₃ solution to pH 7-8 and extracted with ethyl acetate. The combined organic layers were washed with brine, dried over anhydrous Na₂SO₄, and concentrated under reduced pressure to give (R)-dimethyl 2-hydroxysuccinate (140 g, 86%). ¹H NMR (300 MHz, CDCl₃) δ 4.46 (dd, J=6 Hz, 4.8 Hz, 1H), 3.74 (s, 3H), 3.64 (s, 3H), 3.42 (s, 1H), 2.69-2.85 (m, 2H).

(R)-Methyl 3,4-dihydroxybutanoate

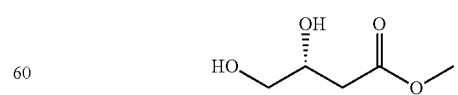

To a solution of (R)-dimethyl 2-hydroxysuccinate (140 g, 0.86 mol) in THF (1400 mL) was added dropwise Me₂S.BH₃ (86 mL, 10 M) at 20° C. over 30 min. The mixture was stirred at 20° C. for 30 min. NaBH₄ (1.63 g, 42.9 mmol) was added at 10° C. and stirred at 10° C. for 30 min. The mixture was warmed to room temperature and stirred for 1 h. CH₃OH (200 mL) was slowly added to the mixture while cooling in an ice-water bath. The resulting mixture was evaporated to give (R)-methyl 3,4-dihydroxybutanoate (130 g, crude).

(R)-Methyl 4-chloro-3-hydroxybutanoate

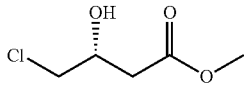

To a solution of (R)-methyl 3,4-dihydroxybutanoate (125.1 g, 0.93 mol) in CH₂Cl₂ (1.8 L) was added PPh₃ (244.5 g, 0.93 mol) and slowly added NCS (124.2 g, 0.93 mol) under ice water cooling. The mixture was stirred at 5° C. for 20 min and then stirred for 18 h at room temperature. After evaporating the solvent, the residue was purified by column chromatography (P.E\E.A 20:1-5:1, gradient) to give (R)-methyl 4-chloro-3-hydroxybutanoate (33 g, 26% over 3 steps). ¹H NMR (300 MHz, CDCl₃) δ 4.18-4.25 (m, 1H), 3.68 (s, 3H), 3.55-3.60 (m, 2H), 3.32-3.33 (d, J=4.2 Hz, 1H), 2.52-2.68 (m, 2H).

(R)-Methyl 3-(tert-butyldimethylsilyloxy)-4-chlorobutanoate

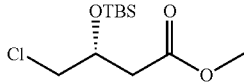

A solution of (R)-methyl 4-chloro-3-hydroxybutanoate (15 g, 98.7 mmol) in CH₂Cl₂ (240 mL) was stirred overnight with tert-butyl-chloro-dimethyl-silane (17.82 g, 118.2 mmol), imidazole (33.6 g, 493.5 mmol) and a catalytic amount of DMAP (0.6 g, 4.92 mmol) at room temperature under N₂. The reaction mixture was poured into water (150 mL) and acidified to pH 6-7 by dropwise addition of cold aqueous HCl (0.5 M). The aqueous phase was extracted with CH₂Cl₂ (3×60 mL). The combined organic phases were washed with sat. Na₂CO₃ solution, brine, dried over anhydrous Na₂SO₄ and concentrated to give (R)-methyl 3-(tert-butyldimethylsilyloxy)-4-chlorobutanoate (30 g, crude).

(R)-3-(tert-Butyldimethylsilyloxy)-4-chlorobutanal

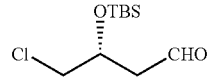

To a solution of (R)-methyl 3-(tert-butyldimethylsilyloxy)-4-chlorobutanoate (27.9 g, 104.7 mmol) in CH₂Cl₂ was added dropwise DIBAL-H (120 mL, 1 M in toluene, 120 mmol) at −78° C. under N₂ atmosphere. The mixture was stirred at −78° C. for 4 h. CH₃OH (80 mL) was added slowly to the reaction mixture at −78° C. Then the temperature was warmed to room temperature gradually. The mixture was filtered and the cake was washed with CH₂Cl₂. The combined filtrates were concentrated under reduced pressure and purified by column chromatography (PE) to give (R)-3-(tert-butyldimethylsilyloxy)-4-chlorobutanal (13 g, 60% over 2 steps). ¹H NMR (300 MHz, CDCl₃) δ9.80 (t, J=1.6 Hz, 1H), 4.35-4.42 (m, 1H), 3.53 (dd, J=11.1 Hz, 4.8 Hz, 1H), 3.46 (dd, J=12 Hz, 6.3 Hz, 1H), 2.63-2.82 (m, 2H), 0.87 (s, 9H), 0.12 (s, 3H), 0.08 (s, 3H).

(S)-3-(tert-Butyldimethylsilyloxy)-4-chlorobutanal

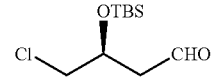

(S)-3-(tert-Butyldimethylsilyloxy)-4-chlorobutanal was prepared by the same route as (R)-3-(tert-butyldimethylsilyloxy)-4-chlorobutanal starting from (S)-2-hydroxysuccinic acid. ¹H NMR (400 MHz, CDCl₃) δ 9.72 (dd, J=1.6, 2.2 Hz, 1H), 4.33-4.28 (m, 1H), 3.46 (dd, J=4.7, 11.1 Hz, 1H), 3.39 (dd, J=6.4, 11.1 Hz, 1H), 2.68 (dd, J=1.5, 4.7 Hz, 1H), 2.62 (dd, J=2.3, 6.8 Hz, 1H), 0.79 (s, 9H), 0.04 (s, 3H), 0.01 (s, 3H).

(R)-N-(2-Chlorobenzylidene)-2-methylpropane-2-sulfinamide

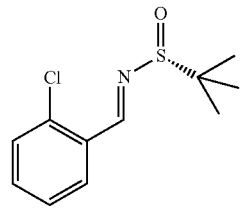

To a stirred anhydrous dioxane (500 mL) was added 2-chlorobenzaldehyde (34.8 g, 247.5 mmol) and the solution was cooled down to 0° C. in an ice bath. A solution of (R)-2-methylpropanesulfinamide (30.0 g, 247.5 mmol) in anhydrous dioxane (100 mL) was added to the aldehyde solution. Ti(OPr)₄ (105.5 g, 371.3 mmol) was then slowly added to the solution while stirring at 0° C. The reaction mixture was allowed to warm up to room temperature and stirred for 18 h, then quenched with saturated aqueous NaHCO₃ solution and filtered through a short plug of Celite using EtOAc. The organic layer was separated from the aqueous layer and dried over Na₂SO₄ and concentrated. The crude product was purified by column chromatography (0-25% EtOAc/Hexane) to provide (R)-N-(2-chlorobenzylidene)-2-methylpropane-2-sulfinamide as a yellow liquid (45.1 g, 75%). ¹H-NMR (400 MHz, CDCl₃) δ 9.05 (s, 1H), 8.06 (dd, J=7.9, 1.1 Hz, 1H), 7.47-7.41 (m, 2H), 7.37-7.33 (m, 1H), 1.28 (s, 9H); HPLC ret. time 3.45 min, 10-99% CH₃CN, 5 min run; ESI-MS 244.3 m/z (MH⁺).

(R)-N-(3,4-Dichlorobenzylidene)-2-methylpropane-2-sulfinamide

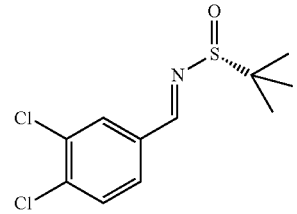

(R)-N-(3,4-Dichlorobenzylidene)-2-methylpropane-2-sulfinamide was made by the procedure used for (R)-N-(2-chlorobenzylidene)-2-methylpropane-2-sulfinamide, starting from 3,4-dichlorobenzaldehyde and (R)-2-methylpropanesulfinamide. Yield (93%) of a yellow oil that crystallizes upon standing. $^1$H-NMR (400 MHz, CDCl$_3$) ☐ 8.51 (s, 1H), 7.96 (d, J=1.9 Hz, 1H), 7.66 (dd, J=1.9, 8.3 Hz, 1H), 7.57 (d, J=8.3 Hz, 1H), 1.27 (s, 9H); HPLC ret. time 3.72 min, 10-99% CH$_3$CN, 5 min run; ESI-MS 278.1 m/z (MH$^+$).

(R)-N-(2-Chloro-4-fluorobenzylidene)-2-methylpropane-2-sulfinamide

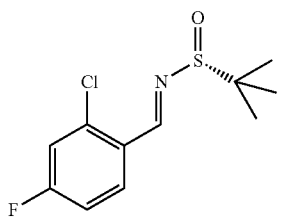

(R)-N-(2-Chloro-4-fluorobenzylidene)-2-methylpropane-2-sulfinamide was made by the procedure used for (R)-N-(2-chlorobenzylidene)-2-methylpropane-2-sulfinamide, starting from 2-chloro-4-fluorobenzaldehyde and (R)-2-methylpropanesulfinamide. Yield (74%) of a colorless solid. $^1$H-NMR (400 MHz, CDCl$_3$) δ 9.00 (s, 1H), 8.11 (dd, J=8.8, 6.2 Hz, 1H), 7.23 (dd, J=8.4, 2.5 Hz, 1H), 7.13-7.08 (m, 1H), 1.29 (s, 9H); HPLC ret. time 3.46 min, 10-99% CH$_3$CN, 5 min run; ESI-MS 262.1 m/z (MH$^+$).

(S)-N-(2-Chloro-4-fluorobenzylidene)-2-methylpropane-2-sulfinamide

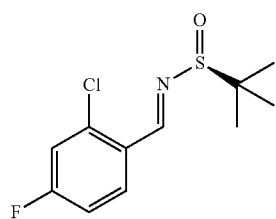

(S)-N-(2-Chloro-4-fluorobenzylidene)-2-methylpropane-2-sulfinamide was made by the procedure used for (R)-N-(2-chlorobenzylidene)-2-methylpropane-2-sulfinamide, starting from 2-chloro-4-fluorobenzaldehyde and (S)-2-methylpropanesulfinamide. Yield (78%) of a colorless solid. $^1$H-NMR (400 MHz, CDCl$_3$) δ 9.00 (s, 1H), 8.11 (dd, J=6.2, 8.8 Hz, 1H), 7.23 (dd, J=2.5, 8.4 Hz, 1H), 7.13-7.08 (m, 1H), 1.29 (s, 9H); HPLC ret. time 3.49 min, 10-99% CH$_3$CN, 5 min run; ESI-MS 262.1 m/z (MH$^+$).

(R)-N-(4-Chloro-2-fluorobenzylidene)-2-methylpropane-2-sulfinamide

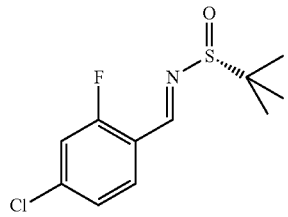

(R)-N-(4-Chloro-2-fluorobenzylidene)-2-methylpropane-2-sulfinamide was made by the procedure used for (R)-N-(2-chlorobenzylidene)-2-methylpropane-2-sulfinamide, starting from 4-chloro-2-fluorobenzaldehyde and (R)-2-methylpropanesulfinamide. Yield (65%) of a colorless solid. $^1$H-NMR (400 MHz, CDCl$_3$) δ 8.84 (s, 1H), 7.97-7.93 (m, 1H), 7.28-7.19 (m, 2H), 1.27 (s, 9H); HPLC ret. time 3.53 min, 10-99% CH$_3$CN, 5 min run; ESI-MS 262.0 m/z (MH$^+$).

(R)-tert-Butyl5-((2-chloro-4-fluorophenyl)(1,1-dimethylethylsulfinamido)methyl)thiazol-2-ylcarbamate

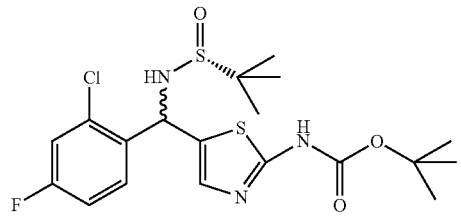

A solution of tert-butyl thiazol-2-ylcarbamate (2.0 g, 10.0 mmol) in anhydrous THF (25 mL) was stirred and cooled down to −78° C. To this solution was slowly added n-BuLi (2.5 M in hexane: 8.0 mL, 20.0 mmol). Upon completion of n-BuLi addition, the mixture was maintained at −78° C. for 1 h. A solution of (R,E)-N-(2-chloro-4-fluorobenzylidene)-2-methylpropane-2-sulfinamide (1.4 g, 5.4 mmol) in anhydrous THF (25 mL) previously cooled to −78° C. was slowly added to the above solution via canulation. The reaction was kept at −78° C. for 0.5 h, allowed to warm up to room temperature, quenched with aqueous NH$_4$Cl solution, and extracted with EtOAC (×3). The combined organic layers were dried over MgSO$_4$ and concentrated. The crude product was purified by column chromatography (0-80% EtOAc/Hexane) to provide a diasteriomeric mixture of (R)-tert-butyl 5-((2-chloro-4-fluorophenyl)(1,1-dimethylethylsulfinamido)methyl)thiazol-2-ylcarbamate as a yellow solid (2.1 g, 84%) that was used without further purification.

(S)-tert-Butyl5-((2-chloro-4-fluorophenyl)(1,1-dimethylethylsulfinamido)methyl)thiazol-2-ylcarbamate

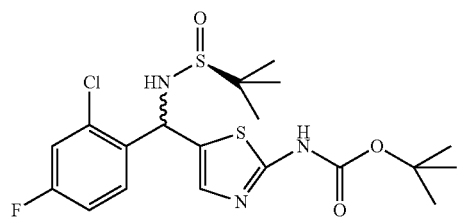

(S)-tert-Butyl5-((2-chloro-4-fluorophenyl)(1,1-dimethylethylsulfinamido) methyl)thiazol-2-ylcarbamate was made by the procedure used for (R)-tert-butyl 5-((2-chloro-4-fluorophenyl)(1,1-dimethylethylsulfinamido)methyl)thiazol-2-ylcarbamate, starting from tert-butyl thiazol-2-ylcarbamate and (S)-N-(2-chloro-4-fluorobenzylidene)-2-methylpropane-2-sulfinamide. The crude product was purified by column chromatography to provide a diasteriomeric mixture of (S)-tert-butyl 5-((2-chloro-4-fluorophenyl)(1,1-dimethylethylsulfinamido)methyl) thiazol-2-ylcarbamate as an orange-yellow solid (95%) that was used without further purification.

(R)-tert-Butyl5-((4-chloro-2-fluorophenyl)(1,1-dimethylethylsulfinamido)methyl)thiazol-2-ylcarbamate

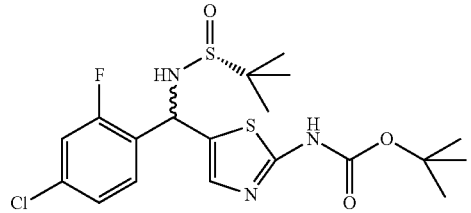

(R)-tert-Butyl5-((4-chloro-2-fluorophenyl)(1,1-dimethylethylsulfinamido) methyl)thiazol-2-ylcarbamate was made by the procedure used for (R)-tert-butyl 5-((2-chloro-4-fluorophenyl)(1,1-dimethylethylsulfinamido)methyl)thiazol-2-ylcarbamate, starting from tert-butyl thiazol-2-ylcarbamate and (R)-N-(4-chloro-2-fluorobenzylidene)-2-methylpropane-2-sulfinamide. The crude product was purified by column chromatography to provide a diasteriomeric mixture of (R)-tert-butyl 5-((4-chloro-2-fluorophenyl)(1,1-dimethylethylsulfinamido)methyl)thiazol-2-ylcarbamate (78%) that was used without further purification.

(R)-tert-Butyl5-((3,4-dichlorophenyl)(1,1-dimethylethylsulfinamido) methyl)thiazol-2-ylcarbamate

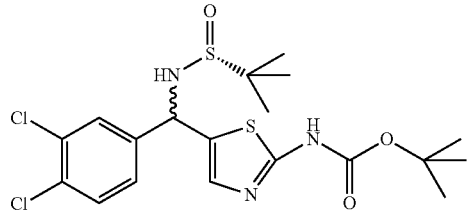

(R)-tert-Butyl 5-((3,4-dichlorophenyl)(1,1-dimethylethylsulfinamido)methyl)thiazol-2-ylcarbamate was made by the procedure used for (R)-tert-butyl 5-((2-chloro-4-fluorophenyl)(1,1-dimethylethylsulfinamido)methyl)thiazol-2-ylcarbamate, starting from tert-butyl thiazol-2-ylcarbamate and (R)-N-(3,4-dichlorobenzylidene)-2-methylpropane-2-sulfinamide. The crude product was purified by column chromatography (excess tert-butyl thiazol-2-ylcarbamate is eluted at 70% EtOAc/hexane, the desired product follows at 0-15% MeOH/EtOAc) to provide a diasteriomeric mixture of (R)-tert-butyl 5-((3,4-dichlorophenyl)(1,1-dimethylethylsulfinamido)methyl)thiazol-2-ylcarbamate as a yellow solid (92%) that was used without further purification.

(R)-tert-Butyl 5-((2-chlorophenyl)(1,1-dimethylethylsulfinamido)methyl)-4-methylthiazol-2-ylcarbamate

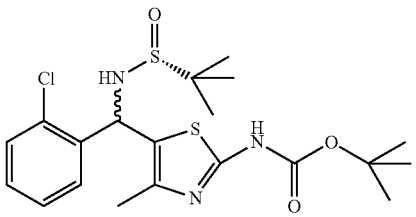

(R)-tert-Butyl 5-((2-chlorophenyl)(1,1-dimethylethylsulfinamido)methyl)-4-methylthiazol-2-ylcarbamate was made by the procedure used for (R)-tert-butyl 5-((2-chloro-4-fluorophenyl)(1,1-dimethylethylsulfinamido)methyl)thiazol-2-ylcarbamate, starting from tert-butyl 4-methylthiazol-2-ylcarbamate and (R)-N-(2-chlorobenzylidene)-2-methylpropane-2-sulfinamide. The crude product was adsorbed onto silica gel and purified by column chromatography (20-80% EtOAc/hexanes) to provide a diastereomeric mixture of (R)-tert-butyl 5-((2-chlorophenyl)(1,1-dimethylethylsulfinamido)methyl)-4-methylthiazol-2-ylcarbamate as a cream colored solid (90%) that was used without further purification.

(R)-N-((S)-(2-Aminothiazol-5-yl)(2-chloro-4-fluorophenyl)methyl)-2-methylpropane-2-sulfinamide

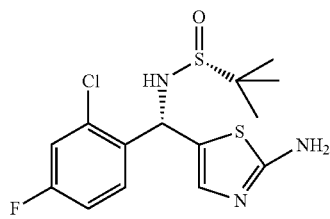

To a solution of (R)-tert-Butyl 5-((2-chloro-4-fluorophenyl)(1,1-dimethylethylsulfinamido)methyl)thiazol-2-ylcarbamate (1.6 g, 3.5 mmol) in $CH_2Cl_2$ (6 mL) was added TFA (6 mL). The reaction was stirred at room temperature for 2 h. The TFA and $CH_2Cl_2$ were removed under vacuum. The crude product was re-dissolved in $CH_2Cl_2$, washed with aqueous $NaHCO_3$ solution, dried over $MgSO_4$ and concentrated. The crude product was recrystallized from EtOAc to provide (R)-N-((S)-(2-aminothiazol-5-yl)(2-chloro-4-fluorophenyl)methyl)-2-methylpropane-2-sulfinamide as colorless solid (672 mg, 53%). $^1H$ NMR (400 MHz, $CDCl_3$) δ 7.56 (dd, J=8.7, 5.9 Hz, 1H), 7.16 (dd, J=8.4, 2.6 Hz, 1H), 7.06 (td, J=8.2, 2.6 Hz, 1H), 6.89 (d, J=0.8 Hz, 1H), 6.07 (d, J=4.6 Hz, 1H), 5.22 (d, J=2.9 Hz, 2H), 4.06 (d, J=4.6 Hz, 1H), 1.28 (s, 9H); HPLC ret. time 2.28 min, 10-99% $CH_3CN$, 5 min run; ESI-MS 362.3 m/z $(MH^+)$.

(S)-N-((R)-(2-Aminothiazol-5-yl)(2-chloro-4-fluorophenyl)methyl)-2-methylpropane-2-sulfinamide

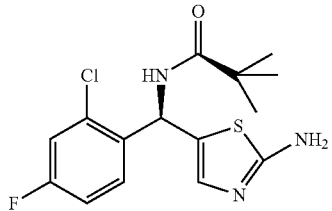

(S)-N-((R)-(2-Aminothiazol-5-yl)(2-chloro-4-fluorophenyl)methyl)-2-methylpropane-2-sulfinamide was made by the procedure used for (R)-N-((S)-(2-aminothiazol-5-yl)(2-chloro-4-fluorophenyl)methyl)-2-methylpropane-2-sulfinamide, starting from (S)-tert-butyl 5-((4-chloro-2-fluorophenyl)(1,1-dimethylethylsulfinamido)methyl)thiazol-2-ylcarbamate. The crude product was purified by column chromatography (0-5% EtOH/EtOAc) to provide the desired product (38%). $^1$H-NMR (400 MHz, CDCl$_3$) δ 9.14 (br s, 2H), 7.54 (dd, J=5.7, 8.7 Hz, 1H), 7.21 (dd, J=2.6, 8.1 Hz, 1H), 7.13-7.08 (m, 1H), 6.73 (d, J=0.6 Hz, 1H), 6.00 (d, J=5.6 Hz, 1H), 4.67 (d, J=5.7 Hz, 1H), 1.26 (s, 9H); HPLC ret. time 2.23 min, 10-99% CH$_3$CN, 5 min run; ESI-MS 362.3 m/z (MH$^+$).

(R)-N-((S)-(2-Aminothiazol-5-yl)(4-chloro-2-fluorophenyl)methyl)-2-methylpropane-2-sulfinamide

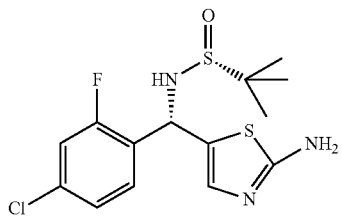

(R)-N-((S)-(2-Aminothiazol-5-yl)(4-chloro-2-fluorophenyl)methyl)-2-methylpropane-2-sulfinamide was made by the procedure used for (R)-N-((S)-(2-aminothiazol-5-yl)(2-chloro-4-fluorophenyl)methyl)-2-methylpropane-2-sulfinamide, starting from (R)-tert-butyl 5-((4-chloro-2-fluorophenyl)(1,1-dimethylethylsulfinamido)methyl)thiazol-2-ylcarbamate. The crude product was purified by column chromatography (0-5% EtOH/EtOAc) to provide an orange solid (87%). $^1$H-NMR (400 MHz, CDCl$_3$) δ 8.62 (br s, 2H), 7.36 (t, J=8.1 Hz, 1H), 7.21 (dd, J=1.7, 8.3 Hz, 1H), 7.16 (dd, J=1.9, 10.1 Hz, 1H), 6.74 (s, 1H), 5.81 (d, J=5.9 Hz, 1H), 4.18 (d, J=5.9 Hz, 1H), 1.25 (s, 9H); HPLC ret. time 2.29 min, 10-99% CH$_3$CN, 5 min run; ESI-MS 362.3 m/z (MH$^+$).

1-(Benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide

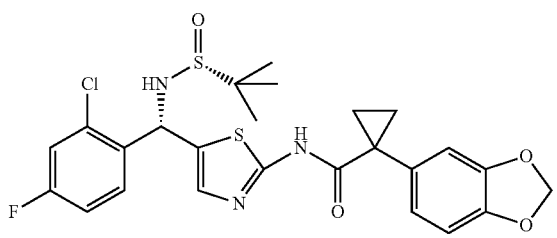

To a solution of 1-(benzo[d][1,3]dioxol-5-yl)cyclopropanecarboxylic acid (618 mg, 3.0 mmol) in anhydrous CH$_2$Cl$_2$ (6 mL) was slowly added (COCl)$_2$ (0.3 mL, 3.4 mmol) at −10° C. followed by DMF (3 drops). The reaction mixture was stirred at −10° C. for 0.5 h. The excess (COCl)$_2$ was removed under vacuum. The acid chloride (10.5 mmol) was then dissolved in anhydrous CH$_2$Cl$_2$ (3 mL) and was slowly added to a solution of (R)-N-((S)-(2-aminothiazol-5-yl)(2-chloro-4-fluorophenyl)methyl)-2-methylpropane-2-sulfinamide (648 mg, 1.8 mmol) and Et$_3$N (1.8 mL, 6 mmol) in anhydrous CH$_2$Cl$_2$ (3 mL). The reaction mixture was stirred at room temperature for 1 h, diluted with CH$_2$Cl$_2$ and washed with 1N HCl, NaHCO$_3$ and brine. The organic layer was separated from the aqueous layer and dried over MgSO$_4$ and concentrated. The crude product was purified by column chromatography (40-60% EtOAc/Hexane) to provide 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide as a colorless solid (680 mg, 69%). $^1$H-NMR (400 MHz, CDCl$_3$) δ 8.60 (s, 1H), 7.60 (dd, J=8.7, 5.9 Hz, 1H), 7.28 (d, J=2.0 Hz, 1H), 7.13 (dd, J=8.3, 2.6 Hz, 1H), 7.05 (td, J=8.2, 2.6 Hz, 1H), 6.90 (td, J=8.3, 1.7 Hz, 2H), 6.83 (d, J=7.9 Hz, 1H), 6.18 (d, J=4.3 Hz, 1H), 6.04 (s, 2H), 3.90 (d, J=4.3 Hz, 1H), 1.73 (td, J=5.4, 2.0 Hz, 2H), 1.28 (t, J=7.1 Hz, 2H), 1.29 (s, 9H). HPLC ret. time 3.65 min, 10-99% CH$_3$CN, 5 min run; ESI-MS 550.5 m/z (MH$^+$).

N-(5-((S)-(2-Chloro-4-fluorophenyl)((R)-1,1-dimethylethylsulfinamido)methyl)thiazol-2-yl)-1-(2,2-difluorobenzo[d][1,3]dioxol-5-yl)cyclopropanecarboxamide

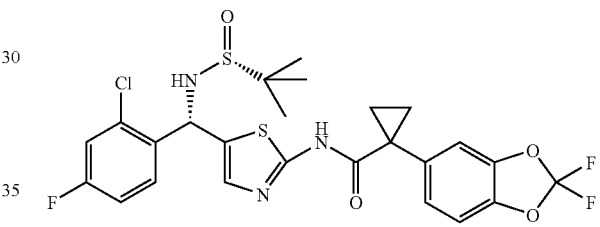

N-(5-((S)-(2-Chloro-4-fluorophenyl)((R)-1,1-dimethylethylsulfinamido)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide, starting from 1-(2,2-difluorobenzo[d][1,3]dioxol-5-yl)cyclopropanecarboxylic acid and (R)-N-((S)-(2-aminothiazol-5-yl)(2-chloro-4-fluorophenyl)methyl)-2-methylpropane-2-sulfinamide. Yield (77%). $^1$H-NMR (400 MHz, CDCl$_3$) δ 8.63 (s, 1H), 7.59 (dd, J=8.7, 5.9 Hz, 1H), 7.28 (s, 1H), 7.21-7.11 (m, 4H), 7.06 (td, J=8.2, 2.5 Hz, 1H), 6.18 (d, J=4.2 Hz, 1H), 3.92 (d, J=4.3 Hz, 1H), 1.82-1.79 (m, 2H), 1.32-1.25 (m, 11H); HPLC ret. time 3.90 min, 10-99% CH$_3$CN, 5 min run; ESI-MS 586.3 m/z (MH$^+$).

1-(Benzo[d][1,3]dioxol-5-yl)-N-(5-((R)-(2-chloro-4-fluorophenyl)((S)-1,1-dimethylethylsulfinamido)methyl)thiazol-2-yl)cyclopropanecarboxamide

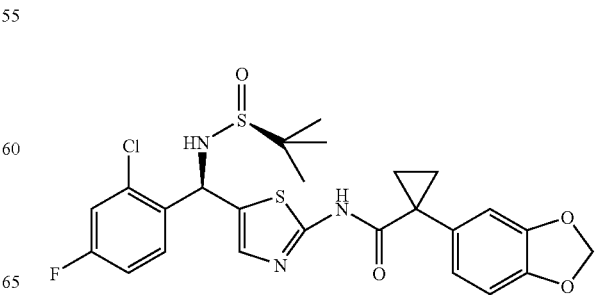

1-(Benzo[d][1,3]dioxol-5-yl)-N-(5-((R)-(2-chloro-4-fluorophenyl)((S)-1,1-dimethylethylsulfinamido)methyl)thiazol-2-yl)cyclopropanecarboxamide was made by the procedure used for 1-(benzo[d][1,3]dioxol-5-yl)-N-(5-((S)-(2-chloro-4-fluorophenyl) ((R)-1,1-dimethylethylsulfinamido)methyl)thiazol-2-yl)cyclopropanecarboxamide, starting from 1-(benzo[d][1,3]dioxol-5-yl)cyclopropanecarboxylic acid and (S)-N-((R)-(2-aminothiazol-5-yl)(2-chloro-4-fluorophenyl)methyl)-2-methylpropane-2-sulfinamide. Yield (50%). $^1$H-NMR (400 MHz, DMSO-$d_6$) δ 11.10 (s, 1H), 7.78 (dd, J=6.3, 8.8 Hz, 1H), 7.45 (dd, J=2.6, 8.8 Hz, 1H), 7.35 (td, J=8.6, 2.7 Hz, 1H), 7.03 (s, 1H), 6.95 (s, 1H), 6.86 (s, 2H), 6.45 (d, J=6.7 Hz, 1H), 6.00 (s, 2H), 5.95 (d, J=6.5 Hz, 1H), 1.46-1.43 (m, 2H), 1.25-1.24 (m, 2H), 1.14 (s, 9H); HPLC ret. time 3.65 min, 10-99% $CH_3CN$, 5 min run; ESI-MS 550.5 m/z (MH$^+$).

N-(5-((R)-(2-Chloro-4-fluorophenyl)((S)-1,1-dimethylethylsulfinamido)methyl)thiazol-2-yl)-1-(2,2-difluorobenzo[d][1,3]dioxol-5-yl)cyclopropanecarboxamide

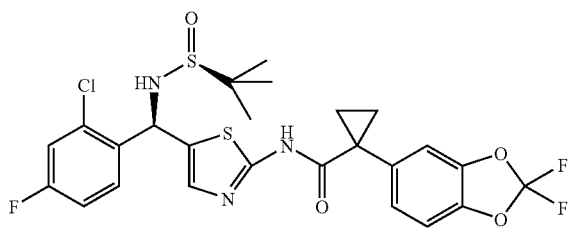

N-(5-((R)-(2-Chloro-4-fluorophenyl)((S)-1,1-dimethylethylsulfinamido)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide, starting from 1-(2,2-difluorobenzo[d][1,3]dioxol-5-yl)cyclopropanecarboxylic acid and (S)-N-((R)-(2-aminothiazol-5-yl)(2-chloro-4-fluorophenyl)methyl)-2-methylpropane-2-sulfinamide. Yield (50%). $^1$H-NMR (400 MHz, DMSO-$d_6$) δ 11.38 (s, 1H), 7.78 (dd, J=6.2, 8.8 Hz, 1H), 7.47-7.44 (m, 2H), 7.37-7.32 (m, 2H), 7.21 (dd, J=1.6, 8.3 Hz, 1H), 7.04 (s, 1H), 6.45 (d, J=6.6 Hz, 1H), 5.95 (d, J=6.5 Hz, 1H), 1.54-1.50 (m, 2H), 1.22-1.21 (m, 2H), 1.14 (s, 9H); HPLC ret. time 3.90 min, 10-99% $CH_3CN$, 5 min run; ESI-MS 586.3 m/z (MH$^+$).

1-(Benzo[d][1,3]dioxol-5-yl)-N-(5-((S)-(4-chloro-2-fluorophenyl)((R)-1,1-dimethylethylsulfinamido)methyl)thiazol-2-yl)cyclopropanecarboxamide

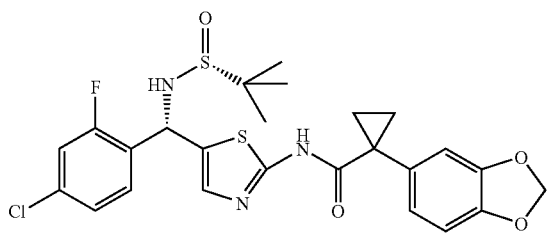

1-(Benzo[d][1,3]dioxol-5-yl)-N-(5-((S)-(4-chloro-2-fluorophenyl)((R)-1,1-dimethylethylsulfinamido)methyl)thiazol-2-yl)cyclopropanecarboxamide was made by the procedure used for 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide, starting from 1-(benzo[d][1,3]dioxol-5-yl)cyclopropanecarboxylic acid and (R)-N-((S)-(2-aminothiazol-5-yl)(4-chloro-2-fluorophenyl)methyl)-2-methylpropane-2-sulfinamide. Yield (64%). $^1$H-NMR (400 MHz, CDCl$_3$) δ 8.56 (s, 1H), 7.43 (t, J=8.1 Hz, 1H), 7.18 (s, 1H), 7.16 (dd, J=1.5, 8.3 Hz, 1H), 7.08 (dd, J=2.0, 10.0 Hz, 1H), 6.89 (td, J=8.0, 1.7 Hz, 2H), 6.81 (d, J=7.9 Hz, 1H), 6.01-5.99 (m, 3H), 3.90 (d, J=5.0 Hz, 1H), 1.73-1.70 (m, 2H), 1.28-1.23 (m, 1H); HPLC ret. time 3.69 min, 10-99% $CH_3CN$, 5 min run; ESI-MS 550.5 m/z (MH$^+$).

N-(5-((S)-(4-Chloro-2-fluorophenyl)((R)-1,1-dimethylethylsulfinamido)methyl)thiazol-2-yl)-1-(2,2-difluorobenzo[d][1,3]dioxol-5-yl)cyclopropanecarboxamide

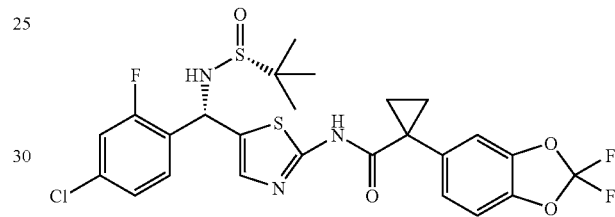

N-(5-((S)-(4-Chloro-2-fluorophenyl)((R)-1,1-dimethylethylsulfinamido)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide, starting from 1-(2,2-difluorobenzo[d][1,3]dioxol-5-yl)cyclopropanecarboxylic acid and (R)-N-((S)-(2-aminothiazol-5-yl)(4-chloro-2-fluorophenyl)methyl)-2-methylpropane-2-sulfinamide. Yield (53%). $^1$H-NMR (400 MHz, DMSO-$d_6$) δ 11.37 (s, 1H), 7.66 (t, J=8.3 Hz, 1H), 7.45-7.42 (m, 2H), 7.38 (dd, J=2.0, 8.4 Hz, 1H), 7.34 (d, J=8.3 Hz, 1H), 7.21 (dd, J=1.5, 8.3 Hz, 1H), 7.11 (s, 1H), 6.33 (d, J=6.7 Hz, 1H), 5.89 (d, J=6.5 Hz, 1H), 1.55-1.52 (m, 2H), 1.24-1.22 (m, 2H), 1.13 (d, J=9.5 Hz, 9H); HPLC ret. time 3.93 min, 10-99% $CH_3CN$, 5 min run; ESI-MS 586.5 m/z (MH$^+$).

(S)-N-(5-(Amino(2-chloro-4-fluorophenyl)methyl)thiazol-2-yl)-1-(benzo[d][1,3]dioxol-5-yl)cyclopropanecarboxamide

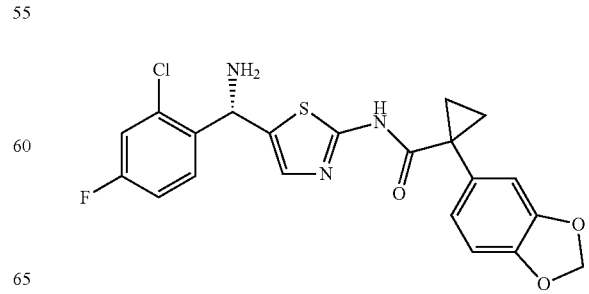

To a solution of 1-(benzo[d][1,3]dioxol-5-yl)-N-(5-((S)-(2-chloro-4-fluorophenyl)((R)-1,1-dimethylethylsulfinamido)methyl)thiazol-2-yl)cyclopropanecarboxamide (659 mg, 1.2 mmol) in MeOH (5 mL) was added 4M HCl in dioxane (1.8 mL, 7.2 mmol). The reaction mixture was stirred at room temperature for 1.5 h and evaporated to dryness. The crude product was dissolved in CH$_2$Cl$_2$. The organic layer was washed with aqueous NaHCO$_3$ solution (50 mL×2), brine (50 mL×1), dried over MgSO$_4$ and concentrated to provide (S)-N-(5-(Amino(2-chloro-4-fluorophenyl)methyl)thiazol-2-yl)-1-(benzo[d][1,3]dioxol-5-yl)cyclopropanecarboxamide as a colorless solid that was used without further purification. $^1$H-NMR (400 MHz, CDCl$_3$) δ 8.48 (br s, 1H), 7.63 (dd, J=6.1, 8.7 Hz, 1H), 7.18 (s, 1H), 7.08 (dd, J=2.6, 8.4 Hz, 1H), 6.99 (td, J=8.3, 2.6 Hz, 1H), 6.91-6.86 (m, 2H), 6.81 (d, J=7.9 Hz, 1H), 6.01 (s, 2H), 5.78 (s, 1H), 3.80 (s, 2H), 1.74-1.67 (m, 2H), 1.30-1.22 (m, 2H); HPLC ret. time 2.67 min, 10-99% CH$_3$CN, 5 min run; ESI-MS 446.3 m/z (MH$^+$).

(S)-N-(5-(Amino(2-chloro-4-fluorophenyl)methyl)thiazol-2-yl)-1-(2,2-difluorobenzo[d][1,3]dioxol-5-yl)cyclopropanecarboxamide

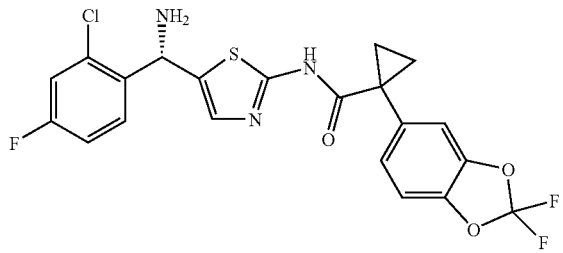

(S)-N-(5-(Amino(2-chloro-4-fluorophenyl)methyl)thiazol-2-yl)-1-(2,2-difluorobenzo[d][1,3]dioxol-5-yl)cyclopropanecarboxamide was made by the procedure used for (S)-N-(5-(amino(2-chloro-4-fluorophenyl)methyl)thiazol-2-yl)-1-(benzo[d][1,3]dioxol-5-yl)cyclopropanecarboxamide, starting from N-(5-((S)-(2-chloro-4-fluorophenyl)((R)-1,1-dimethylethylsulfinamido)methyl)thiazol-2-yl)-1-(2,2-difluorobenzo[d][1,3]dioxol-5-yl)cyclopropanecarboxamide. The crude product was used without further purification. $^1$H-NMR (400 MHz, CDCl$_3$) δ 8.35 (s, 1H), 7.65 (dd, J=6.1, 8.7 Hz, 1H), 7.22-7.17 (m, 3H), 7.12-7.10 (m, 2H), 7.02 (td, J=8.3, 2.6 Hz, 1H), 5.80 (s, 1H), 3.83 (s, 2H), 1.83-1.77 (m, 2H), 1.28-1.25 (m, 2H); HPLC ret. time 2.87 min, 10-99% CH$_3$CN, 5 min run; ESI-MS 482.3 m/z (MH$^+$).

(R)-N-(5-(Amino(2-chloro-4-fluorophenyl)methyl)thiazol-2-yl)-1-(benzo[d][1,3]dioxol-5-yl)cyclopropanecarboxamide

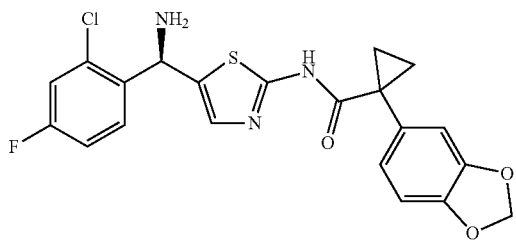

(R)-N-(5-(Amino(2-chloro-4-fluorophenyl)methyl)thiazol-2-yl)-1-(benzo[d][1,3]dioxol-5-yl)cyclopropanecarboxamide was made by the procedure used for (S)-N-(5-(amino(2-chloro-4-fluorophenyl)methyl)thiazol-2-yl)-1-(benzo[d][1,3]dioxol-5-yl)cyclopropanecarboxamide, starting from 1-(benzo[d][1,3]dioxol-5-yl)-N-(5-((R)-(2-chloro-4-fluorophenyl)((S)-1,1-dimethylethylsulfinamido)methyl)thiazol-2-yl)cyclopropane carboxamide. The crude product was purified by column chromatography (0-2.5% Et$_3$N/EtOAc) to provide a pale yellow solid (77%). $^1$H-NMR (400 MHz, DMSO-d$_6$) δ 10.80 (br s, 1H), 7.80 (dd, J=6.4, 8.8 Hz, 1H), 7.38 (dd, J=2.6, 8.8 Hz, 1H), 7.27 (td, J=8.5, 2.7 Hz, 1H), 7.07 (d, J=0.9 Hz, 1H), 6.95 (s, 1H), 6.86 (d, J=0.9 Hz, 2H), 6.00 (s, 2H), 5.53 (s, 1H), 1.44-1.41 (m, 2H), 1.13-1.10 (m, 2H); HPLC ret. time 2.67 min, 10-99% CH$_3$CN, 5 min run; ESI-MS 446.3 m/z (MH$^+$).

(R)-N-(5-(Amino(2-chloro-4-fluorophenyl)methyl)thiazol-2-yl)-1-(2,2-difluorobenzo[d][1,3]dioxol-5-yl)cyclopropanecarboxamide

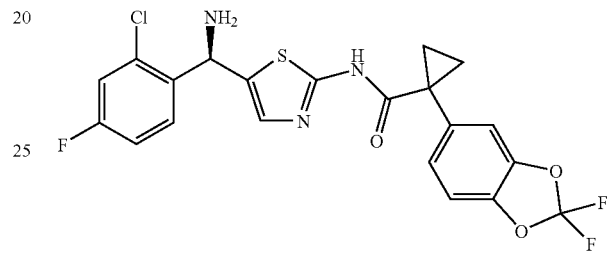

(R)-N-(5-(Amino(2-chloro-4-fluorophenyl)methyl)thiazol-2-yl)-1-(2,2-difluorobenzo[d][1,3]dioxol-5-yl)cyclopropanecarboxamide was made by the procedure used for (R)-N-(5-(amino(2-chloro-4-fluorophenyl)methyl)thiazol-2-yl)-1-(benzo[d][1,3]dioxol-5-yl)cyclopropanecarboxamide, starting from N-(5-((R)-(2-chloro-4-fluorophenyl)((S)-1,1-dimethylethylsulfinamido)methyl)thiazol-2-yl)-1-(2,2-difluorobenzo[d][1,3]dioxol-5-yl)cyclopropanecarboxamide (79%). $^1$H-NMR (400 MHz, DMSO-d$_6$) δ 7.80 (dd, J=6.4, 8.8 Hz, 1H), 7.43 (d, J=1.7 Hz, 1H), 7.38 (dd, J=2.6, 8.8 Hz, 1H), 7.34 (d, J=8.3 Hz, 1H), 7.27 (td, J=8.5, 2.6 Hz, 1H), 7.20 (dd, J=1.8, 8.3 Hz, 1H), 7.07 (d, J=0.9 Hz, 1H), 5.53 (s, 1H), 1.52-1.49 (m, 2H), 1.21-1.19 (m, 2H); HPLC ret. time 2.91 min, 10-99% CH$_3$CN, 5 min run; ESI-MS 482 m/z (MH$^+$).

(S)-N-(5-(Amino(4-chloro-2-fluorophenyl)methyl)thiazol-2-yl)-1-(benzo[d][1,3]dioxol-5-yl)cyclopropanecarboxamide

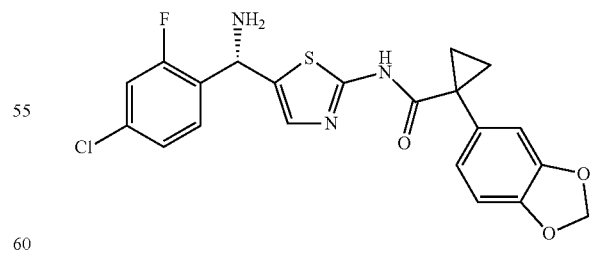

(S)-N-(5-(Amino(4-chloro-2-fluorophenyl)methyl)thiazol-2-yl)-1-(benzo[d][1,3]dioxol-5-yl)cyclopropanecarboxamide was made by the procedure used for (R)-N-(5-(amino(2-chloro-4-fluorophenyl)methyl)thiazol-2-yl)-1-(benzo[d][1,3]dioxol-5-yl)cyclopropanecarboxamide, starting from 1-(benzo[d][1,3]dioxol-5-yl)-N-(5-((S)-(4- chloro-2-fluorophenyl)((R)-1,1-dimethylethylsulfinamido)methyl)thiazol-2-yl)cyclopropanecarboxamide (79%). ¹H NMR (400 MHz, CDCl₃) δ 8.48 (s, 1H), 7.47 (t, J=8.2 Hz, 1H), 7.14-7.12 (m, 2H), 7.05 (dd, J=2.0, 10.1 Hz, 1H), 6.91-6.87 (m, 2H), 6.81 (d, J=7.9 Hz, 1H), 6.01 (s, 2H), 5.61 (s, 1H), 1.86 (s, 2H), 1.71 (dd, J=3.6, 6.7 Hz, 2H), 1.22-1.19 (m, 2H); HPLC ret. time 2.71 min, 10-99% CH₃CN, 5 min run; ESI-MS 446.3 m/z (MH⁺).

(S)-N-(5-(Amino(4-chloro-2-fluorophenyl)methyl)thiazol-2-yl)-1-(2,2-difluorobenzo[d][1,3]dioxol-5-yl)cyclopropanecarboxamide

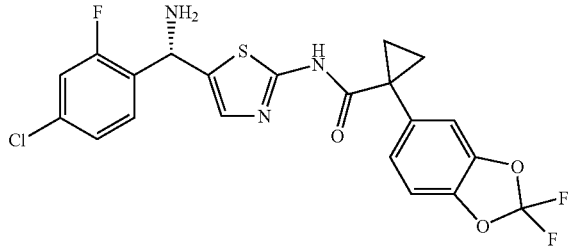

(S)-N-(5-(Amino(4-chloro-2-fluorophenyl)methyl)thiazol-2-yl)-1-(2,2-difluorobenzo[d][1,3]dioxol-5-yl)cyclopropanecarboxamide was made by the procedure used for (R)-N-(5-(amino(2-chloro-4-fluorophenyl)methyl)thiazol-2-yl)-1-(benzo[d][1,3]dioxol-5-yl)cyclopropanecarboxamide, starting from N-(5-((S)-(4-chloro-2-fluorophenyl)((R)-1,1-dimethylethylsulfinamido)methyl)thiazol-2-yl)-1-(2,2-difluorobenzo[d][1,3]dioxol-5-yl)cyclopropanecarboxamide (88%). ¹H NMR (400 MHz, DMSO-d₆) δ 11.20 (br s, 1H), 7.66 (t, J=8.3 Hz, 1H), 7.43 (d, J=1.7 Hz, 1H), 7.39-7.30 (m, 3H), 7.20 (dd, J=1.7, 8.3 Hz, 1H), 7.09 (s, 1H), 5.45 (s, 1H), 1.52-1.49 (m, 2H), 1.22-1.20 (m, 2H); HPLC ret. time 2.94 min, 10-99% CH₃CN, 5 min run; ESI-MS 482.3 m/z (MH⁺).

1-(Benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide

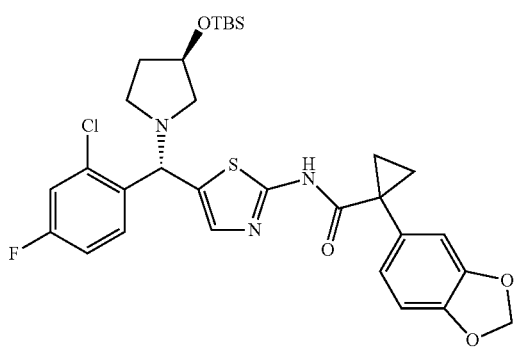

To a solution of (S)-N-(5-(amino(2-chloro-4-fluorophenyl)methyl)thiazol-2-yl)-1-(benzo[d][1,3]dioxol-5-yl)cyclopropanecarboxamide (1.2 mmol) in MeOH (10 mL) was added (R)-3-(tert-butyldimethylsilyloxy)-4-chlorobutanal (341 mg, 1.4 mmol). The reaction mixture was stirred at room temperature for 5 min. Then NaBH₄ (68 mg, 1.8 mmol) was added and stirring was continued at room temperature for 1 h. The reaction was diluted with H₂O and extracted with EtOAc. The combined organic layers were washed with brine and dried over MgSO₄. After the removal of solvent, the residue was purified by column chromatography (10-20% EtOAc/Hexane) to afford 1-(Benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide (446 mg, 59% over two steps). ¹H NMR (400 MHz, CDCl₃) δ 8.45 (s, 1H), 7.79 (dd, J=8.6, 6.3 Hz, 1H), 7.25 (d, J=6.4 Hz, 1H), 7.01-6.94 (m, 2H), 6.85 (td, J=8.3, 1.7 Hz, 2H), 6.78 (d, J=7.9 Hz, 1H), 5.99 (s, 2H), 4.99 (s, 1H), 4.35-4.30 (m, 1H), 2.77 (dd, J=9.9, 6.2 Hz, 1H), 2.51-2.48 (m, 2H), 2.36 (dd, J=9.9, 4.3 Hz, 1H), 2.06-2.01 (m, 1H), 1.71-1.65 (m, 3H), 1.18 (t, J=3.0 Hz, 2H), 0.85 (s, 9H), −0.01 (d, J=7.3 Hz, 6H); HPLC ret. time 3.59 min, 10-99% CH₃CN, 5 min run; ESI-MS 630.6 m/z (MH⁺).

N-(5-((S)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide

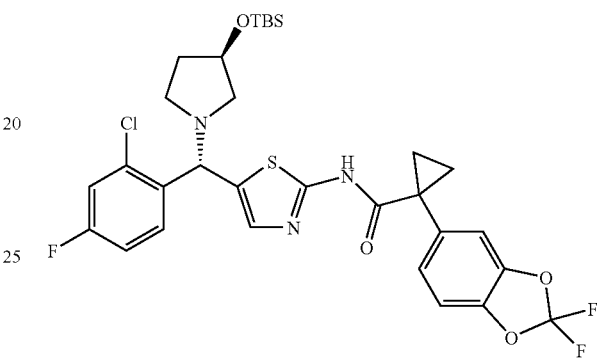

N-(5-((S)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide, starting from (S)-N-(5-(amino(2-chloro-4-fluorophenyl)methyl)thiazol-2-yl)-1-(2,2-difluorobenzo[d][1,3]dioxol-5-yl)cyclopropanecarboxamide and (R)-3-(tert-butyldimethylsilyloxy)-4-chlorobutanal (56% over two steps). ¹H NMR (400 MHz, CDCl₃) δ 8.31 (s, 1H), 7.79 (dd, J=8.6, 6.3 Hz, 1H), 7.25 (d, J=7.9 Hz, 1H), 7.13 (td, J=8.4, 1.6 Hz, 2H), 7.06 (d, J=8.1 Hz, 1H), 7.01-6.95 (m, 2H), 4.99 (s, 1H), 4.35-4.30 (m, 1H), 2.76 (dd, J=9.8, 6.2 Hz, 1H), 2.50 (t, J=6.9 Hz, 2H), 2.37 (dd, J=10.0, 4.2 Hz, 1H), 2.08-1.98 (m, 1H), 1.79-1.64 (m, 3H), 1.24-1.19 (m, 2H), 0.85 (s, 9H), −0.01 (d, J=7.4 Hz, 6H); HPLC ret. time 3.80 min, 10-99% CH₃CN, 5 min run; ESI-MS 666.4 m/z (MH⁺).

1-(Benzo[d][1,3]dioxol-5-yl)-N-(5-((R)-((R)-3-(tert-butyldimethylsilyloxy)pyrrolidin-1-yl)(2-chloro-4-fluorophenyl)methyl)thiazol-2-yl)cyclopropanecarboxamide

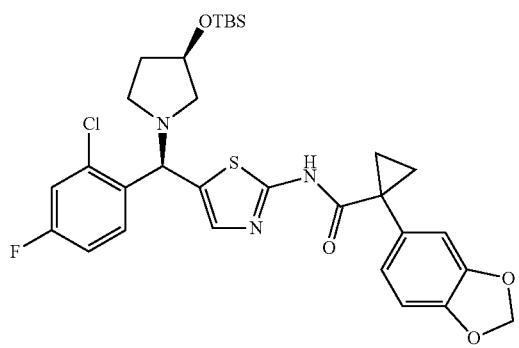

1-(Benzo[d][1,3]dioxol-5-yl)-N-(5-((R)-((R)-3-(tert-butyldimethylsilyloxy)pyrrolidin-1-yl)(2-chloro-4-fluorophenyl)methyl)thiazol-2-yl)cyclopropanecarboxamide was made by the procedure used for 1-(benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide, starting from of (R)-N-(5-(amino(2-chloro-4-fluorophenyl)methyl)thiazol-2-yl)-1-(benzo[d][1,3]dioxol-5-yl)cyclopropanecarboxamide and (R)-3-(tert-butyldimethylsilyloxy)-4-chlorobutanal (99%). $^1$H NMR (400 MHz, DMSO-$d_6$) δ 11.01 (s, 1H), 7.77 (dd, J=6.4, 8.8 Hz, 1H), 7.38-7.36 (m, 2H), 7.29 (td, J=8.5, 2.7 Hz, 1H), 6.94 (s, 1H), 6.85 (m, 2H), 5.99 (s, 2H), 4.99 (s, 1H), 4.38-4.34 (m, 1H), 2.83 (dd, J=6.2, 9.9 Hz, 1H), 2.58-2.54 (m, 1H), 2.46-2.42 (m, 1H), 2.14 (dd, J=3.7, 9.9 Hz, 1H), 2.05-1.99 (m, 1H), 1.68-1.57 (m, 1H), 1.43-1.40 (m, 2H), 1.12-1.10 (m, 2H), 0.82 (s, 9H), −0.00 (s, 3H), −0.02 (s, 3H); HPLC ret. time 3.60 min, 10-99% $CH_3CN$, 5 min run; ESI-MS 630.5 m/z (MH$^+$).

N-(5-((R)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide

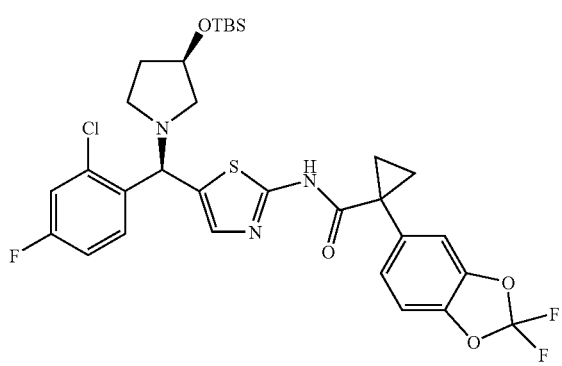

N-(5-((R)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide, starting from (R)-N-(5-(amino(2-chloro-4-fluorophenyl)methyl)thiazol-2-yl)-1-(2,2-difluorobenzo[d][1,3]dioxol-5-yl)cyclopropanecarboxamide and (R)-3-(tert-butyldimethylsilyloxy)-4-chlorobutanal (92%). $^1$H NMR (400 MHz, DMSO-$d_6$) δ 11.32 (s, 1H), 7.77 (dd, J=6.4, 8.8 Hz, 1H), 7.43 (d, J=1.4 Hz, 1H), 7.39-7.30 (m, 4H), 7.20 (dd, J=1.5, 8.3 Hz, 1H), 4.99 (s, 1H), 4.40-4.35 (m, 1H), 2.83 (dd, J=6.1, 9.9 Hz, 1H), 2.60-2.52 (m, 1H), 2.46-2.41 (m, 1H), 2.15 (dd, J=3.7, 9.9 Hz, 1H), 2.07-1.99 (m, 1H), 1.63-1.57 (m, 1H), 1.51-1.48 (m, 2H), 1.25-1.24 (m, 2H), 0.83 (s, 9H), 0.01 (s, 3H), −0.02 (s, 3H); HPLC ret. time 3.79 min, 10-99% $CH_3CN$, 5 min run; ESI-MS 666.3 m/z (MH$^+$).

1-(Benzo[d][1,3]dioxol-5-yl)-N-(5-((S)-((R)-3-(tert-butyldimethylsilyloxy)pyrrolidin-1-yl)(4-chloro-2-fluorophenyl)methyl)thiazol-2-yl)cyclopropanecarboxamide

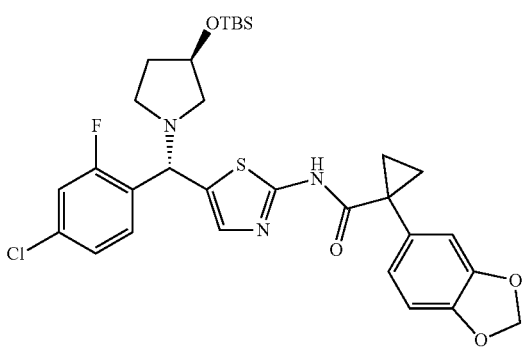

1-(Benzo[d][1,3]dioxol-5-yl)-N-(5-((S)-((R)-3-(tert-butyldimethylsilyloxy)pyrrolidin-1-yl)(4-chloro-2-fluorophenyl)methyl)thiazol-2-yl)cyclopropanecarboxamide was made by the procedure used for 1-(benzo[d][1,3]dioxol-5-yl)-N-(5-((S)-3-(tert-butyldimethylsilyloxy)pyrrolidin-1-yl)(2-chloro-4-fluorophenyl)methyl)thiazol-2-yl)cyclopropanecarboxamide, starting from of (S)-N-(5-(amino(4-chloro-2-fluorophenyl)methyl)thiazol-2-yl)-1-(benzo[d][1,3]dioxol-5-yl)cyclopropanecarboxamide and (R)-3-(tert-butyldimethylsilyloxy)-4-chlorobutanal (89%). $^1$H NMR (400 MHz, CDCl$_3$) δ 8.48 (s, 1H), 7.64 (t, J=8.1 Hz, 1H), 7.22 (s, 1H), 7.11 (dd, J=1.9, 8.4 Hz, 1H), 6.99 (dd, J=2.0, 9.9 Hz, 1H), 6.90-6.85 (m, 2H), 6.80 (d, J=7.9 Hz, 1H), 6.00 (s, 2H), 4.91 (s, 1H), 4.35-4.33 (m, 1H), 2.83 (dd, J=6.2, 9.8 Hz, 1H), 2.55-2.50 (m, 2H), 2.35 (dd, J=4.4, 9.8 Hz, 1H), 2.07-2.02 (m, 1H), 1.93-1.91 (m, 1H), 1.73-1.70 (m, 2H), 1.22-1.20 (m, 2H), 0.86 (s, 9H), 0.01 (s, 3H), 0.00 (s, 3H); HPLC ret. time 3.59 min, 10-99% $CH_3CN$, 5 min run; ESI-MS 630.5 m/z (MH$^+$).

N-(5-((S)-((R)-3-(tert-Butyldimethylsilyloxy)pyrrolidin-1-yl)(4-chloro-2-fluorophenyl)methyl)thiazol-2-yl)-1-(2,2-difluorobenzo[d][1,3]dioxol-5-yl)cyclopropanecarboxamide

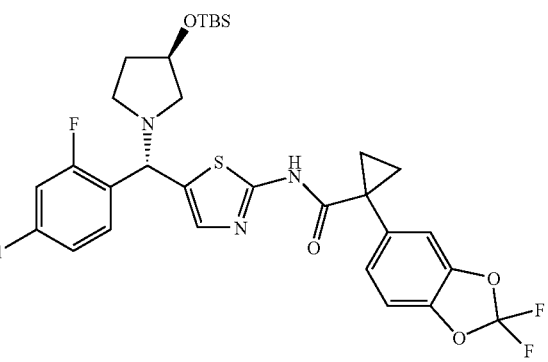

81

N-(5-((S)-((R)-3-(tert-Butyldimethylsilyloxy)pyrrolidin-1-yl)(4-chloro-2-fluorophenyl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-(((S)-3-(tert-butyldimethylsilyloxy)pyrrolidin-1-yl)(2-chloro-4-fluorophenyl)methyl)thiazol-2-yl)cyclopropanecarboxamide, starting from (S)-N-(5-(amino(4-chloro-2-fluorophenyl)methyl)thiazol-2-yl)-1-(2,2-difluorobenzo[d][1,3]dioxol-5-yl)cyclopropanecarboxamide and (R)-3-(tert-butyldimethylsilyloxy)-4-chlorobutanal (90%). $^1$H NMR (400 MHz, DMSO-$d_6$) δ 11.33 (s, 1H), 7.63 (t, J=8.2 Hz, 1H), 7.43-7.32 (m, 5H), 7.20 (dd, J=1.5, 8.3 Hz, 1H), 4.93 (s, 1H), 4.39-4.34 (m, 1H), 2.69 (dd, J=6.1, 9.8 Hz, 1H), 2.49-2.45 (m, 2H), 2.34 (dd, J=3.9, 9.9 Hz, 1H), 2.10-1.99 (m, 1H), 1.62-1.55 (m, 1H), 1.52-1.49 (m, 2H), 1.24-1.19 (m, 2H), 0.83 (s, 9H), 0.01 (s, 3H), −0.01 (s, 3H); HPLC ret. time 3.79 min, 10-99% $CH_3CN$, 5 min run; ESI-MS 666.3 m/z (MH$^+$).

1-(Benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide

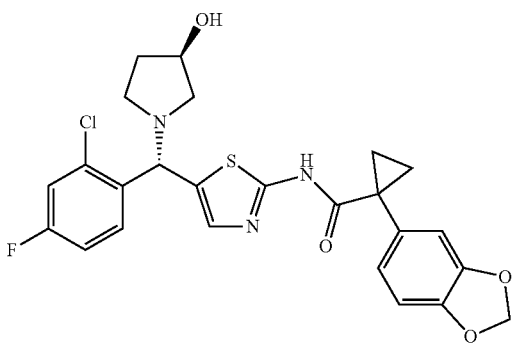

A mixture of 1-(benzo[d][1,3]dioxol-5-yl)-N-(5-((S)-((R)-3-(tert-butyldimethylsilyloxy)pyrrolidin-1-yl)(2-chloro-4-fluorophenyl)methyl)thiazol-2-yl)cyclopropanecarboxamide (365 mg, 0.58 mmol) and TBAF (1M in THF, 2.3 mL, 2.3 mmol) was stirred at room temperature overnight. The reaction was diluted with $H_2O$ and extracted with EtOAc. The combined organic layers were washed with brine and dried over $MgSO_4$. After the removal of solvent, the residue was purified by column chromatography (20-50% EtOAc/Hexane) to afford 1-(Benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide (183 mg, 61%, >99% de). $^1$H-NMR (400 MHz, DMSO-$d_6$) δ 8.41 (s, 1H), 7.72 (t, J=7.1 Hz, 1H), 7.20 (d, J=8.3 Hz, 2H), 6.95 (t, J=7.2 Hz, 2H), 6.80 (td, J=8.5, 1.6 Hz, 2H), 6.73 (d, J=7.9 Hz, 1H), 5.94 (s, 2H), 4.95 (s, 1H), 4.25 (s, 1H), 2.75 (s, 1H), 2.58-2.56 (m, 1H), 2.42 (s, 1H), 2.28-2.27 (m, 1H), 2.12-2.11 (m, 1H), 1.71-1.61 (m, 3H), 1.19-1.10 (m, 2H); HPLC ret. time 2.68 min, 10-99% $CH_3CN$, 5 min run; ESI-MS 516.2 m/z (MH$^+$).

82

N-(5-((S)-(2-Chloro-4-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide

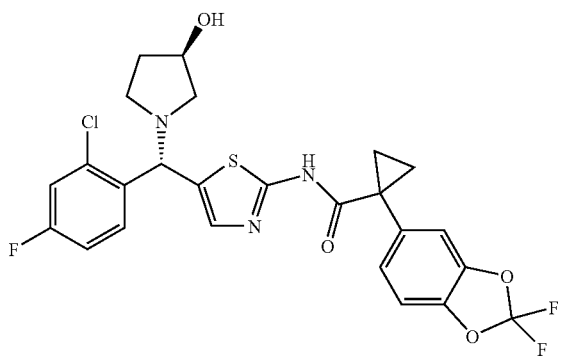

N-(5-((S)-(2-chloro-4-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide, starting from N-(5-((S)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide (77%). $^1$H NMR (400 MHz, DMSO-$d_6$) δ 8.36 (s, 1H), 7.80 (t, J=7.2 Hz, 1H), 7.30 (d, J=10.6 Hz, 1H), 7.17 (td, J=8.5, 1.7 Hz, 2H), 7.11-7.01 (m, 4H), 5.05 (s, 1H), 4.35-4.33 (m, 1H), 2.84-2.83 (m, 1H), 2.67-2.64 (m, 1H), 2.50 (dd, J=10.0, 4.9 Hz, 1H), 2.38-2.34 (m, 1H), 2.20 (dd, J=12.9, 5.8 Hz, 1H), 1.87-1.76 (m, 3H), 1.30-1.23 (m, 2H); HPLC ret. time 2.91 min, 10-99% $CH_3CN$, 5 min run; ESI-MS 552.4 m/z (MH$^+$).

1-(Benzo[d][1,3]dioxol-5-yl)-N-(5-((R)-(2-chloro-4-fluorophenyl)((R)-3-hydroxypyrrolidin-1-yl)methyl)thiazol-2-yl)cyclopropanecarboxamide

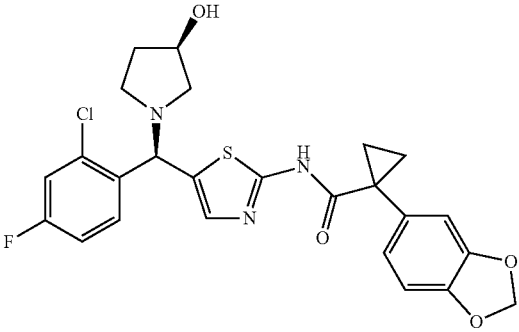

1-(Benzo[d][1,3]dioxol-5-yl)-N-(5-((R)-(2-chloro-4-fluorophenyl)((R)-3-hydroxypyrrolidin-1-yl)methyl)thiazol-2-yl)cyclopropanecarboxamide was made by the procedure used for 1-(benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide, starting from 1-(benzo[d][1,3]dioxol-5-yl)-N-(5-((R)-((R)-3-(tert-butyldimethylsilyloxy)pyrrolidin-1-yl)(2-chloro-4-fluorophenyl)methyl)thiazol-2-yl)cyclopropanecarboxamide (61%, >99% de). $^1$H NMR (400 MHz, DMSO-$d_6$) δ 11.01 (s, 1H), 7.80 (dd, J=6.4, 8.8 Hz, 1H), 7.39-7.36 (m, 2H), 7.30 (td, J=8.5, 2.6 Hz, 1H), 6.95 (s, 1H), 6.85 (s, 2H), 6.00 (s, 2H), 4.94 (s, 1H), 4.72 (d, J=4.3 Hz, 1H), 4.19-4.18 (m, 1H), 2.70-2.66 (m, 1H), 2.60-2.56 (m, 1H), 2.34-2.30 (m, 1H), 2.20 (dd, J=3.1, 9.9 Hz, 1H), 2.00-1.95 (m, 1H), 1.60-1.57 (m, 1H), 1.44-1.41 (m, 2H), 1.14-1.08 (m, 2H); HPLC ret. time 2.72 min, 10-99% CH$_3$CN, 5 min run; ESI-MS 516.3 m/z (MH$^+$).

N-(5-((R)-(2-Chloro-4-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide

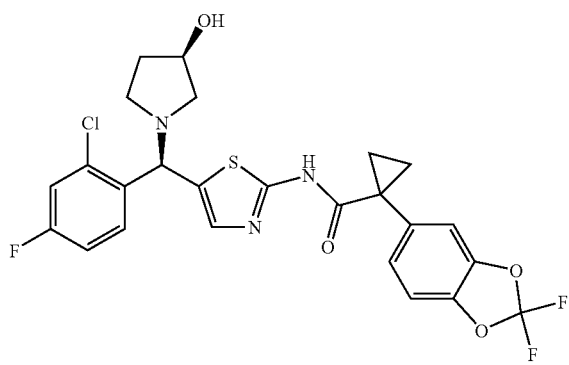

N-(5-((R)-(2-Chloro-4-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide, starting from N-(5-((R)-((R)-3-(tert-butyldimethylsilyloxy)pyrrolidin-1-yl)(2-chloro-4-fluorophenyl)methyl)thiazol-2-yl)-1-(2,2-difluorobenzo[d][1,3]dioxol-5-yl)cyclopropanecarboxamide (73%, >99% de). $^1$H NMR (400 MHz, DMSO-$d_6$) δ 11.32 (s, 1H), 7.80 (dd, J=6.4, 8.8 Hz, 1H), 7.43 (d, J=1.4 Hz, 1H), 7.39-7.28 (m, 4H), 7.20 (dd, J=1.6, 8.3 Hz, 1H), 4.94 (s, 1H), 4.72 (d, J=4.3 Hz, 1H), 4.20-4.19 (m, 1H), 2.71-2.67 (m, 1H), 2.63-2.57 (m, 1H), 2.34-2.29 (m, 1H), 2.20 (dd, J=3.2, 9.8 Hz, 1H), 2.02-1.93 (m, 1H), 1.62-1.54 (m, 1H), 1.54-1.48 (m, 2H), 1.23-1.17 (m, 2H); HPLC ret. time 2.94 min, 10-99% CH$_3$CN, 5 min run; ESI-MS 552.5 m/z (MH$^+$).

1-(Benzo[d][1,3]dioxol-5-yl)-N-(5-((S)-(4-chloro-2-fluorophenyl)((R)-3-hydroxypyrrolidin-1-yl)methyl)thiazol-2-yl)cyclopropanecarboxamide

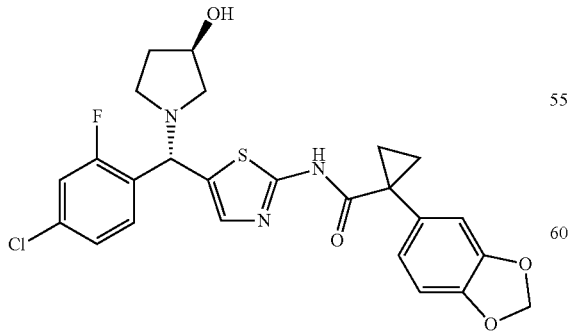

1-(Benzo[d][1,3]dioxol-5-yl)-N-(5-((S)-(4-chloro-2-fluorophenyl)((R)-3-hydroxypyrrolidin-1-yl)methyl)thiazol-2-yl)cyclopropanecarboxamide was made by the procedure used for 1-(benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide, starting from 1-(benzo[d][1,3]dioxol-5-yl)-N-(5-((S)-((R)-3-(tert-butyldimethylsilyloxy)pyrrolidin-1-yl)(4-chloro-2-fluorophenyl)methyl)thiazol-2-yl)cyclopropanecarboxamide (37%, >99% de). $^1$H NMR (400 MHz, CDCl$_3$) δ 8.48 (s, 1H), 7.62 (t, J=8.1 Hz, 1H), 7.22 (s, 1H), 7.13 (dd, J=1.9, 8.4 Hz, 1H), 7.01 (dd, J=2.1, 9.9 Hz, 1H), 6.90-6.85 (m, 2H), 6.81 (d, J=7.9 Hz, 1H), 6.01 (s, 2H), 4.92 (s, 1H), 4.34-4.28 (m, 1H), 2.86-2.80 (m, 1H), 2.63 (d, J=10.1 Hz, 1H), 2.50-2.46 (m, 1H), 2.34-2.23 (m, 1H), 2.21-2.12 (m, 1H), 1.80-1.70 (m, 4H), 1.24-1.18 (m, 2H); HPLC ret. time 2.77 min, 10-99% CH$_3$CN, 5 min run; ESI-MS 516.3 m/z (MH$^+$).

N-(5-((S)-(4-chloro-2-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide

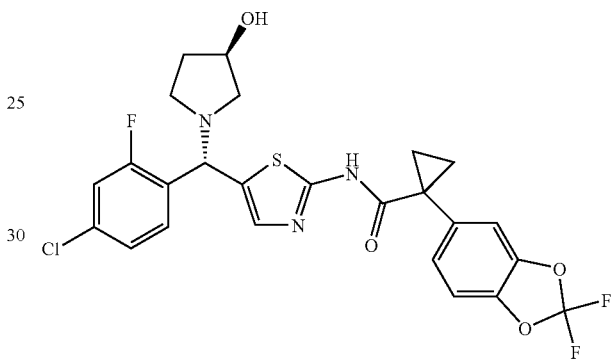

N-(5-((S)-(4-chloro-2-fluorophenyl)((R)-3-hydroxypyrrolidin-1-yl)methyl)thiazol-2-yl)-1-(2,2-difluorobenzo[d][1,3]dioxol-5-yl)cyclopropanecarboxamide was made by the procedure used for 1-(benzo[d][1,3]dioxol-5-yl)-N-(5-((S)-(2-chloro-4-fluorophenyl)((R)-3-hydroxypyrrolidin-1-yl)methyl)thiazol-2-yl)cyclopropanecarboxamide, starting from N-(5-((S)-((R)-3-(tert-butyldimethylsilyloxy)pyrrolidin-1-yl)(4-chloro-2-fluorophenyl)methyl)thiazol-2-yl)-1-(2,2-difluorobenzo[d][1,3]dioxol-5-yl)cyclopropanecarboxamide (78%, >99% de). $^1$H NMR (400 MHz, DMSO-$d_6$) δ 11.32 (s, 1H), 7.66 (t, J=8.1 Hz, 1H), 7.43 (d, J=1.5 Hz, 1H), 7.39-7.33 (m, 4H), 7.20 (dd, J=1.6, 8.3 Hz, 1H), 4.88 (s, 1H), 4.75 (d, J=4.4 Hz, 1H), 4.21-4.16 (m, 1H), 2.57 (dd, J=6.1, 9.8 Hz, 1H), 2.51-2.44 (m, 1H), 2.41-2.33 (m, 2H), 2.04-1.95 (m, 1H), 1.60-1.45 (m, 3H), 1.24-1.15 (m, 2H); HPLC ret. time 2.97 min, 10-99% CH$_3$CN, 5 min run; ESI-MS 552.5 m/z (MH$^+$).

(R)-N-((R)-(2-Amino-4-methylthiazol-5-yl)(2-chlorophenyl)methyl)-2-methylpropane-2-sulfinamide and (R)-N-((S)-(2-Amino-4-methylthiazol-5-yl)(2-chlorophenyl)methyl)-2-methylpropane-2-sulfinamide

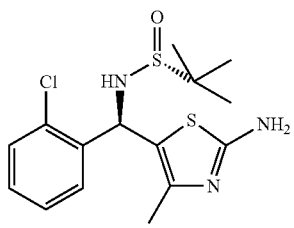

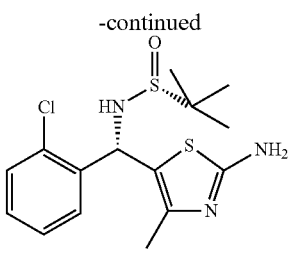

To a solution of (R)-tert-Butyl 5-((2-chlorophenyl)(1,1-dimethylethylsulfinamido)methyl)-4-methylthiazol-2-ylcarbamate, (19.0 g, 41.6 mmol) in $CH_2Cl_2$ (83 mL) was added TFA (83 mL). The reaction was stirred at room temperature for 1 h. The reaction was concentrated and then partitioned between $CH_2Cl_2$ and saturated aqueous $NaHCO_3$ solution. The aqueous layer was basified to pH>12 by adding 1N NaOH solution and extracted with $CH_2Cl_2$. The combined organic layers were dried over $MgSO_4$ and concentrated. The crude product was adsorbed onto silica gel and purified by column chromatography (70-100% EtOAc/hexanes. The EtOAc contained 2% $NH_4OH$ and was stirred to maintain the mixture) to provide (R)-N-((R)-(2-amino-4-methylthiazol-5-yl)(2-chlorophenyl)methyl)-2-methylpropane-2-sulfinamide and (R)-N-((S)-(2-amino-4-methylthiazol-5-yl)(2-chlorophenyl)methyl)-2-methylpropane-2-sulfinamide and a mixture of both diastereomers (7.1 g, 47%). First eluted product (Isomer A) (white solid, 3.0 g, 20%, >99% de); $^1$H NMR (400 MHz, $CDCl_3$) δ 7.60 (dd, J=1.6, 7.7 Hz, 1H), 7.38-7.22 (m, 3H), 6.15 (d, J=2.5 Hz, 1H), 4.94 (s, 2H), 3.87 (d, J=2.3 Hz, 1H), 2.34 (s, 3H), 1.27 (s, 9H); HPLC ret. time 3.08 min, 10-99% $CH_3CN$, 15 min run; ESI-MS 358.3 m/z (MH$^+$). Second eluted product (Isomer B) (yellow waxy solid, 5.0 g, 33%. 98% de); $^1$H NMR (400 MHz, $CDCl_3$) δ 7.64 (dd, J=7.7, 1.7 Hz, 1H), 7.36 (dd, J=7.8, 1.4 Hz, 1H), 7.32-7.21 (m, 2H), 6.19 (d, J=1.8 Hz, 1H), 4.86 (s, 2H), 3.65 (d, J=1.2 Hz, 1H), 2.33 (s, 3H), 1.26 (s, 9H); HPLC ret. time 3.77 min, 10-99% $CH_3CN$, 15 min run; ESI-MS 358.3 m/z (MH$^+$).

(R)-N-((R)-(2-aminothiazol-5-yl)(3,4-dichlorophenyl)methyl)-2-methylpropane-2-sulfinamide and (R)-N-((S)-(2-aminothiazol-5-yl)(3,4-dichlorophenyl)methyl)-2-methylpropane-2-sulfinamide

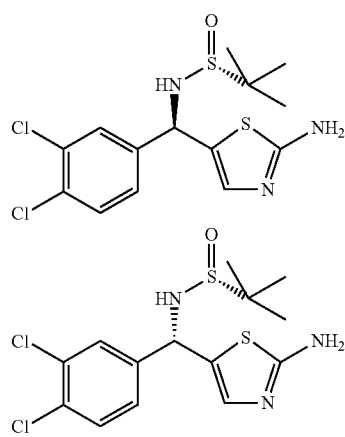

(R)-N-(S)-1-(2-Aminothiazol-5-yl)-1-(3,4-dichlorophenyl)methyl)-1,1-dimethylethylsulfinamide and (R)-N-(R)-1-(2-aminothiazol-5-yl)-1-(3,4-dichlorophenyl)methyl)-1,1-dimethylethylsulfinamide were made by the procedure for (R)-N-((R)-(2-amino-4-methylthiazol-5-yl)(2-chlorophenyl)methyl)-2-methylpropane-2-sulfinamide and (R)-N-((S)-(2-amino-4-methylthiazol-5-yl)(2-chlorophenyl)methyl)-2-methylpropane-2-sulfinamide starting from (R)-tert-butyl 5-((3,4-dichlorophenyl)(1,1-dimethylethylsulfinamido)methyl)thiazol-2-ylcarbamate.
The crude product was purified by column chromatography (5% EtOH/EtOAc elutes Isomer A, 20% EtOH/EtOAc elutes Isomer B). Isomer A (yellow solid, 5.67 g, 35%, >99% de); $^1$H NMR (400 MHz, $CDCl_3$) δ 7.49 (d, J=2.1 Hz, 1H), 7.44 (d, J=8.3 Hz, 1H), 7.25 (dd, J=2.2, 8.5 Hz, 1H), 6.95 (s, 1H), 5.63 (d, J=3.5 Hz, 1H), 5.03 (s, 2H), 3.84 (d, J=3.5 Hz, 1H), 1.26 (s, 9H); HPLC ret. time 2.37 min, 10-99% $CH_3CN$, 5 min run; ESI-MS 378.0 m/z (MH$^+$). Isomer B (yellow solid, 3.64 g, 23%, 96% de); $^1$H NMR (400 MHz, $CDCl_3$) ☐ 7.50 (d, J=2.1 Hz, 1H), 7.44 (d, J=8.3 Hz, 1H), 7.25 (dd, J=2.1, 8.5 Hz, 1H), 6.88 (d, J=0.5 Hz, 1H), 5.65 (d, J=2.5 Hz, 1H), 5.02 (s, 2H), 3.88 (d, J=2.3 Hz, 1H), 1.26 (s, 9H); HPLC ret. time 2.50 min, 10-99% $CH_3CN$, 5 min run; ESI-MS 378.2 m/z (MH$^+$).

1-(Benzo[d][1,3]dioxol-5-yl)-N-(5-((R)-(2-chlorophenyl)((R)-1,1-dimethylethylsulfinamido)methyl)-4-methylthiazol-2-yl)cyclopropanecarboxamide and 1-(Benzo[d][1,3]dioxol-5-yl)-N-(5-((S)-(2-chlorophenyl)((R)-1,1-dimethylethylsulfinamido)methyl)-4-methylthiazol-2-yl)cyclopropanecarboxamide

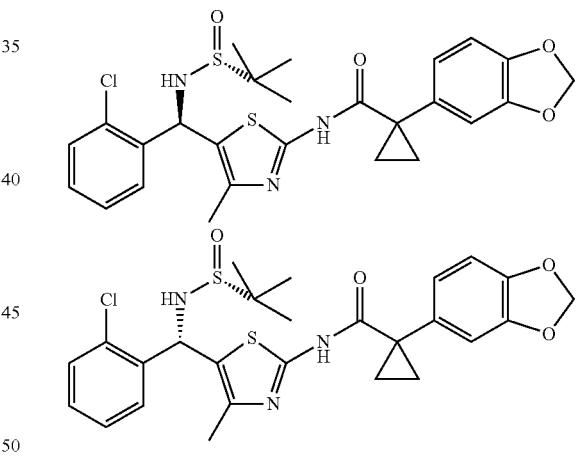

To 1-(benzo[d][1,3]dioxol-5-yl)cyclopropanecarboxylic acid (864 mg, 4.2 mmol) was slowly added $SOCl_2$ (916 μL, 12.6 mmol) followed by DMF (3 drops). The reaction mixture was heated at 60° C. for 0.5 h. The excess $SOCl_2$ was removed under vacuum. The acid chloride was then dissolved in anhydrous $CH_2Cl_2$ (6 mL) and was slowly added to a solution of (R)-N-((2-amino-4-methylthiazol-5-yl)(2-chlorophenyl)methyl)-2-methylpropane-2-sulfinamide (Isomer A) (1.35 g, 3.8 mmol) and $Et_3N$ (2.92 mL, 21.0 mmol) in anhydrous $CH_2Cl_2$ (18 mL). The reaction mixture was stirred at room temperature for 18 h, diluted with $CH_2Cl_2$ and washed with 1N HCl solution, saturated aqueous $NaHCO_3$ solution and brine. The organic layer was dried over $MgSO_4$ and concentrated to provide 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A) as an orange solid (1.54 g, 75%) that was used without further purification. HPLC ret. time 3.59 min, 10-99% CH₃CN, 5 min run; ESI-MS 546.5 m/z (MH⁺).

1-(Benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer B), was made by the procedure used for Isomer A starting from 1-(benzo[d][1,3]dioxol-5-yl)cyclopropanecarboxylic acid and (R)-N-((2-amino-4-methylthiazol-5-yl)(2-chlorophenyl)methyl)-2-methylpropane-2-sulfinamide (Isomer B). The crude product was adsorbed onto silica gel and purified by column chromatography (25-60% EtOAc/hexanes) to yield the product as light orange solid (62%). ¹H NMR (400 MHz, CDCl₃) δ 8.48 (s, 1H), 7.70 (dd, J=7.8, 1.6 Hz, 1H), 7.34-7.20 (m, 3H), 6.88-6.79 (m, 3H), 6.26 (d, J=1.9 Hz, 1H), 6.01 (s, 2H), 3.55 (d, J=1.7 Hz, 1H), 2.40 (s, 3H), 1.68 (m, 2H), 1.28-1.18 (m, 11H); HPLC ret. time 3.69 min, 10-99% CH₃CN, 5 min run; ESI-MS 546.5 m/z (MH⁺).

N-(5-((R)-(2-Chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide and N-(5-((S)-(2-Chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide

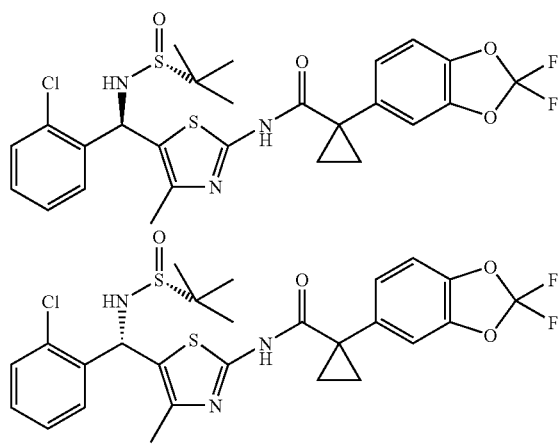

N-(5-((2-Chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide (Isomer A), was made by the procedure used for 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A) starting from 1-(2,2-difluorobenzo[d][1,3]dioxol-5-yl)cyclopropanecarboxylic acid and (R)-N-((2-amino-4-methylthiazol-5-yl)(2-chlorophenyl)methyl)-2-methylpropane-2-sulfinamide (Isomer A). The crude product was adsorbed onto silica gel and purified by column chromatography (25-100% EtOAc/hexanes) to yield an orange solid (55%). ¹H NMR (400 MHz, CDCl₃) δ 8.36 (s, 1H), 7.67 (dd, J=7.7, 1.6 Hz, 1H), 7.35-7.21 (m, 3H), 7.17-7.07 (m, 3H), 6.21 (d, J=2.5 Hz, 1H), 3.80 (d, J=2.4 Hz, 1H), 2.41 (s, 3H), 1.80-1.70 (m, 2H), 1.26-1.18 (m, 11H); HPLC ret. time 3.81 min, 10-99% CH₃CN, 5 min run; ESI-MS 582.3 m/z (MH⁺).

N-(5-((2-Chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide (Isomer B), was made by the procedure used for 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A) starting from 1-(2,2-difluorobenzo[d][1,3]dioxol-5-yl)cyclopropanecarboxylic acid and (R)-N-((2-amino-4-methylthiazol-5-yl)(2-chlorophenyl)methyl)-2-methylpropane-2-sulfinamide (Isomer B). The crude product was adsorbed onto silica gel and purified by column chromatography (30-80% EtOAc/hexanes) to yield an orange solid (37%) ¹H NMR (400 MHz, CDCl₃) δ 8.33 (s, 1H), 7.70 (dd, J=7.8, 1.7 Hz, 1H), 7.35-7.20 (m, 3H), 7.16-7.07 (m, 3H), 6.26 (d, J=2.0 Hz, 1H), 3.55 (d, J=1.8 Hz, 1H), 2.39 (s, 3H), 1.79-1.71 (m, 2H), 1.28-1.21 (m, 11H); HPLC ret. time 3.98 min, 10-99% CH₃CN, 5 min run; ESI-MS 582.3 m/z (MH⁺).

1-(Benzo[d][1,3]dioxol-5-yl)-N-(5-((R)-(3,4-dichlorophenyl)((R)-1,1-dimethylethylsulfinamido)methyl)thiazol-2-yl)cyclopropanecarboxamide and 1-(Benzo[d][1,3]dioxol-5-yl)-N-(5-((S)-(3,4-dichlorophenyl)((R)-1,1-dimethylethylsulfinamido)methyl)thiazol-2-yl)cyclopropanecarboxamide

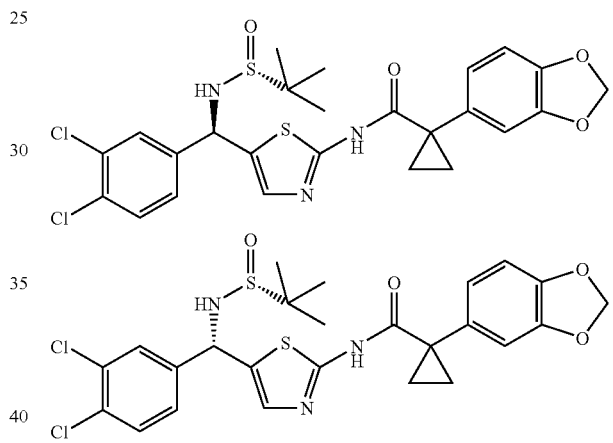

1-(Benzo[d][1,3]dioxol-5-yl)-N-(5-((3,4-dichlorophenyl)((R)-1,1-dimethylethylsulfinamido)methyl)thiazol-2-yl)cyclopropanecarboxamide (Isomer A), was made by the procedure used for 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A) starting from 1-(benzo[d][1,3]dioxol-5-yl)cyclopropanecarboxylic acid, (COCl)₂ and (R)-N-((2-aminothiazol-5-yl)(3,4-dichlorophenyl)methyl)-2-methylpropane-2-sulfinamide (Isomer A). The crude product was purified by column chromatography (60-80% EtOAc/Hexane) to provide a yellow solid (2.70 g, 72%). ¹H NMR (400 MHz, CDCl₃) δ 8.57 (s, 1H), 7.49 (d, J=2.1 Hz, 1H), 7.43 (d, J=8.3 Hz, 1H), 7.28-7.26 (m, 2H), 6.90 (dd, J=1.8, 7.9 Hz, 1H), 6.87 (d, J=1.6 Hz, 1H), 6.82 (d, J=7.9 Hz, 1H), 6.02 (s, 2H), 5.74 (d, J=3.1 Hz, 1H), 3.73 (d, J=3.2 Hz, 1H), 1.73-1.71 (m, 2H), 1.28-1.21 (m, 11H); HPLC ret. time 3.80 min, 10-99% CH₃CN, 5 min run; ESI-MS 566.2 m/z (MH⁺).

1-(Benzo[d][1,3]dioxol-5-yl)-N-(5-((3,4-dichlorophenyl)((R)-1,1-dimethylethylsulfinamido)methyl)thiazol-2-yl)cyclopropanecarboxamide (Isomer B), was made by the procedure used for 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A) starting from 1-(benzo[d][1,3]dioxol-5-yl)cyclopropanecarboxylic acid, (COCl)₂ and (R)-N-((2-aminothiazol-5-yl)(3,4-dichlorophenyl)methyl)-2-methylpropane-2-sulfinamide (Isomer B). The crude product was purified by column chromatography (60-100% EtOAc/Hexane) to provide a yellow solid (2.65 g, 71%). ¹H NMR (400 MHz, CDCl₃) δ 8.59 (s, 1H), 7.52 (d, J=2.1 Hz, 1H), 7.42 (d, J=8.3 Hz, 1H), 7.29-7.26 (m, 2H), 6.90-6.86 (m, 2H), 6.81 (d, J=7.9 Hz, 1H), 6.02 (dd, J=1.4, 1.9 Hz, 2H), 5.77 (d, J=1.8 Hz, 1H), 3.72 (d, J=1.9 Hz, 1H), 1.72 (dd, J=3.2, 6.7 Hz, 2H), 1.28-1.22 (m, 11H); HPLC ret. time 3.91 min, 10-99% CH₃CN, 5 min run; ESI-MS 566.4 m/z (MH⁺).

(R)-N-(5-(Amino(2-chlorophenyl)methyl)-4-methylthiazol-2-yl)-1-(benzo[d][1,3]dioxol-5-yl)cyclopropanecarboxamide and (S)-N-(5-(Amino(2-chlorophenyl)methyl)-4-methylthiazol-2-yl)-1-(benzo[d][1,3]dioxol-5-yl)cyclopropanecarboxamide

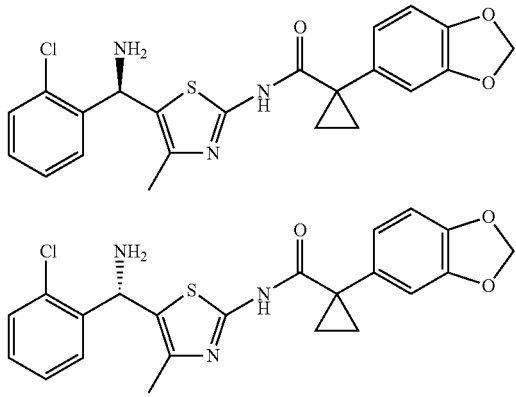

To a solution of 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer A), (1.47 g, 2.69 mmol) in MeOH (13 mL) was added 4 M HCl in dioxane (4 mL, 16 mmol). The reaction mixture was stirred at room temperature for 3 h and then concentrated. The crude product was dissolved in CH₂Cl₂ and washed with saturated aqueous NaHCO₃ solution (×2) and brine, then dried over MgSO₄ and concentrated. The crude product was adsorbed onto silica gel and purified by column chromatography (70-100% EtOAc/hexanes) to provide N-(5-(amino(2-chlorophenyl)methyl)-4-methylthiazol-2-yl)-1-(benzo[d][1,3]dioxol-5-yl)cyclopropanecarboxamide (Isomer A), as an orange solid (540 mg, 45%). ¹H NMR (400 MHz, DMSO-d6) δ 7.80 (d, J=7.9 Hz, 1H), 7.40-7.36 (m, 2H), 7.27 (m, 1H), 6.94 (s, 1H), 6.85 (m, 2H), 6.00 (s, 2H), 5.56 (s, 1H), 2.19 (s, 3H), 1.40 (m, 2H), 1.10 (m, 2H); HPLC ret. time 2.65 min, 10-99% CH₃CN, 5 min run; ESI-MS 442.5 m/z (MH⁺).

N-(5-(Amino(2-chlorophenyl)methyl)-4-methylthiazol-2-yl)-1-(benzo[d][1,3]dioxol-5-yl)cyclopropanecarboxamide (Isomer B) was made by the procedure used for Isomer A starting from 1-(benzo[d][1,3]dioxol-5-yl)-N-(5-((2-chlorophenyl)((R)-1,1-dimethylethylsulfinamido)methyl)-4-methylthiazol-2-yl)cyclopropanecarboxamide (Isomer B) (90%). ¹H NMR (400 MHz, DMSO-d6) δ 7.80 (d, J=7.8 Hz, 1H), 7.40-7.36 (m, 2H), 7.27 (m, 1H), 6.94 (s, 1H), 6.85 (m, 2H), 6.00 (s, 2H), 5.56 (s, 1H), 2.19 (s, 3H), 1.40 (m, 2H), 1.10 (m, 2H); HPLC ret. time 2.69 min, 10-99% CH₃CN, 5 min run; ESI-MS 442.3 m/z (MH⁺).

(R)-N-(5-(Amino(2-chlorophenyl)methyl)-4-methylthiazol-2-yl)-1-(2,2-difluorobenzo[d][1,3]dioxol-5-yl)cyclopropanecarboxamide and (S)-N-(5-(Amino(2-chlorophenyl)methyl)-4-methylthiazol-2-yl)-1-(2,2-difluorobenzo[d][1,3]dioxol-5-yl)cyclopropanecarboxamide

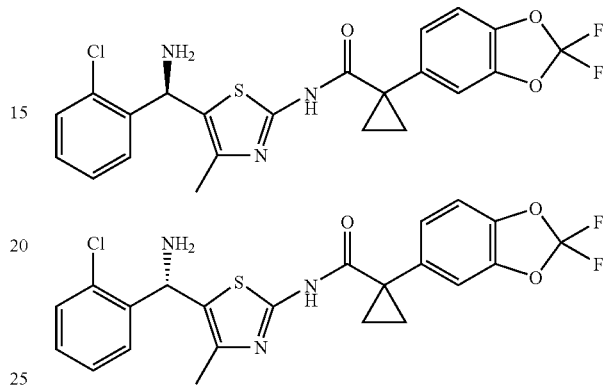

N-(5-(Amino(2-chlorophenyl)methyl)-4-methylthiazol-2-yl)-1-(2,2-difluorobenzo[d][1,3]dioxol-5-yl)cyclopropanecarboxamide (Isomer A) was made by the procedure used for N-(5-(amino(2-chlorophenyl)methyl)-4-methylthiazol-2-yl)-1-(benzo[d][1,3]dioxol-5-yl)cyclopropanecarboxamide (Isomer A) starting from N-(5-((2-chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide (Isomer A) (83%). ¹H NMR (400 MHz, DMSO-d6) δ 7.81 (m, 1H), 7.41-7.32 (m, 4H), 7.27 (m, 1H), 7.18 (dd, J=1.7, 8.3 Hz, 1H), 5.57 (s, 1H), 2.20 (s, 3H), 1.48 (m, 2H), 1.17 (m, 2H); HPLC ret. time 2.84 min, 10-99% CH₃CN, 5 min run; ESI-MS 478.1 m/z (MH⁺).

N-(5-(Amino(2-chlorophenyl)methyl)-4-methylthiazol-2-yl)-1-(2,2-difluorobenzo[d][1,3]dioxol-5-yl)cyclopropanecarboxamide (Isomer B) was made by the procedure used for N-(5-(amino(2-chlorophenyl)methyl)-4-methylthiazol-2-yl)-1-(benzo[d][1,3]dioxol-5-yl)cyclopropanecarboxamide (Isomer A) starting from N-(5-((2-chlorophenyl)((R)-1,1-dimethylethylsulfinamido)methyl)-4-methylthiazol-2-yl)-1-(2,2-difluorobenzo[d][1,3]dioxol-5-yl)cyclopropanecarboxamide (Isomer B) (65%). ¹H NMR (400 MHz, DMSO-d6) δ 7.81 (m, 1H), 7.41-7.32 (m, 4H), 7.28 (m, 1H), 7.18 (dd, J=1.7, 8.3 Hz, 1H), 5.56 (s, 1H), 2.19 (s, 3H), 1.48 (m, 2H), 1.18 (m, 2H); HPLC ret. time 2.84 min, 10-99% CH₃CN, 5 min run; ESI-MS 478.1 m/z (MH⁺).

(R)-N-(5-(Amino(3,4-dichlorophenyl)methyl)thiazol-2-yl)-1-(benzo[d][1,3]dioxol-5-yl)cyclopropanecarboxamide and (S)-N-(5-(Amino(3,4-dichlorophenyl)methyl)thiazol-2-yl)-1-(benzo[d][1,3]dioxol-5-yl)cyclopropanecarboxamide

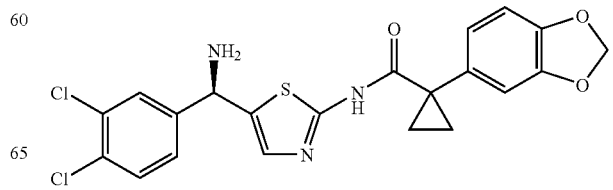

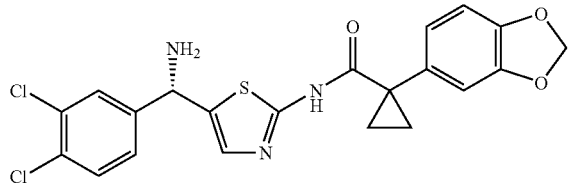

N-(5-(Amino(3,4-dichlorophenyl)methyl)thiazol-2-yl)-1-(benzo[d][1,3]dioxol-5-yl)cyclopropanecarboxamide (Isomer A) was made by the procedure used for N-(5-(amino(2-chlorophenyl)methyl)-4-methylthiazol-2-yl)-1-(benzo[d][1,3]dioxol-5-yl)cyclopropanecarboxamide (Isomer A) starting from 1-(benzo[d][1,3]dioxol-5-yl)-N-(5-(((3,4-dichlorophenyl)((R)-1,1-dimethylethylsulfinamido)methyl)thiazol-2-yl)cyclopropanecarboxamide (Isomer A). The crude product was purified by column chromatography (0-20% MeOH/DCM) (98%). $^1$H NMR (400 MHz, DMSO-$d_6$) δ 10.8 (bs, 1H), 7.70 (d, J=2.0 Hz, 1H), 7.58 (d, J=8.3 Hz, 1H), 7.40 (dd, J=2.0, 8.4 Hz, 1H), 7.16 (d, J=0.8 Hz, 1H), 6.96 (s, 1H), 6.86 (d, J=0.9 Hz, 2H), 6.01 (s, 2H), 5.29 (s, 1H), 1.44-1.42 (m, 2H), 1.13-1.10 (m, 2H); HPLC ret. time 2.81 min, 10-99% CH$_3$CN, 5 min run; ESI-MS 462.3 m/z (MH$^+$).

N-(5-(Amino(3,4-dichlorophenyl)methyl)thiazol-2-yl)-1-(benzo[d][1,3]dioxol-5-yl)cyclopropanecarboxamide (Isomer B) was made by the procedure used for (Isomer A) starting from 1-(benzo[d][1,3]dioxol-5-yl)-N-(5-((3,4-dichlorophenyl)((R)-1,1-dimethylethylsulfinamido)methyl)thiazol-2-yl)cyclopropanecarboxamide (Isomer B) (quant.). $^1$H NMR (400 MHz, DMSO-$d_6$) δ 10.8 (bs, 1H), 7.70 (d, J=2.0 Hz, 1H), 7.58 (d, J=8.3 Hz, 1H), 7.40 (dd, J=2.0, 8.4 Hz, 1H), 7.16 (d, J=0.7 Hz, 1H), 6.96 (s, 1H), 6.86 (d, J=0.9 Hz, 2H), 6.01 (s, 2H), 5.29 (s, 1H), 1.44-1.42 (m, 2H), 1.13-1.10 (m, 2H); HPLC ret. time 2.81 min, 10-99% CH$_3$CN, 5 min run; ESI-MS 462.1 m/z (MH$^+$).

1-(Benzo[d][1,3]dioxol-5-yl)-N-(5-((R)-((S)-3-(tert-butyldimethylsilyloxy)pyrrolidin-1-yl)(2-chlorophenyl)methyl)-4-methylthiazol-2-yl)cyclopropanecarboxamide and 1-(Benzo[d][1,3]dioxol-5-yl)-N-(5-((S)-((S)-3-(tert-butyldimethylsilyloxy)pyrrolidin-1-yl)(2-chlorophenyl)methyl)-4-methylthiazol-2-yl)cyclopropanecarboxamide

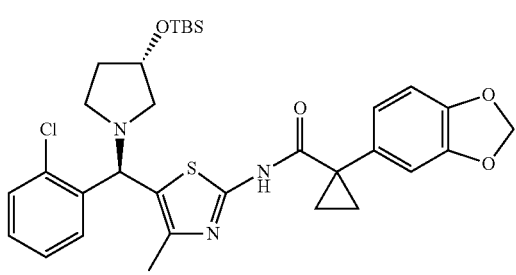

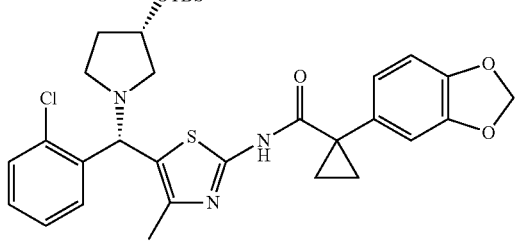

To a solution of N-(5-(amino(2-chlorophenyl)methyl)-4-methylthiazol-2-yl)-1-(benzo[d][1,3]dioxol-5-yl)cyclopropanecarboxamide (Isomer A) (450 mg, 1.02 mmol) in MeOH (5 mL) was added (S)-3-(tert-butyldimethylsilyloxy)-4-chlorobutanal (289 mg, 1.22 mmol). The reaction mixture was stirred at room temperature for 20 min before NaBH$_4$ (58 mg, 1.53 mmol) was added. Stirring was continued at room temperature for 3 h. After approximately 1 h some precipitate/gum started to form in the reaction solution so MeOH (5 mL) and CH$_2$Cl$_2$ (2 mL) were added to keep everything in solution. The reaction was diluted with H$_2$O and extracted with EtOAc. The combined organic layers was washed with brine, dried over MgSO$_4$ and concentrated. The residue was adsorbed onto silica gel and purified by column chromatography (0-25% EtOAc/hexanes) to afford 1-(benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer A) as a pale yellow solid (470 mg, 74%). $^1$H NMR (400 MHz, CDCl$_3$) δ 8.40 (s, 1H), 7.83 (dd, J=8.1, 1.6 Hz, 1H), 7.28-7.25 (m, 2H), 7.13 (m, 1H), 6.88-6.83 (m, 2H), 6.79 (d, J=7.9 Hz, 1H), 6.00 (s, 2H), 5.08 (s, 1H), 4.33 (m, 1H), 2.94 (dd, J=9.9, 6.3 Hz, 1H), 2.67 (td, J=8.3, 3.4 Hz, 1H), 2.53 (q, J=8.4 Hz, 1H), 2.37 (s, 3H), 2.17 (dd, J=9.9, 4.7 Hz, 1H), 2.00 (m, 1H), 1.74-1.61 (m, 3H), 1.17 (m, 2H), 0.86 (m, 9H), 0.01 (s, 3H), −0.01 (s, 3H); HPLC ret. time 3.45 min, 10-99% CH$_3$CN, 5 min run; ESI-MS 626.5 m/z (MH$^+$).

1-(Benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer B) was made by the procedure used for (Isomer A) starting from N-(5-(amino(2-chlorophenyl)methyl)-4-methylthiazol-2-yl)-1-(benzo[d][1,3]dioxol-5-yl)cyclopropanecarboxamide (Isomer B) and (S)-3-(tert-butyldimethylsilyloxy)-4-chlorobutanal (81%). $^1$H NMR (400 MHz, CDCl$_3$) δ 8.41 (s, 1H), 7.86 (dd, J=7.2, 0.7 Hz, 1H), 7.27-7.24 (m, 2H), 7.12 (m, 1H), 6.88-6.84 (m, 2H), 6.79 (d, J=7.9 Hz, 1H), 6.00 (s, 2H), 5.05 (s, 1H), 4.34 (m, 1H), 2.84 (dd, J=9.7, 6.3 Hz, 1H), 2.56-2.46 (m, 2H), 2.37-2.32 (m, 4H), 2.03 (m, 1H), 1.74-1.62 (m, 3H), 1.18 (m, 2H), 0.86 (m, 9H), 0.02 (s, 3H), 0.00 (s, 3H); HPLC ret. time 3.54 min, 10-99% CH$_3$CN, 5 min run; ESI-MS 626.3 m/z (MH$^+$).

N-(5-((R)-((S)-3-(tert-Butyldimethylsilyloxy)pyrrolidin-1-yl)(2-chlorophenyl)methyl)-4-methylthiazol-2-yl)-1-(2,2-difluorobenzo[d][1,3]dioxol-5-yl)cyclopropanecarboxamide and N-(5-((S)-((S)-3-(tert-Butyldimethylsilyloxy)pyrrolidin-1-yl)(2-chlorophenyl)methyl)-4-methylthiazol-2-yl)-1-(2,2-difluorobenzo[d][1,3]dioxol-5-yl)cyclopropanecarboxamide

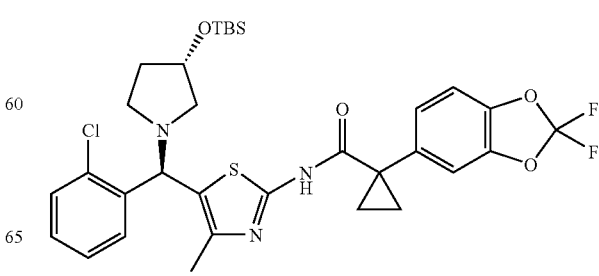

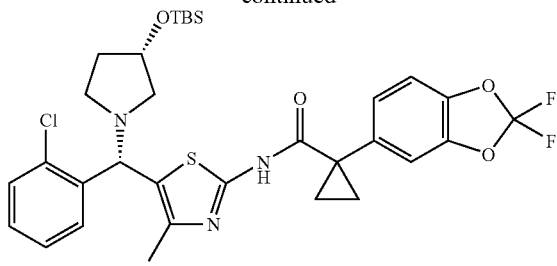
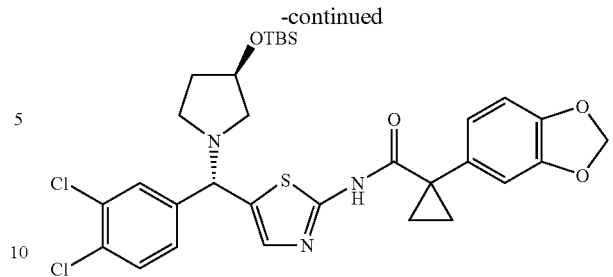

N-(5-(((S)-3-(tert-Butyldimethylsilyloxy)pyrrolidin-1-yl) (2-chlorophenyl)methyl)-4-methylthiazol-2-yl)-1-(2,2-difluorobenzo[d][1,3]dioxol-5-yl)cyclopropanecarboxamide (Isomer A) was made by the procedure used for 1-(benzo[d] [1,3]dioxol-5-yl)-N-(5-(((S)-3-(tert-butyldimethylsilyloxy) pyrrolidin-1-yl)(2-chlorophenyl)methyl)-4-methylthiazol-2-yl)cyclopropanecarboxamide (Isomer A) starting from N-(5-(amino(2-chlorophenyl)methyl)-4-methylthiazol-2-yl)-1-(2, 2-difluorobenzo[d][1,3]dioxol-5-yl) cyclopropanecarboxamide (Isomer A) and (S)-3-(tert-butyldimethylsilyloxy)-4-chlorobutanal (73%). $^1$H NMR (400 MHz, CDCl$_3$) δ 8.25 (s, 1H), 7.83 (dd, J=8.1, 1.6 Hz, 1H), 7.28-7.25 (m, 2H), 7.16-7.11 (m, 3H), 7.06 (d, J=8.1 Hz, 1H), 5.08 (s, 1H), 4.33 (m, 1H), 2.94 (dd, J=9.9, 6.2 Hz, 1H), 2.66 (td, J=8.3, 3.7 Hz, 1H), 2.54 (q, J=8.3 Hz, 1H), 2.36 (s, 3H), 2.18 (dd, J=9.9, 4.7 Hz, 1H), 2.02 (m, 1H), 1.75 (m, 2H), 1.65 (m, 1H), 1.20 (m, 2H), 0.86 (m, 9H), 0.01 (s, 3H), −0.01 (s, 3H); HPLC ret. time 3.69 min, 10-99% CH$_3$CN, 5 min run; ESI-MS 662.1 m/z (MH$^+$).

N-(5-(((S)-3-(tert-Butyldimethylsilyloxy)pyrrolidin-1-yl) (2-chlorophenyl)methyl)-4-methylthiazol-2-yl)-1-(2,2-difluorobenzo[d][1,3]dioxol-5-yl)cyclopropanecarboxamide (Isomer B) was made by the procedure used for 1-(benzo[d] [1,3]dioxol-5-yl)-N-(5-(((S)-3-(tert-butyldimethylsilyloxy) pyrrolidin-1-yl)(2-chlorophenyl)methyl)-4-methylthiazol-2-yl)cyclopropanecarboxamide (Isomer A) starting from N-(5-(amino(2-chlorophenyl)methyl)-4-methylthiazol-2-yl)-1-(2, 2-difluorobenzo[d][1,3]dioxol-5-yl) cyclopropanecarboxamide (Isomer B) and (S)-3-(tert-butyldimethylsilyloxy)-4-chlorobutanal (93%). $^1$H NMR (400 MHz, CDCl$_3$) δ 8.26 (s, 1H), 7.85 (dd, J=8.1, 1.7 Hz, 1H), 7.28-7.24 (m, 2H), 7.16-7.10 (m, 3H), 7.07 (d, J=8.2 Hz, 1H), 5.05 (s, 1H), 4.34 (m, 1H), 2.83 (dd, J=9.7, 6.3 Hz, 1H), 2.55-2.47 (m, 2H), 2.36-2.33 (m, 4H), 2.04 (m, 1H), 1.79-1.63 (m, 3H), 1.21 (m, 2H), 0.86 (m, 9H), 0.02 (s, 3H), 0.00 (s, 3H); HPLC ret. time 3.73 min, 10-99% CH$_3$CN, 5 min run; ESI-MS 662.1 m/z (MH$^+$).

1-(Benzo[d][1,3]dioxol-5-yl)-N-(5-(((R)-3-(tert-butyldimethylsilyloxy)pyrrolidin-1-yl)(3,4-dichlorophenyl) methyl)thiazol-2-yl)cyclopropanecarboxamide (Isomer A) was made by the procedure used for 1-(benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer A) starting from N-(5-(amino(3,4-dichlorophenyl)methyl)thiazol-2-yl)-1-(benzo[d][1,3] dioxol-5-yl)cyclopropanecarboxamide (Isomer A) and (R)-3-(tert-butyldimethylsilyloxy)-4-chlorobutanal (85%). $^1$H NMR (400 MHz, CDCl$_3$) δ 8.47 (s, 1H), 7.51 (d, J=2.0 Hz, 1H), 7.35 (d, J=8.3 Hz, 1H), 7.30 (dd, J=2.0, 8.3 Hz, 1H), 7.19 (s, 1H), 6.90-6.85 (m, 2H), 6.80 (d, J=7.9 Hz, 1H), 6.01 (s, 2H), 4.47 (s, 1H), 4.34 (m, 1H), 2.84 (dd, J=6.2, 9.8 Hz, 1H), 2.55-2.44 (m, 2H), 2.31 (dd, J=4.4, 9.9 Hz, 1H), 2.17 (s, 1H), 1.73-1.64 (m, 3H), 1.26-1.19 (m, 2H), 0.91 (s, 3H), 0.86 (s, 6H), 0.02 (s, 6H); HPLC ret. time 3.66 min, 10-99% CH$_3$CN, 5 min run; ESI-MS 646.5 m/z (MH$^+$).

1-(Benzo[d][1,3]dioxol-5-yl)-N-(5-(((R)-3-(tert-butyldimethylsilyloxy)pyrrolidin-1-yl)(3,4-dichlorophenyl) methyl)thiazol-2-yl)cyclopropanecarboxamide (Isomer B) was made by the procedure used for 1-(benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer A) starting from N-(5-(amino(3,4-dichlorophenyl)methyl)thiazol-2-yl)-1-(benzo[d][1,3] dioxol-5-yl)cyclopropanecarboxamide (Isomer B) and (R)-3-(tert-butyldimethylsilyloxy)-4-chlorobutanal (70%). $^1$H NMR (400 MHz, CDCl$_3$) δ 8.47 (s, 1H), 7.50 (d, J=2.0 Hz, 1H), 7.36 (d, J=8.3 Hz, 1H), 7.29 (dd, J=2.0, 8.3 Hz, 1H), 7.19 (s, 1H), 6.90-6.85 (m, 2H), 6.80 (d, J=7.9 Hz, 1H), 6.01 (s, 2H), 4.51 (s, 1H), 4.34 (m, J=3.4, 9.4 Hz, 1H), 2.88 (dd, J=6.2, 10.0 Hz, 1H), 2.67-2.62 (m, 1H), 2.53 (dd, J=8.2, 16.7 Hz, 1H), 2.17 (dd, J=4.4, 10.0 Hz, 1H), 2.07-1.78 (m, 1H), 1.75-1.63 (m, 3H), 1.22-1.18 (m, 2H), 0.86 (d, J=2.5 Hz, 9H), 0.01 (m, 6H); HPLC ret. time 3.67 min, 10-99% CH$_3$CN, 5 min run; ESI-MS 646.4 m/z (MH$^+$).

1-(Benzo[d][1,3]dioxol-5-yl)-N-(5-((R)-(2-chlorophenyl)((S)-3-hydroxypyrrolidin-1-yl)methyl)-4-methylthiazol-2-yl)cyclopropanecarboxamide and 1-(Benzo[d][1,3]dioxol-5-yl)-N-(5-((S)-(2-chlorophenyl)((S)-3-hydroxypyrrolidin-1-yl)methyl)-4-methylthiazol-2-yl)cyclopropanecarboxamide 1-(Benzo[d][1,3]dioxol-5-yl)-N-(5-((R)-((R)-3-(tert-butyldimethylsilyloxy)pyrrolidin-1-yl)(3,4-dichlorophenyl)methyl)thiazol-2-yl)cyclopropanecarboxamide and 1-(Benzo[d][1,3]dioxol-5-yl)-N-(5-((S)-((R)-3-(tert-butyldimethylsilyloxy)pyrrolidin-1-yl)(3,4-dichlorophenyl)methyl)thiazol-2-yl)cyclopropanecarboxamide

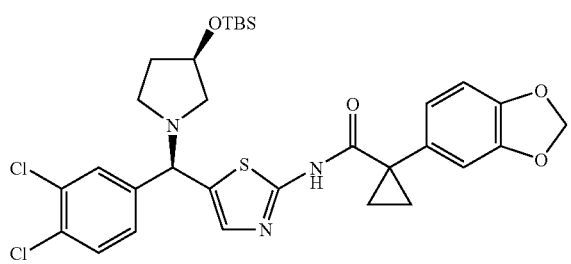
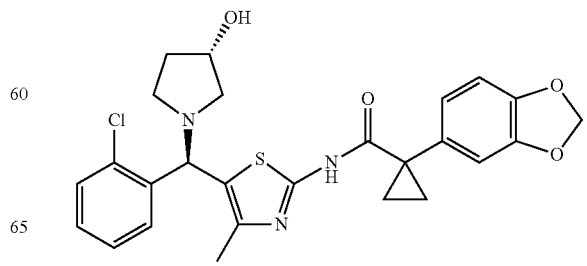

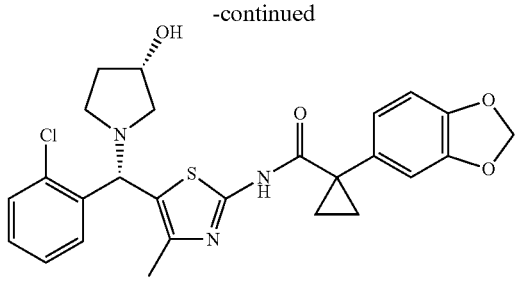

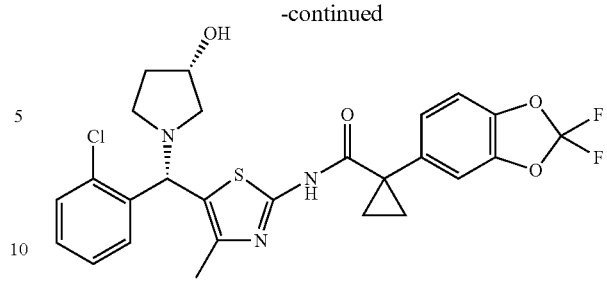

A mixture of 1-(benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer A) (400 mg, 0.64 mmol) and TBAF (1M in THF, 3.84 mL, 3.84 mmol) was stirred at room temperature for 5 h. The reaction was partitioned between H₂O and EtOAc. The combined organic layers were washed with brine, dried over MgSO₄ and concentrated. The residue was adsorbed onto silica gel and purified by column chromatography (25-75% EtOAc/hexanes) to afford 1-(benzo[d][1,3]dioxol-5-yl)-N-(5-((2-chlorophenyl)((S)-3-hydroxypyrrolidin-1-yl)methyl)-4-methylthiazol-2-yl)cyclopropanecarboxamide (Isomer A) as a pale yellow solid (245 mg, 75%, >99% de). $^1$H NMR (400 MHz, CDCl₃) δ 8.41 (s, 1H), 7.85 (dd, J=8.1, 1.7 Hz, 1H), 7.29-7.26 (m, 2H), 7.14 (m, 1H), 6.88-6.84 (m, 2H), 6.79 (d, J=7.9 Hz, 1H), 6.00 (s, 2H), 5.07 (s, 1H), 4.30 (m, 1H), 2.79 (td, J=8.6, 5.8 Hz, 1H), 2.63-2.56 (m, 2H), 2.36 (s, 3H), 2.29 (td, J=9.0, 5.9 Hz, 1H), 2.15 (m, 1H), 1.85 (d, J=7.9 Hz, 1H), 1.78-1.65 (m, 3H), 1.18 (m, 2H); HPLC ret. time 2.70 min, 10-99% CH₃CN, 5 min run; ESI-MS 512.5 m/z (MH⁺).

1-(Benzo[d][1,3]dioxol-5-yl)-N-(5-((2-chlorophenyl)((S)-3-hydroxypyrrolidin-1-yl)methyl)-4-methylthiazol-2-yl)cyclopropanecarboxamide (Isomer B) was made by the procedure used for (Isomer A) starting from 1-(benzo[d][1,3]dioxol-5-yl)-N-(5-(((S)-3-(tert-butyldimethylsilyloxy)pyrrolidin-1-yl)(2-chlorophenyl)methyl)-4-methylthiazol-2-yl)cyclopropanecarboxamide (Isomer B) (50%, >99% de). $^1$H NMR (400 MHz, CDCl₃) δ 8.44 (s, 1H), 7.84 (dd, J=7.8, 1.5 Hz, 1H), 7.29-7.25 (m, 2H), 7.14 (td, J=7.6, 1.7 Hz, 1H), 6.88-6.84 (m, 2H), 6.79 (d, J=7.9 Hz, 1H), 6.00 (s, 2H), 5.07 (s, 1H), 4.29 (m, 1H), 2.83 (td, J=8.6, 5.0 Hz, 1H), 2.61 (d, J=10.1 Hz, 1H), 2.49 (m, 1H), 2.36-2.29 (m, 4H), 2.17 (m, 1H), 1.89 (d, J=7.9 Hz, 1H), 1.76-1.66 (m, 3H), 1.19 (m, 2H); HPLC ret. time 2.71 min, 10-99% CH₃CN, 5 min run; ESI-MS 512.5 m/z (MH⁺).

N-(5-((R)-(2-Chlorophenyl)((S)-3-hydroxypyrrolidin-1-yl)methyl)-4-methylthiazol-2-yl)-1-(2,2-difluorobenzo[d][1,3]dioxol-5-yl)cyclopropanecarboxamide and N-(5-((S)-(2-Chlorophenyl)((S)-3-hydroxypyrrolidin-1-yl)methyl)-4-methylthiazol-2-yl)-1-(2,2-difluorobenzo[d][1,3]dioxol-5-yl)cyclopropanecarboxamide N-(5-((2-Chlorophenyl)((S)-3-hydroxypyrrolidin-1-yl)methyl)-4-methylthiazol-2-yl)-1-(2,2-difluorobenzo[d][1,3]dioxol-5-yl)cyclopropanecarboxamide (Isomer A) was made by the procedure used for 1-(benzo[d][1,3]dioxol-5-yl)-N-(5-((2-chlorophenyl)((S)-3-hydroxypyrrolidin-1-yl)methyl)-4-methylthiazol-2-yl)cyclopropanecarboxamide (Isomer A) starting from N-(5-(((S)-3-(tert-Butyldimethylsilyloxy)pyrrolidin-1-yl)(2-chlorophenyl)methyl)-4-methylthiazol-2-yl)-1-(2,2-difluorobenzo[d][1,3]dioxol-5-yl)cyclopropanecarboxamide (Isomer A) (72%). $^1$H NMR (400 MHz, CDCl₃) δ 8.28 (s, 1H), 7.84 (dd, J=8.1, 1.7 Hz, 1H), 7.30-7.26 (m, 2H), 7.17-7.12 (m, 3H), 7.07 (d, J=8.2 Hz, 1H), 5.07 (s, 1H), 4.30 (m, 1H), 2.79 (td, J=8.6, 5.7 Hz, 1H), 2.62-2.55 (m, 2H), 2.35 (s, 3H), 2.28 (td, J=9.0, 5.9 Hz, 1H), 2.15 (m, 1H), 1.86 (d, J=7.9 Hz, 1H), 1.80-1.71 (m, 3H), 1.21 (m, 2H); HPLC ret. time 2.91 min, 10-99% CH₃CN, 5 min run; ESI-MS 548.3 m/z (MH⁺).

N-(5-((2-Chlorophenyl)((S)-3-hydroxypyrrolidin-1-yl)methyl)-4-methylthiazol-2-yl)-1-(2,2-difluorobenzo[d][1,3]dioxol-5-yl)cyclopropanecarboxamide (Isomer B) was made by the procedure used for 1-(benzo[d][1,3]dioxol-5-yl)-N-(5-((2-chlorophenyl)((S)-3-hydroxypyrrolidin-1-yl)methyl)-4-methylthiazol-2-yl)cyclopropanecarboxamide (Isomer A) starting from N-(5-(((S)-3-(tert-Butyldimethylsilyloxy)pyrrolidin-1-yl)(2-chlorophenyl)methyl)-4-methylthiazol-2-yl)-1-(2,2-difluorobenzo[d][1,3]dioxol-5-yl)cyclopropanecarboxamide (Isomer B) (85%). $^1$H NMR (400 MHz, CDCl₃) δ 8.28 (s, 1H), 7.82 (dd, J=7.7, 1.5 Hz, 1H), 7.30-7.25 (m, 2H), 7.14 (m, 3H), 7.07 (d, J=8.2 Hz, 1H), 5.07 (s, 1H), 4.29 (m, 1H), 2.83 (td, J=8.7, 5.1 Hz, 1H), 2.61 (d, J=10.0 Hz, 1H), 2.50 (dd, J=10.1, 5.1 Hz, 1H), 2.36-2.29 (m, 4H), 2.17 (m, 1H), 1.88 (d, J=7.8 Hz, 1H), 1.82-1.70 (m, 3H), 1.22 (m, 2H); HPLC ret. time 2.94 min, 10-99% CH₃CN, 5 min run; ESI-MS 548.3 m/z (MH⁺).

1-(Benzo[d][1,3]dioxol-5-yl)-N-(5-((R)-(3,4-dichlorophenyl)((R)-3-hydroxypyrrolidin-1-yl)methyl)thiazol-2-yl)cyclopropanecarboxamide and 1-(Benzo[d][1,3]dioxol-5-yl)-N-(5-((S)-(3,4-dichlorophenyl)((R)-3-hydroxypyrrolidin-1-yl)methyl)thiazol-2-yl)cyclopropanecarboxamide

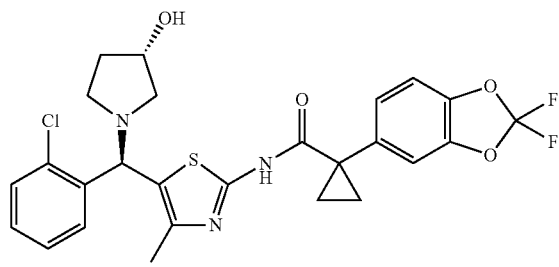

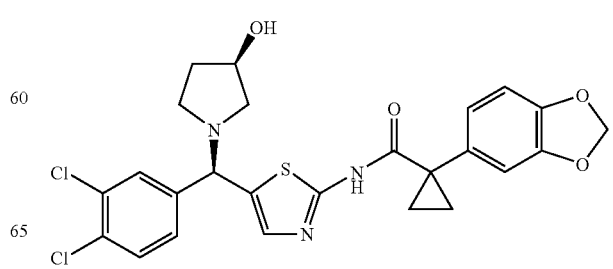

-continued

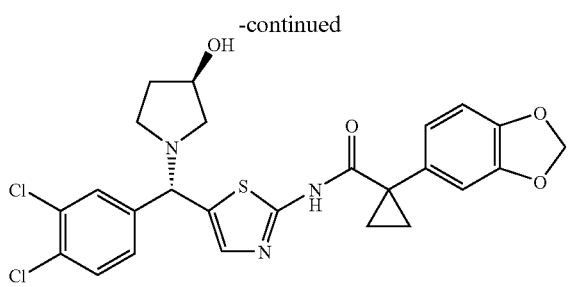

1-(Benzo[d][1,3]dioxol-5-yl)-N-(5-((3,4-dichlorophenyl)((R)-3-hydroxypyrrolidin-1-yl)methyl)thiazol-2-yl)cyclopropanecarboxamide (Isomer A) was made by the procedure used for 1-(benzo[d][1,3]dioxol-5-yl)-N-(5-((2-chlorophenyl)((S)-3-hydroxypyrrolidin-1-yl)methyl)-4-methylthiazol-2-yl)cyclopropanecarboxamide (Isomer A) starting from 1-(benzo[d][1,3]dioxol-5-yl)-N-(5-(((R)-3-(tert-butyldimethylsilyloxy)pyrrolidin-1-yl)(3,4-dichlorophenyl)methyl)thiazol-2-yl)cyclopropanecarboxamide (Isomer A) The crude product was purified by column chromatography (60-90% EtOAc/Hexane) (74%, 98% de). $^1$H NMR (400 MHz, CDCl$_3$) δ 8.49 (s, 1H), 7.50 (d, J=2.0 Hz, 1H), 7.37 (d, J=8.3 Hz, 1H), 7.31 (dd, J=2.0, 8.3 Hz, 1H), 7.20 (s, 1H), 6.90-6.86 (m, 2H), 6.81 (d, J=7.9 Hz, 1H), 6.01 (s, 2H), 4.48 (s, 1H), 4.32 (m, 1H), 2.82-2.76 (m, 1H), 2.59-2.57 (m, 1H), 2.51 (q, J=5.1 Hz, 1H), 2.33 (td, J=8.9, 6.1 Hz, 1H), 2.16 (dd, J=5.3, 12.5 Hz, 1H), 1.81-1.69 (m, 4H), 1.22 (dd, J=5.0, 7.6 Hz, 2H); HPLC ret. time 2.81 min, 10-99% CH$_3$CN, 5 min run; ESI-MS 532.2 m/z (MH$^+$).

1-(Benzo[d][1,3]dioxol-5-yl)-N-(5-((3,4-dichlorophenyl)((R)-3-hydroxypyrrolidin-1-yl)methyl)thiazol-2-yl)cyclopropanecarboxamide (Isomer B) was made by the procedure used for (Isomer A) starting from 1-(benzo[d][1,3]dioxol-5-yl)-N-(5-(((R)-3-(tert-butyldimethylsilyloxy)pyrrolidin-1-yl)(3,4-dichlorophenyl)methyl)thiazol-2-yl)cyclopropanecarboxamide (Isomer B) (78%, 95% de). $^1$H NMR (400 MHz, CDCl$_3$) δ 8.49 (s, 1H), 7.52 (d, J=2.0 Hz, 1H), 7.37 (d, J=8.3 Hz, 1H), 7.30 (dd, J=2.0, 8.3 Hz, 1H), 7.20 (s, 1H), 6.90-6.86 (m, 2H), 6.81 (d, J=7.9 Hz, 1H), 6.01 (s, 2H), 4.48 (s, 1H), 4.34-4.32 (m, 1H), 2.76 (td, J=8.5, 6.0 Hz, H), 2.57 (m, 2H), 2.29 (m, 1H), 2.15 (q, J=7.2 Hz, 1H), 1.81-1.68 (m, 4H), 1.25-1.20 (m, 2H); HPLC ret. time 2.80 min, 10-99% CH$_3$CN, 5 min run; ESI-MS 532.2 m/z (MH$^+$).

Assays for Detecting and Measuring ΔF508-CFTR Correction Properties of Compounds I) Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hoursB) Electrophysiological Assays for assaying ΔF508-CFTR modulation properties of compounds 1. Ussing Chamber Assay Ussing chamber experiments were performed on polarized epithelial cells expressing ΔF508-CFTR to further characterize the ΔF508-CFTR modulators identified in the optical assays. FRT$^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^-$ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl$^-$ concentration gradient. To set up this gradient, normal ringer was used on the basolateral membrane, whereas apical NaCl was replaced by equimolar sodium gluconate (titrated to pH 7.4 with NaOH) to give a large Cl$^-$ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

To determine the activity of correction compounds for increasing the density of functional ΔF508-CFTR in the plasma membrane, we used the above-described perforatedpatch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

Table 3 illustrates the EC50 and relative efficacy of exemplary embodiments of the present invention. In Table 3, the following meanings apply:

EC50: "+++" means<2 uM; "++" means between 2 uM to 20 uM; "+" means between 25 uM to 60 uM.

% Efficacy: "+" means<25%; "++" means between 25% to 100%; "+++" means>100%.

TABLE 3

| Cmpd No. | EC 50 | % Efficacy |
|---|---|---|
| 1 | +++ | +++ |
| 2 | ++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | ++ |
| 13 | +++ | +++ |

As illustrated in Table 3 above, the compounds of the present invention exhibit unexpectedly better correction activity as measured by the assays above.

The invention claimed is:

1. A compound of formula I or formula II:

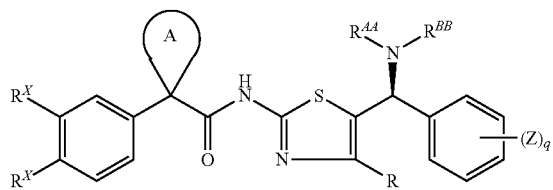

I

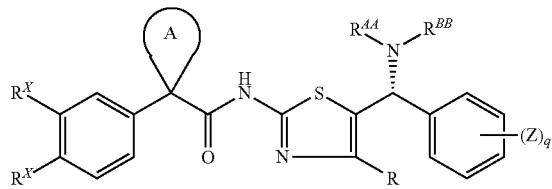

II or a pharmaceutically acceptable salt thereof, wherein:
each $R^X$ is independently hydrogen, halo, $CF_3$, $C_1$-$C_4$ alkyl, or —$OC_1$-$C_4$ alkyl; provided that both $R^X$ are not simultaneously hydrogen; or
the two $R^X$, taken together form ring (a):

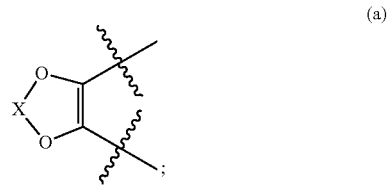

(a)

X is $CH_2$, $CF_2$, $CH_2$—$CH_2$, or $CF_2$—$CF_2$;
ring A is 3-7 membered monocyclic cycloalkyl ring;
$R^{AA}$ and $R^{BB}$, taken together with the nitrogen atom, form a pyrrolidinyl ring substituted with OR';
R' is hydrogen or $C_1$-$C_6$ aliphatic, wherein up to two carbon units of said aliphatic are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR—, —NRNRCO—, —NRCO—, —S—, —SO, —$SO_2$—, —NR—, —$SO_2$NR—, $NRSO_2$—, or —$NRSO_2$NR—;
R is hydrogen or $C_1$-$C_6$ aliphatic;
Z is halo, CN, COOH, $CF_3$, or difluoromethylenedioxy; and
q is 0-3.

2. The compound according to claim 1, wherein two $R^X$ taken together form ring (a) and X is $CH_2$.

3. The compound according to claim 1, wherein two $R^X$ taken together form ring (a) and X is $CF_2$.

4. The compound according to claim 1, wherein one $R^X$ is hydrogen and the other $R^X$ is halo, $CF_3$, $C_1$-$C_4$ alkyl, or —$OC_1$-$C_4$ alkyl.

5. The compound according to claim 1, wherein one $R^X$ is hydrogen and the other $R^X$ is 4-methoxy.

6. The compound according to any one of claims 1-5, wherein ring A is cyclopropyl, cyclopentyl, or cyclohexyl.

7. The compound according to claim 6, wherein ring A is cyclopropyl or cyclopentyl.

8. The compound according to claim 6, wherein ring A is cyclopropyl.

9. The compound according to claim 1 wherein R' is hydrogen.

10. The compound according to claim 1, wherein R' is $C_{1-6}$ alkyl.

11. The compound according to claim 1, wherein $R^{AA}$ and $R^{BB}$, taken together, form a pyrrolidinyl with an OH substituent.

12. The compound according to claim 1, wherein Z is selected from halo, $CF_3$, or difluoromethylenedioxy.

13. The compound according to claim 1, wherein q is 0.

14. The compound according to claim 1, wherein q is 1.

15. The compound according to claim 1, wherein R is hydrogen.

16. The compound according to claim 1, wherein compounds of formula I or formula II comprise one or more, and preferably all, of the following features:

two $R^X$ taken together form ring (a);
X is $CH_2$;
ring A is cyclopropyl;
R is hydrogen;
q is 1; and
Z is halo, $CF_3$, or difluoromethylenedioxy.

17. The compound according to claim 1, wherein $R^{AA}$ and $R^{BB}$ in formula I, taken together with the nitrogen atom, form the following ring (i):

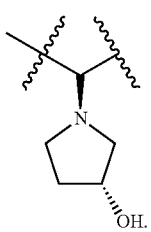
(i)

18. The compound according to claim 1, wherein $R^{AA}$ and $R^{BB}$ in formula I, taken together with the nitrogen atom, form the following ring (ii):

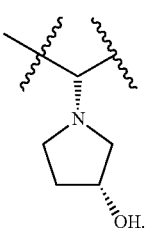
(ii)

19. A compound selected from

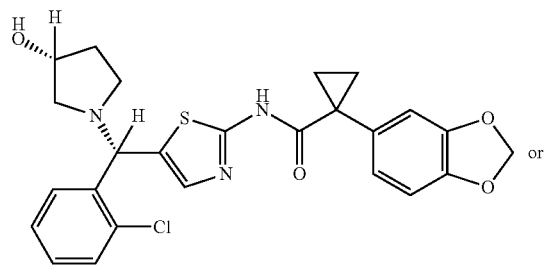
or

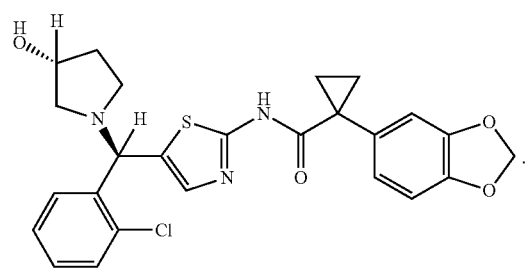

20. A pharmaceutical composition comprising:
(i) a compound according to claim 1 or 19; and
(ii) a pharmaceutically acceptable carrier.

21. The composition of claim 20, optionally further comprising a CFTR potentiator.

22. A kit for use in measuring the activity of CFTR or a fragment thereof in a biological sample in vitro or in vivo, comprising:
(i) a first composition comprising a compound according to claim 1; and
(ii) instructions for:
 a) contacting the composition with the biological sample;
 b) measuring activity of said CFTR or a fragment thereof.

23. The kit according to claim 22, further comprising instructions for
a) contacting an additional composition with the biological sample;
b) measuring the activity of said CFTR or a fragment thereof in the presence of said additional composition, and
c) comparing the activity of the CFTR in the presence of the additional composition with the density of the CFTR in the presence of said first composition.

24. The kit according to claim 23, wherein the kit is used to measure the density of CFTR.

25. A compound of formula I' or formula II':

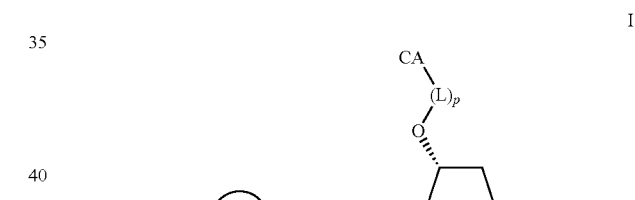
I'

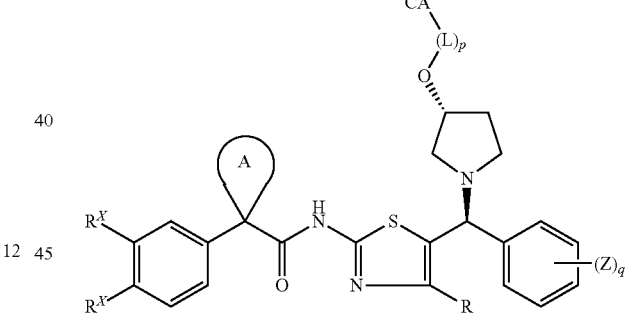
II';

wherein:
R$^X$ is independently hydrogen, halo, CF$_3$, C$_1$-C$_a$ alkyl, or —OC$_1$-C$_4$ alkyl; provided that both R$^X$ are not simultaneously hydrogen; or
the two R$^X$, taken together form ring (a):

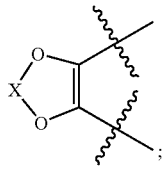

(a)

X is CH$_2$, CF$_2$, CH$_2$—CH$_2$, or CF$_2$—CF$_2$;
ring A is 3-7 membered monocyclic cycloalkyl ring;
Z is halo, CN, COOH, CF$_3$, or difluoromethylenedioxy;
q is 0-3;
L is a linker selected from C(O) or SO$_2$;
p is 0 or 1;
R is H or C$_1$-C$_6$ aliphatic; and
CA is a suitable chiral auxiliary, wherein CA, L, p, and the oxygen atom linked thereto, taken together, is (+)-10-camphorsulfonate, (1S,4R)-(−)-ω-camphanic ester, (1R,2S,5R)-(−) mentholcarbonate, (1S,2R,5S)-(+)-mentholcarbonate, (1R,2R)-1-phenyl-2-cyclopropylester, or (3R)-tetrahydrofuran-3-carbonate.

* * * * *